US012690591B2

(12) United States Patent
Bhujade et al.

(10) Patent No.: US 12,690,591 B2
(45) Date of Patent: Jul. 28, 2026

(54) FUNGICIDAL COMPOSITION CONTAINING OXADIAZOLE COMPOUNDS

(71) Applicant: PI INDUSTRIES LIMITED, Udaipur-Rajasthan (IN)

(72) Inventors: Paras Raybhan Bhujade, Kopargaon Ahmednagar (IN); Maruti N. Naik, Karnataka (IN); Santosh Shridhar Autkar, Maharashtra (IN); Alexander G.M. Klausener, Pulheim (DE)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 98 days.

(21) Appl. No.: 18/563,010

(22) PCT Filed: May 25, 2022

(86) PCT No.: PCT/IB2022/054871

§ 371 (c)(1),
(2) Date: Nov. 21, 2023

(87) PCT Pub. No.: WO2022/249074

PCT Pub. Date: Dec. 1, 2022

(65) Prior Publication Data

US 2024/0225002 A1 Jul. 11, 2024

(30) Foreign Application Priority Data

May 26, 2021 (IN) ............................ 202111023436

(51) Int. Cl.

| | |
|---|---|
| ***A01N 43/82*** | (2006.01) |
| ***A01N 25/04*** | (2006.01) |
| ***A01P 3/00*** | (2006.01) |
| ***C07D 271/06*** | (2006.01) |
| ***C07D 413/04*** | (2006.01) |

(52) U.S. Cl.

CPC ............ *A01N 43/82* (2013.01); *A01N 25/04* (2013.01); *A01P 3/00* (2021.08); *C07D 271/06* (2013.01); *C07D 413/04* (2013.01)

(58) Field of Classification Search

CPC ..................................................... A01N 43/82

See application file for complete search history.

(56) References Cited

U.S. PATENT DOCUMENTS

2022/0151234 A1* 5/2022 Bhujade ............... C07D 403/12

FOREIGN PATENT DOCUMENTS

| | | | |
|---|---|---|---|
| EP | 3 660 007 | A1 | 6/2020 |
| WO | 2017220485 | A1 | 12/2017 |
| WO | 2019022061 | A1 | 1/2019 |
| WO | 2020208511 | A1 | 10/2020 |

OTHER PUBLICATIONS

PCT—ISR (PCT/IB2022/054871)—Sep. 27, 2022 (3 pgs).
PCT—WR OPN ((PCT/IB2022/054871)—Sep. 27, 2022 (7 pgs).

* cited by examiner

*Primary Examiner* — Valerie Rodriguez-Garcia
(74) *Attorney, Agent, or Firm* — Lippes Mathias LLP

(57) ABSTRACT

The present invention discloses a novel fungicidal composition comprising at least one compound of formula (I) or an agriculturally acceptable salt thereof as a component (1), Formula (I)

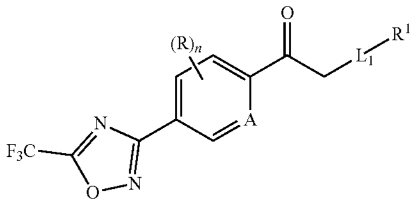

wherein, R, A, $L_1$, $R^1$, and n are as defined in the detailed description and at least one further active compound as a component (2). The present invention further discloses a method for controlling or preventing infestation of plants by phytopathogenic microorganisms and use of the fungicidal composition according to invention for the treatment of seed.

10 Claims, No Drawings

FUNGICIDAL COMPOSITION CONTAINING OXADIAZOLE COMPOUNDS

This application is a National Stage Entry of International Application No. PCT/IB2022/054871, filed May 25, 2022, which claims priority to Indian Application No. 202111023436, filed May 26, 2021, the contents of which are incorporated by reference herein.

FIELD OF THE INVENTION

The present invention relates to a novel fungicidal composition comprising a mixture of at least one oxadiazole compound of formula (I) as a component (1) and at least one further active compound as a component (2). Further, the present invention relates to a method for controlling or preventing infestation of plants by phytopathogenic microorganisms, to the use of a novel fungicidal composition for the treatment of one or more seeds and to the corresponding treated seeds.

BACKGROUND OF THE INVENTION

Oxadiazole compounds are known to be useful as crop protection agents to combat or prevent infestations of microorganism. For instance, WO2017110862, WO2015185485 and WO2020208511 describe the use of substituted oxadiazoles for combating phytopathogenic fungi.

Although, many fungicidal compounds and compositions, belonging to various chemical classes, have been developed for the use as fungicides in crops of useful plants, crop tolerance and activity against particular phytopathogenic fungi do not always satisfy the needs of the agricultural practice in many respects.

Therefore, there is a continuing need to find new compounds and compositions having superior biological properties for the use in controlling or preventing an infestation of plants by phytopathogenic fungi. For example, compounds possessing a higher biological activity, an advantageous spectrum of efficacy, an increased safety profile, improved physico-chemical properties and increased biodegradability. Or else, compositions possessing a broader spectrum of activity, improved crop tolerance, synergistic interactions or potentiating properties, or compositions which display a more rapid onset of action or which have longer lasting activity or which enable a reduction in the number of applications and/or a reduction in the application rate of the compounds and compositions required for an effective control of a phytopathogen, thereby enabling beneficial resistance-management practices, reduced environmental impact and reduced operator exposure.

The combinations of fungicides are often used to facilitate better disease control and to retard resistance development. It is desirable to broaden the spectrum of activity and to increase the efficacy of disease control by using mixtures of active ingredients that provide a combination of curative, systemic and preventative control of plant pathogens. Also desirable are combinations that provide greater long lasting efficacy to allow for extended spray intervals. It is also very desirable to combine fungicidal agents that inhibit different biochemical pathways in the fungal pathogens to retard the development of resistance to any one particular plant disease control agent.

The use of compositions comprising mixtures/combinations of different fungicidal compounds possessing different modes of action can address some of these needs (e.g., by combining fungicides with differing spectrums of activity). The present invention provides fungicidal compositions which in some aspects at least achieve the stated objective.

Surprisingly, it has been found that the novel fungicidal compositions according to the invention not only bring about the additive enhancement of the spectrum of action with respect to the phytopathogens to be controlled, that was in principle to be expected, but also achieve a synergistic effect. The synergistic effect of the fungicidal compositions of the present invention helps to reduce the application rate of component (1) and component (2) by maintaining the level of efficacy even if the two individual components alone have become significantly lower active or even ineffective at such low application rates. In addition it allows a substantial broadening of the spectrum of phytopathogens that can be controlled by, at the same time, increasing the safety in use.

Thus, the use of the novel agrochemical compositions according to the invention contributes considerably to keeping young crop stands healthy, which increases, for example, the survival of the treated seed as well as safeguards quality and yield.

Moreover, the novel agrochemical compositions according to the invention may contribute to an enhanced systemic action. Even if the individual compounds of the combination do not have sufficient systemic properties, the novel agrochemical composition according to the invention may still have this property. In a similar manner, the novel agrochemical compositions according to the invention may result in higher long lasting efficacy of the fungicidal and/or insecticidal and/or nematicidal action.

SUMMARY OF THE INVENTION

The present invention provides a novel fungicidal composition comprising a mixture of component (1) and component (2), wherein component (1) is at least one compound of formula (I) or an agriculturally acceptable salt thereof;

Formula (I)

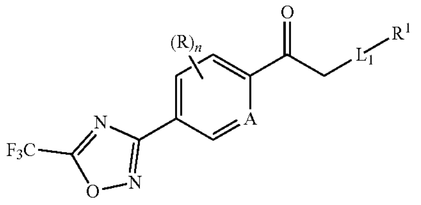

wherein;

R is selected from the group consisting of hydrogen, halogen, $C_1$-$C_6$-alkyl, $C_1$-$C_6$-alkoxy, $C_1$-$C_6$-alkoxy-$C_1$-$C_4$-alkyl and $C_1$-$C_6$-haloalkyl;

A represents CR or N;

$L^1$ represents —$NR^2$—, —O— or —$S(O)_{0-2}$—;

$R^1$ is selected from the group consisting of $C_1$-$C_6$-alkyl, $C_2$-$C_6$-alkenyl, $C_3$-$C_8$-cycloalkyl, $C_6$-$C_{10}$-aryl, $C_7$-$C_{14}$-aralkyl and $C_3$-$C_{10}$-heterocyclyl; each group of $R^1$ may optionally be substituted with one or more groups of $R^{1a}$;

$R^{1a}$ is selected from the group consisting of halogen, cyano, nitro, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxy, $C_1$-$C_6$-haloalkoxy, $C_1$-$C_6$-alkoxy-$C_1$-$C_4$-alkyl, $C_1$-$C_6$-hydroxyalkyl, $C_2$-$C_6$-haloalkenyl, $C_2$-$C_6$-haloalkynyl and $C_3$-$C_8$-halocycloalkyl;

$R^2$ is selected from the group consisting of hydrogen and $C_1$-$C_6$-alkyl; or $R^1$ and $R^2$ together with the atoms to which they are attached may form a 3- to 8-membered heterocyclic ring or ring system, wherein the heteroatom is selected from the group consisting of N, O and $S(O)_{0-2}$, wherein the heterocyclic ring or ring system may be optionally substituted with halogen, $C_1$-$C_6$-alkyl, $C_1$-$C_6$-haloalkyl or $C_1$-$C_6$-alkoxy;

n represents integers 0 to 2;

and component (2) is at least one further active compound selected from the following groups:
- (A) Respiration Inhibitors
- (B) Sterol Biosynthesis Inhibitors (SBI Fungicides)
- (C) Nucleic acid synthesis inhibitors
- (D) Inhibitors of cell division and cytoskeleton
- (E) Inhibitors of amino acid and protein synthesis
- (F) Signal transduction inhibitors
- (G) Lipid and membrane synthesis inhibitors
- (H) Inhibitors with Multi Site Action
- (I) Cell wall synthesis inhibitors of glucan synthesis
- (J) Plant defence inducers
- (K) Unknown mode of action
- (L) Insecticides.

In one embodiment, the present invention provides a method for controlling or preventing the infestation of plants by phytopathogenic microorganisms comprising the step of applying the fungicidal composition to the microorganisms and/or their habitat (to the plants, plant parts, seeds, fruits or to the soil in which the plants grow).

DETAILED DESCRIPTION OF THE INVENTION

Definitions

The definitions provided herein for the terminologies used in the present disclosure are for illustrative purpose only and in no manner limit the scope of the present invention disclosed in the present disclosure.

Hydrogen: Preferably, the definition of hydrogen encompasses also isotopes of hydrogen, preferably deuterium and tritium, more preferably deuterium.

The term “halogen” (also in combinations such as haloalkyl, haloalkoxy etc.) means fluorine, chlorine, bromine and iodine, and preferably fluorine, chlorine, bromine and more preferably fluorine, chlorine;

The term “alkyl” (including in combinations such as alkoxy etc.) means saturated, straight-chain or branched hydrocarbyl radicals having 1 to 6 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl and octyl. If the alkyl is at the end of a composite substituent, as, for example, in alkylcycloalkyl, the part of the composite substituent at the start, for example the cycloalkyl, may be mono- or polysubstituted identically or differently and independently by alkyl.

The term “haloalkyl” (including in combinations such as haloalkoxy etc.) means straight-chain or branched alkyl groups having 1 to 6 carbon atoms (as specified above), where some or all of the hydrogen atoms in these groups may be replaced by halogen atoms as specified above, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

The term “cycloalkyl” means alkyl closed to form a ring. Examples include but are not limited to cyclopropyl, cyclopentyl and cyclohexyl. This definition also applies to cycloalkyl as a part of a composite substituent, for example cycloalkylalkyl etc., unless specifically defined elsewhere.

The term “alkoxy” used either alone or in compound words includes $C_1$-$C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the different isomers.

The term “haloalkoxy” means straight-chain or branched alkoxy groups where some or all of the hydrogen atoms in these groups may be replaced by halogen atoms as specified above. Non-limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term “hydroxy” means —OH, amino means —NRR, wherein R can be H or any possible substituent such as alkyl. Carbonyl means —C(═O)—, carbonyloxy means —OC(═O)—, sulfinyl means SO, sulfonyl means $S(O)_2$.

The term “hydroxyalkyl” as used herein refers to a straight-chain or branched alcohol preferably having 1 to 6 carbon atoms, for example methanol, ethanol, n-propanol, isopropanol, n-butanol, isobutanol, s-butanol and t-butanol. Preference is also given to hydroxyalkyl groups having 1 to 4 carbon atoms. The inventive hydroxyalkyl groups may be substituted by one or more identical or different radicals.

Halocycloalkyl, halocycloalkenyl, alkylcycloalkyl, cycloalkylalkyl, cycloalkoxyalkyl, alkylsulfinylalkyl, alkylsulfonylalkyl, haloalkylcarbonyl, cycloalkylcarbonyl, haloalkoxylalkyl, and the like, are defined analogously to the above examples.

The term “carbocycle or carbocyclic” includes an “aromatic carbocyclic ring system” and a “non-aromatic carbocylic ring system” or polycyclic or bicyclic (spiro, fused, bridged, nonfused) ring compounds in which the ring may be aromatic or non-aromatic (where aromatic indicates that the Huckel rule is satisfied and non-aromatic indicates that the Huckel rule is not statisfied).

The term "heterocycle or heterocyclic" includes an "aromatic heterocycle or heteroaryl ring system" and a "non-aromatic heterocycle ring system" or polycyclic or bicyclic (spiro, fused, bridged, nonfused) ring compounds in which the ring may be aromatic or non-aromatic, wherein the heterocyclic ring contains at least one heteroatom selected from N, O, $S(O)_{0-2}$, and/or a C ring member of the heterocycle may be replaced by C(═O), C(═S), C(═CR*R*) and C═NR*, * indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; non-limiting examples include thietanyl, oxetanyl, oxiranyl, aziridinyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-1-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, pyrrolinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidinyl, 2-piperidinyl, 3-piperidinyl, 4-piperidinyl, pyrazynyl, morpholinyl, thiomorphlinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, cycloserines, 2,3,4,5-tetrahydro[1H]azepin-1- or -2- or -3- or -4- or -5- or -6- or -7-yl, 3,4,5,6-tetra-hydro[2H]azepin-2- or -3- or -4- or -5- or -6- or 7-yl, 2,3,4,7-tetrahydro[1H]azepin-1- or -2- or -3- or -4- or -5- or -6- or 7-yl, 2,3,6,7-tetrahydro[1H]azepin-1- or -2- or -3- or -4- or -5- or -6- or -7-yl, hexahydroazepin-1- or -2- or -3- or -4-yl, tetra- and hexahydrooxepinyl such as 2,3,4,5-tetrahydro[1H]oxepin-2- or -3- or -4- or -5- or -6- or -7-yl, 2,3,4,7-tetrahydro[1H]oxepin-2- or -3- or -4- or -5- or -6- or -7-yl, 2,3,6,7-tetrahydro[1H]oxepin-2- or -3- or -4- or -5- or -6- or -7-yl, hexahydroazepin-1- or -2- or -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl. This definition also applies to heterocyclyl as a part of a composite substituent, for example heterocyclylalkyl etc., unless specifically defined elsewhere.

The term "heteroaryl" or "aromatic heterocyclic" means a 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom; 5-membered heteroaryl groups which, in addition to carbon atoms, may contain one to four nitrogen atoms or one to three nitrogen atoms and one sulphur or oxygen atom as ring members, non-limiting examples include furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, non-limiting examples 1-pyrrolyl, 1-pyrazolyl, 1,2,4-triazol-1-yl, 1-imidazolyl, 1,2,3-triazol-1-yl and 1,3,4-triazol-1-yl.

6-membered heteroaryl which contains one to four nitrogen atoms: 6-membered heteroaryl groups which, in addition to carbon atoms, may contain, respectively, one to three and one to four nitrogen atoms as ring members, non-limiting examples include 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl; benzofused 5-membered heteroaryl containing one to three nitrogen atoms or one nitrogen atom and one oxygen or sulphur atom: non-limiting examples include indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, I-benzofuran-5-yl, 1-benzofuran-6-yl, 1-benzofuran-7-yl, 1-benzothiophen-2-yl, I-benzothiophen-3-yl, I-benzothiophen-4-yl, 1-benzothiophen-5-yl, I-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl; benzofused 6-membered heteroaryl which contains one to three nitrogen atoms: non-limiting examples include quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

The total number of carbon atoms in a substituent group is indicated by the "$C_i$-$C_j$" prefix where i and j are numbers from 1 to 21. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula (I) is comprised of one or more heterocyclic rings, all substituents are attached to these rings through any available carbon or nitrogen by replacement of a hydrogen on said carbon or nitrogen.

Depending on the nature of the substituents, the compounds of formula (I) can be present as mixtures of different possible isomeric forms, in particular of stereoisomers, such as, for example, E and Z, threo and erythro, and also optical isomers, and, if appropriate, also of tautomers. If applicable, compounds of formula (I) comprise both the E and the Z isomers, and additionally the threo and erythro, and the optical isomers, any mixtures of these isomers, and the possible tautomeric forms.

Any of the compounds according to the invention can exist in one or more optical, geometric or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereomers and/or the optical isomers can be separated according to the methods which are known per se by a person ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by a person ordinary skilled in the art.

Depending on the nature of the substituents, the compounds of formula (I) can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium hydrogen sulfate and potassium hydrogen sulfate.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl groups having 1 to 20 carbon atoms), arylsulfonic acids or -disulfonic acids (aromatic groups, such as phenyl and naphthyl, which carry one or two sulfonic acid groups), alkylphosphonic acids (phosphonic acids having straight-chain or branched alkyl groups having 1 to 20 carbon atoms), arylphosphonic acids or -diphosphonic acids (aromatic radicals, such as phenyl and naphthyl, which carry one or two phosphonic acid groups), where the alkyl and aryl groups may carry further substituents, for example p-toluenesulfonic acid, salicylic acid, p-aminosalicylic acid, 2-phenoxybenzoic acid, 2-acetoxybenzoic acid, etc.

The term "locus thereof" includes soil, surroundings of plant or plant parts and equipment or tools used before, during or after sowing/planting a plant or a plant part.

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

In view of the above, the present invention provides a novel fungicidal composition comprising a mixture of component (1) and component (2), wherein component (1) is at least one compound of formula (I) or an agriculturally acceptable salt thereof;

Formula (I)

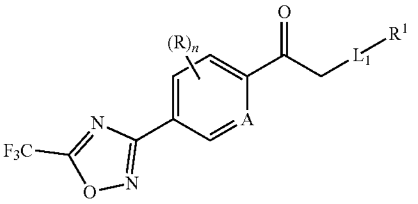

wherein;

A represents CR or N;

R is selected from the group consisting of hydrogen, halogen, $C_1$-$C_6$-alkyl, $C_1$-$C_6$-alkoxy, $C_1$-$C_6$-alkoxy-$C_1$-$C_4$-alkyl and $C_1$-$C_6$-haloalkyl;

$L^1$ represents —$NR^2$—, —O— or —$S(O)_{0-2}$—;

$R^1$ is selected from the group consisting of $C_1$-$C_6$-alkyl, $C_2$-$C_6$-alkenyl, $C_3$-$C_8$-cycloalkyl, $C_6$-$C_{10}$-aryl, $C_7$-$C_{14}$-aralkyl and $C_3$-$C_{10}$-heterocyclyl; each group of $R^1$ may optionally be substituted with one or more groups of $R^{1a}$;

$R^{1a}$ is selected from the group consisting of halogen, cyano, nitro, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxy, $C_1$-$C_6$-haloalkoxy, $C_1$-$C_6$-alkoxy-$C_1$-$C_4$-alkyl, $C_1$-$C_6$-hydroxyalkyl, $C_2$-$C_6$-haloalkenyl, $C_2$-$C_6$-haloalkynyl and $C_3$-$C_8$-halocycloalkyl;

$R^2$ is selected from the group consisting of hydrogen and $C_1$-$C_6$-alkyl; or $R^1$ and $R^2$ together with the atoms to which they are attached may form a 3- to 8-membered heterocyclic ring or ring system, wherein the heteroatom is selected from the group consisting of N, O and $S(O)_{0-2}$, wherein the heterocyclic ring or ring system may be optionally substituted with halogen, $C_1$-$C_6$-alkyl, $C_1$-$C_6$-haloalkyl or $C_1$-$C_6$-alkoxy;

n represents integers 0 to 2;

and component (2) is at least one further active compound selected from the following groups:

(A) Respiration Inhibitors
(B) Sterol Biosynthesis Inhibitors (SBI Fungicides)
(C) Nucleic acid synthesis inhibitors
(D) Inhibitors of cell division and cytoskeleton
(E) Inhibitors of amino acid and protein synthesis
(F) Signal transduction inhibitors
(G) Lipid and membrane synthesis inhibitors
(H) Inhibitors with Multi Site Action
(I) Cell wall synthesis inhibitors of glucan synthesis
(J) Plant defence inducers
(K) Unknown mode of action
(L) Insecticides.

In a preferred embodiment, the compound of formula (I) is selected from

Formula (I)

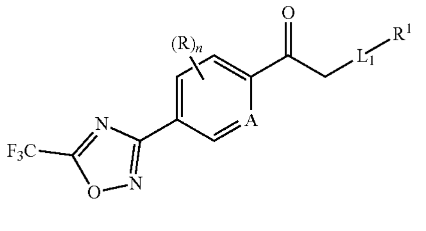

wherein;

A represents $CH_2$;

$L^1$ represents —$NR^2$— or —O—;

$R^1$ is selected from the group consisting of $C_6$-$C_{10}$-aryl, $C_7$-$C_{14}$-aralkyl and $C_3$-$C_{10}$-heterocyclyl; each group of $R^1$ may optionally be substituted with one or more groups of $R^{1a}$;

$R^{1a}$ is selected from the group consisting of halogen, cyano, nitro, hydroxy, $C_1$-$C_6$-alkyl, $C_1$-$C_6$-haloalkyl and $C_1$-$C_6$-alkoxy;

$R^2$ is selected from the group consisting of hydrogen and $C_1$-$C_6$-alkyl;

n represents integer 0.

In another preferred embodiment, the compound of formula (I) is selected from

Formula (I)

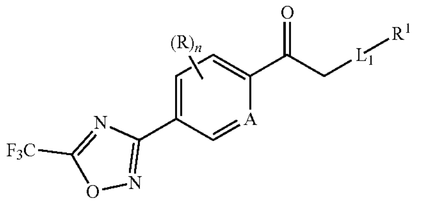

wherein;

A represents $CH_2$;

$L^1$ represents —$NR^2$— or —O—;

$R^1$ is selected from the group consisting of phenyl and pyridinyl; each group of $R^1$ may optionally be substituted with one or more groups of $R^{1a}$;

$R^{1a}$ is selected from the group consisting of halogen, cyano, nitro, hydroxy, $C_1$-$C_6$-alkyl, $C_1$-$C_6$-haloalkyl and $C_1$-$C_6$-alkoxy;

$R^2$ is selected from the group consisting of hydrogen and $C_1$-$C_6$-alkyl;

n represents integer 0.

In more preferred embodiment, the compound of formula (I) is selected from 2-(3-fluorophenoxy)-1-(4-(5-(trifluoromethyl)-1,2,4-oxadiazol-3-yl)phenyl)ethan-1-one (I-1), 2-(4-fluorophenoxy)-1-(4-(5-(trifluoromethyl)-1,2,4-oxadiazol-3-yl)phenyl)ethan-1-one (I-2), 2-((6-fluoropyridin-3-yl)oxy)-1-(4-(5-(trifluoromethyl)-1,2,4-oxadiazol-3-yl)phenyl)ethan-1-one (I-3), 2-(thiazol-2-ylsulfonyl)-1-(4-(5-(trifluoromethyl)-1,2,4-oxadiazol-3-yl)phenyl)ethan-1-one (I-4), 2-((3-fluorophenyl)amino)-1-(4-(5-(trifluoromethyl)-1,2,4-oxadiazol-3-yl)phenyl)ethan-1-one (I-5), 2-(benzylthio)-1-(5-(5-(trifluoromethyl)-1,2,4-oxadiazol-3-yl)pyridin-2-yl)ethan-1-one (I-6), 2-((3-fluorophenyl)sulfinyl)-1-(5-(5-(trifluoromethyl)-1,2,4-oxadiazol-3-yl)pyridin-2-yl)ethan-1-one (I-7), and 2-((4-fluorophenyl)amino)-1-(4-(5-(trifluoromethyl)-1,2,4-oxadiazol-3-yl)phenyl)ethan-1-one (I-8).

The compounds of formula (I) and their preparation and their use as fungicidally active compounds have been described in WO2020208511. The compounds of formula (I) can be prepared by using various routes as described in WO2020208511 and references therein or by the synthesis routes comprising at least one of the following schemes (1) to (2) as shown below in which, unless otherwise stated, the definition of each variable selected from R, $R^1$, $R^2$, A, $L_1$ and n is as defined above for a compound of formula (I).

Scheme: 1
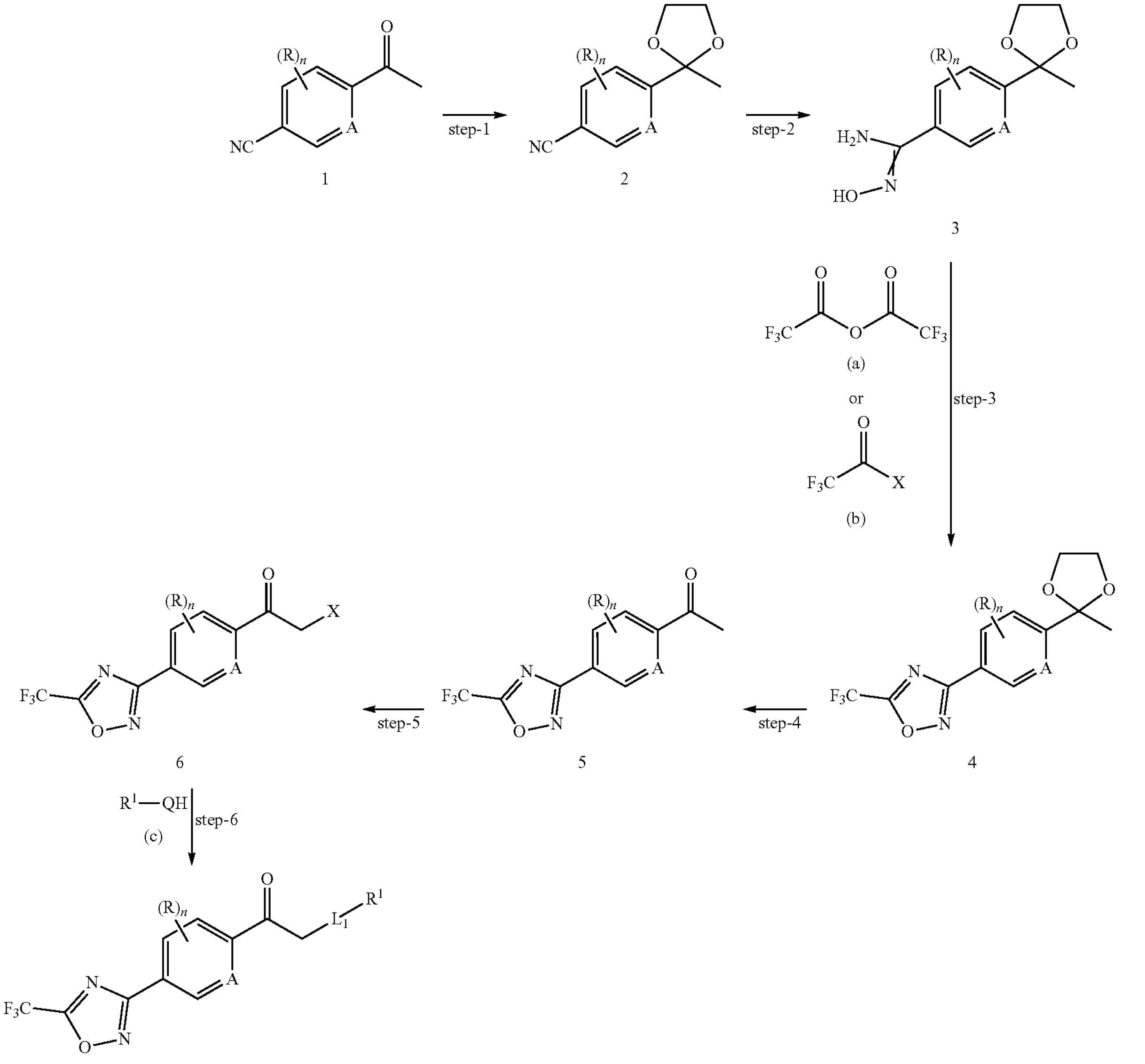
Formula I
wherein, $L_1$ is O, S, $NR^2$; X is Br, Cl or I and A, R, $R^1$ is having the same meaning as defined in the detailed description.
Step: 1
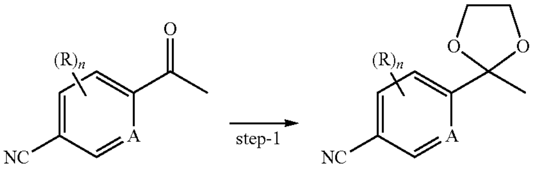
1 2
The compound of formula 2 can be prepared by protection of the carbonyl compound of formula 1 with ethylene glycol in the presence of N-bromosuccinimide and trimethyl orthoformate at an ambient to refluxing temperature.
Step: 2
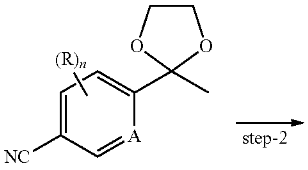
2

-continued

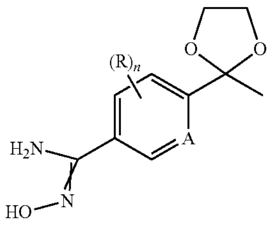

3

The compound of formula 3 can be prepared by reacting a nitrile compound of formula 2 with an aqueous hydroxyl amine solution in the presence of a suitable polar protic solvent such as ethanol, methanol and the like. Alternatively, this reaction can also be carried out by using hydroxylamine hydrochloride in the presence of a suitable organic/inorganic base such as triethylamine, diisopropyl amine, sodium bicarbonate, etc.

Step: 3

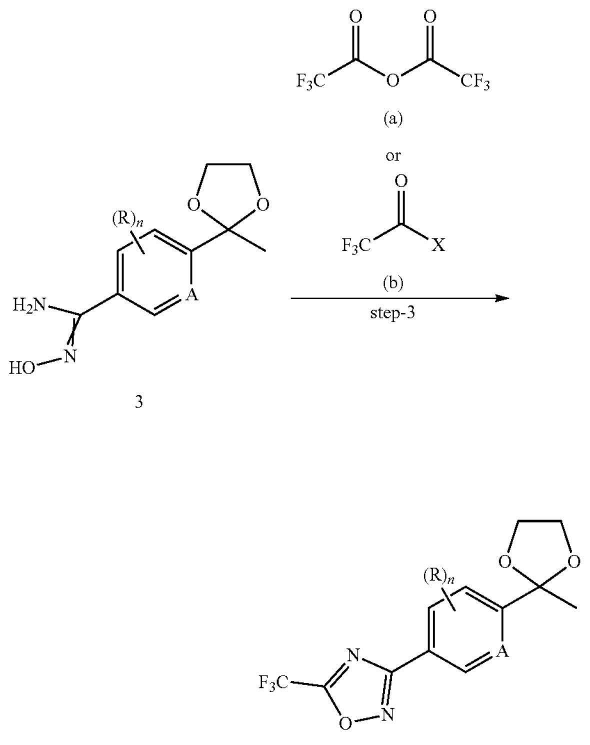

(a)
or
(b)
3
4

The compound of formula 4 can be obtained by reacting a compound of formula 3 and a carboxylic acid anhydride of formula (a). Alternatively, a compound of formula 4 can also be prepared by reacting with a carboxylic acid chloride of formula (b). These reactions are typically performed in a suitable aprotic solvent such as tetrahydrofuran, 1,4-dioxane, dichloromethane and the like, optionally in the presence of a suitable base such as triethylamine, diisopropyl amine, etc. at a temperature ranging from 0 to 50° C.

Step: 4

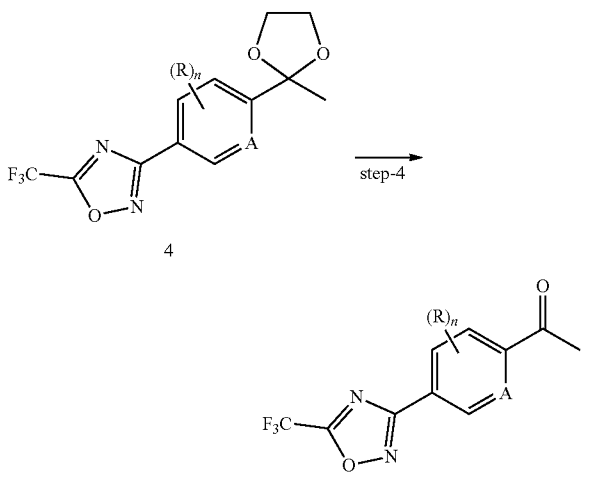

4
5

The compound of formula 5 can be obtained by deprotecting a ketal compound of formula 4 in the presence of a suitable deprotecting agent such as catalytic iodine or acid, and in a suitable solvent such as acetone. Typically, this reaction is carried out at a temperature ranging from 0 to 30° C.

Step: 5

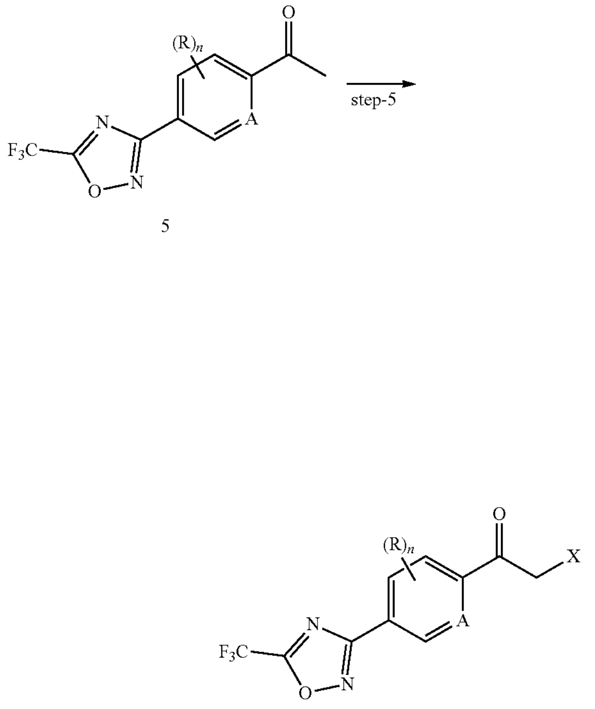

5
6

The compound of formula 6 can be obtained by alpha halogenation of a carbonyl compound 5 by using a suitable halogenating agent such as bromine, N-bromosuccinimide, N-chlorosuccinimide and the like. This reaction is typically performed in a suitable solvent such as dichloromethane at a temperature ranging from 0 to 30° C.

Step: 6

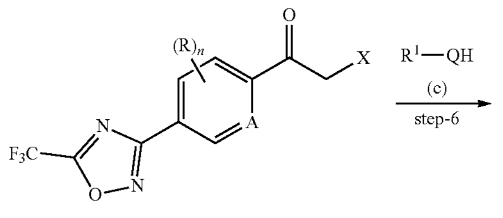

6

-continued

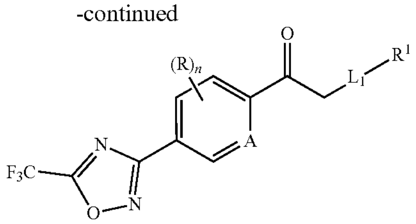

Formula (I)

The compound of formula (I) can be prepared by reacting an alpha-halo compound of formula 6 with the compound of formula $R^1$-QH wherein Q is O, S or $NR^2$ in the presence of a suitable inorganic base such as potassium carbonate, sodium bicarbonate and in the presence of a suitable solvent such as acetonitrile, dimethylformamide, ethanol and the like. This reaction can be performed at a temperature ranging from 0 to 25° C. and optionally in the presence of potassium iodide, sodium iodide and the like.

Scheme: 2

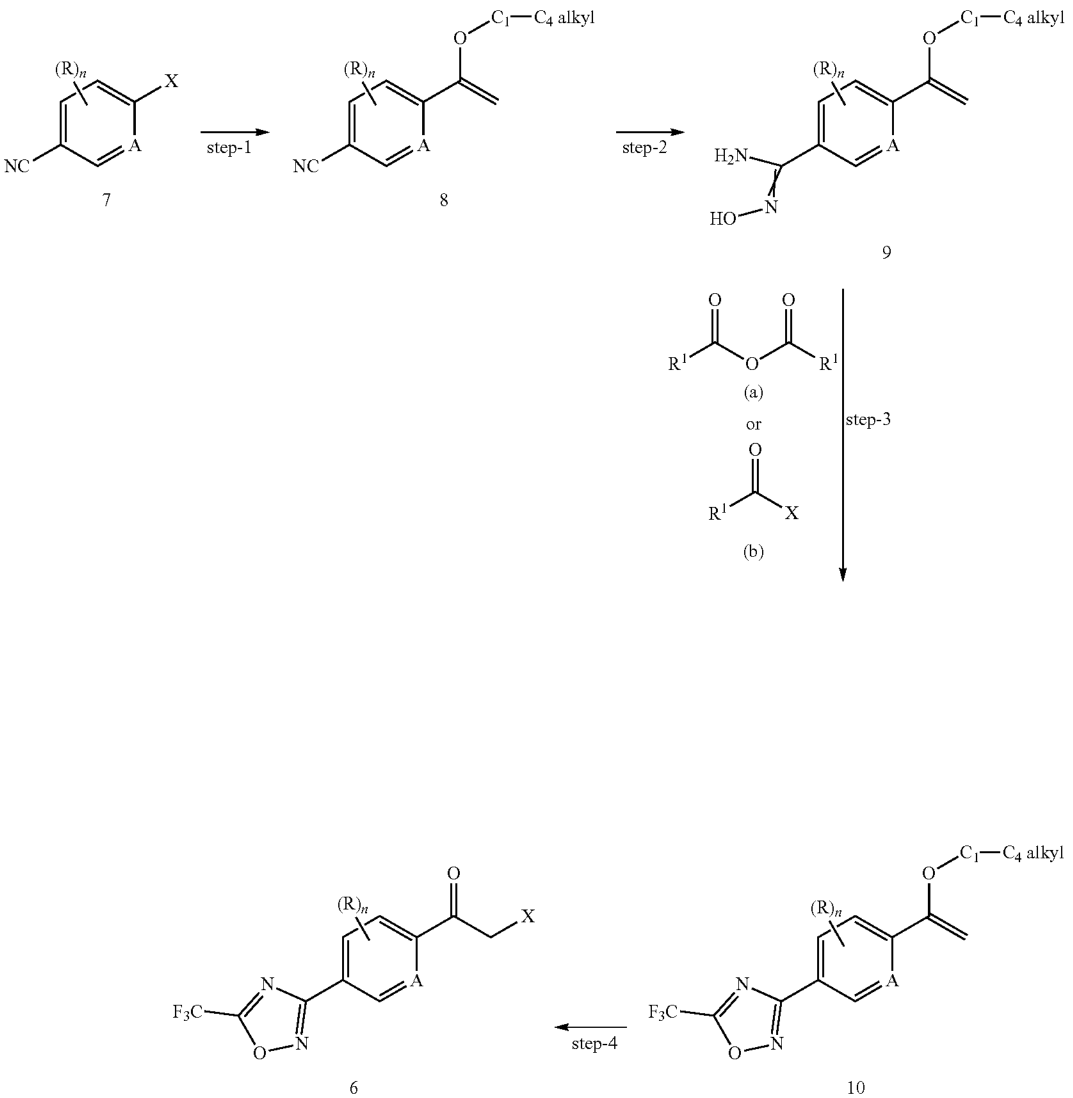

7 8 9 10 6 wherein, X is Br, $C_1$ or I; A and R is having the same meaning as defined in the detailed description, provided R is not halogen.

Step: 1

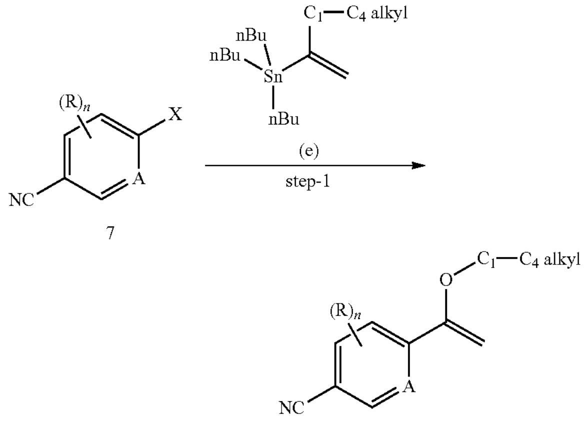

7
8

The compound of formula 8 can be obtained by reacting a compound of formula 7 with an organo stannane compound of formula (e) in the presence of a suitable palladium (II) reagent such as bis(triphenylphosphine)palladium(II) dichloride. This reaction is typically carried out in a suitable solvent such as toluene at a temperature ranging from 50 to 80° C.

Step: 2

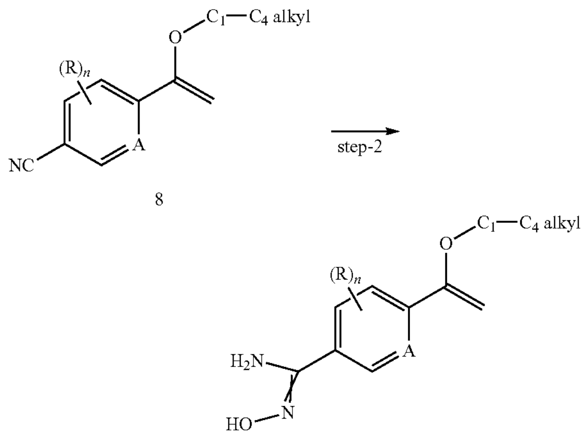

8
9

The compound of formula 9 can be prepared by reacting a nitrile compound of formula 8 with a hydroxyl amine in a suitable polar protic solvent such as ethanol, methanol and the like. Alternatively, this reaction can also be carried out by using hydroxylamine hydrochloride in the presence of a suitable organic and inorganic base such as triethylamine, diisopropyl amine, sodium bicarbonate and the like.

Step: 3

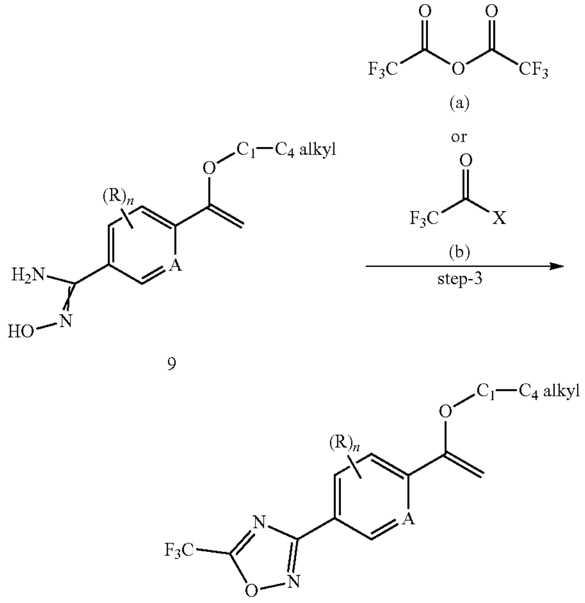

9
10

The compound of formula 10 can be obtained by reacting a compound of formula 9 with a carboxylic acid anhydride of formula (a). Alternatively, the compound of formula 10 can also be prepared by reacting a compound of formula 9 with a carboxylic acid chloride of formula (b). These reactions are typically performed in a suitable aprotic solvent such as tetrahydrofuran, 1,4-dioxane, dichloromethane and the like, and optionally in the presence of a suitable base such as triethylamine, diisopropyl amine and the like at a temperature ranging from 0 to 50° C.

Step: 4

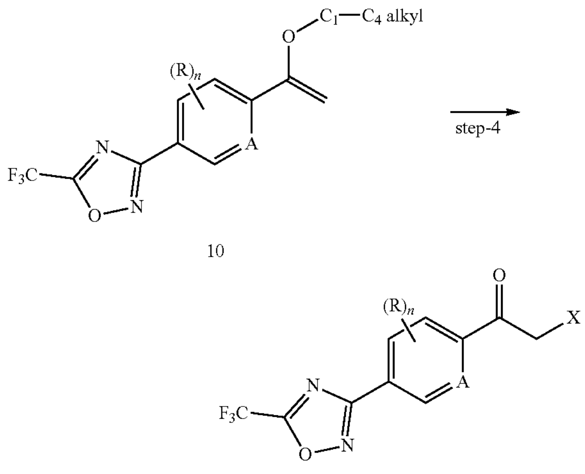

10
6

The compound of formula 6 can be obtained by reacting the compound of formula 10 with a suitable halogenating reagent such as N-bromosuccinimide in the presence of water. This reaction is typically performed in a suitable solvent such as tetrahydrofuran at a temperature ranging from 0 to 25° C.

In another preferred embodiment, the component (2) is selected from the following groups (A) to (L):

A) Respiration Inhibitors:

Inhibitors of complex III at $Q_o$ site: azoxystrobin (A001), coumethoxystrobin (A002), coumoxystrobin (A003), dimoxystrobin (A004), enostroburin (A005), fenaminstrobin (A006), flufenoxystrobin (A007), fluoxastrobin (A008), kresoxim-methyl (A009), mandestrobin (A010), metominostrobin (A011), orysastrobin (A012), picoxystrobin (A013), pyraclostrobin (A014), pyrametostrobin (A015), pyraoxystrobin (A016), trifloxystrobin (A017), 2-(2-(3-(2,6-dichlorophenyl)-1-methyl-allylideneaminooxymethyl)-phenyl)-2-methoxyimino-N-methyl-acetamide (A018), pyribencarb (A019), triclopyricarb/chlorodincarb (A020), famoxadone (A021), fenamidone (A021a), methyl-N-[2-[(1,4-dimethyl-5-phenyl-pyrazol-3-yl)oxymethyl]phenyl]-N-methoxy-carbamate (A022), 1-[3-chloro-2-[[1-(4-chlorophenyl)-1H-pyrazol-3-yl]oxymethyl]phenyl]-4-methyl-tetrazol-5-one (A023), 1-[3-bromo-2-[[1-(4-chlorophenyl)pyrazol-3-yl]oxymethyl]phenyl]-4-methyl-tetrazol-5-one (A024), metyltetraprole (A025), 1-[[2-[1-(4-chlorophenyl)pyrazol-3-yl]oxymethyl]-3-fluoro-phenyl]-4-methyl-tetrazol-5-one (A026), 1-[2-[[1-(2,4-dichlorophenyl)pyrazol-3-yl]oxymethyl]-3-fluoro-phenyl]-4-methyl-tetrazol-5-one (A027), 1-[2-[[4-(4-chlorophenyl)thiazol-2-yl]oxymethyl]-3-methyl-phenyl]-4-methyl-tetrazol-5-one (A028), 1-[3-chloro-2-[[4-(p-tolyl)thiazol-2-yl]oxymethyl]phenyl]-4-methyl-tetrazol-5-one (A029), 1-[3-cyclopropyl-2-[[2-methyl-4-(1-methylpyrazol-3-yl)phenoxy]-methyl]phenyl]-4-methyl-tetrazol-5-one (A030), 1-[3-(difluoromethoxy)-2-[[2-methyl-4-(1-methylpyrazol-3-yl)phenoxy]methyl]phenyl]-4-methyl-tetrazol-5-one (A031), 1-methyl-4-[3-methyl-2-[[2-methyl-4-(1-methylpyrazol-3-yl)phenoxy]methyl]phenyl]tetrazol-5-one (A032), 1-methyl-4-[3-methyl-2-[[1-[3-(trifluoromethyl)phenyl]-ethylideneamino]oxymethyl]phenyl]tetrazol-5-one (A033), (Z,2E)-5-[1-(2,4-dichlorophenyl)pyrazol-3-yl]-oxy-2-methoxyimino-N-3-dimethyl-pent-3-enamide (A034), (Z,2E)-5-[1-(4-chlorophenyl)pyrazol-3-yl]oxy-2-methoxyimino-N-3-dimethyl-pent-3-enamide (A035), pyriminostrobin (A036), bifujunzhi (A037), 2-(ortho-((2,5-dimethylphenyl-oxymethylen)phenyl)-3-methoxy-acrylic acid methylester (A038);

Inhibitors of complex III at Qi site: cyazofamid (A039), amisulbrom (A040), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A041), fenpicoxamid (A042), [(6S,7R,8R)-8-benzyl-3-[[4-methoxy-3-(propanoyloxymethoxy)pyridine-2-carbonyl]amino]-6-methyl-4,9-dioxo-1,5-dioxonan-7-yl]-2-methylpropanoate (A043), florylpicoxamid (A044), metarylpicoxamid (A045);

Inhibitors of complex II: benodanil (A046), benzovindiflupyr (A047), bixafen (A048), boscalid (A049), carboxin (A050), cyclobutrifluram (A051), fenfuram (A052), fluopyram (A053), flubeneteram (A054), flufenoxadiazam (A055), flutolanil (A056), fluxapyroxad (A057), furametpyr (A058), fluindapyr (A059), isopyrazam (A060), isofetamid (A061), isoflucypram (A062), inpyrfluxam (A063), mepronil (A064), oxycarboxin (A065), pyrapropoyne (A066), penflufen (A067), penthiopyrad (A068), pydiflumetofen (A069), N-[2-(3,4-difluorophenyl)phenyl]-3-(trifluoromethyl)pyrazine-2-carboxamide (A070), sedaxane (A071), tecloftalam (A072), thifluzamide (A073), 3-(difluoromethyl)-1-methyl-N-(1,1,3-trimethyl-indan-4-yl)pyrazole-4-carboxamide (A074), 3-(trifluoromethyl)-1-methyl-N-(1,1,3-trimethyl-indan-4-yl)pyrazole-4-carboxamide (A075), 1,3-dimethyl-N-(1,1,3-trimethylindan-4-yl)pyrazole-4-carboxamide (A076), 3-(trifluoromethyl)-1,5-dimethyl-N-(1,1,3-trimethylindan-4-yl)pyrazole-4-carboxamide (A077), 1,3,5-trimethyl-N-(1,1,3-trimethyl-indan-4-yl)pyrazole-4-carboxamide (A078), 3-(difluoromethyl)-1,5-dimethyl-N-(1,1,3-trimethyl-indan-4-yl)pyrazole-4-carboxamide (A079), 3-(difluoromethyl)-N-(7-fluoro-1,1,3-trimethyl-indan-4-yl)-1-methyl-pyrazole-4-carboxamide (A080), N-[2-[2-chloro-4-(trifluoromethyl)phenoxy]phenyl]-3-(difluoromethyl)-5-fluoro-1-methyl-pyrazole-4-carboxamide (A081), methyl (E)-2-[2-[(5-cyano-2-methyl-phenoxy)methyl]phenyl]-3-methoxy-prop-2-enoate (A082), N-[(5-chloro-2-isopropyl-phenyl)methyl]-N-cyclopropyl-3-(difluoromethyl)-5-fluoro-1-methyl-pyrazole-4-carboxamide (A083), 2-(difluoromethyl)-N-(1,1,3-trimethyl-indan-4-yl)pyridine-3-carboxamide (A084), 2-(difluoromethyl)-N-[(3R)-1,1,3-trimethyl-indan-4-yl]pyridine-3-carboxamide (A085), 2-(difluoromethyl)-N-[(3S)3-ethyl-1,1-dimethyl-indan-4-yl]pyridine-3-carboxamide (A086), 2-(difluoromethyl)-N-[(3R)-3-ethyl-1,1-dimethyl-indan-4-yl]pyridine-3-carboxamide (A087), 2-(difluoromethyl)-N-(1,1-dimethyl-3-propyl-indan-4-yl)pyridine-3-carboxamide (A088), 2-(difluoromethyl)-N-[(3R)-1,1-dimethyl-3-propyl-indan-4-yl]pyridine-3-carboxamide (A089), 2-(difluoromethyl)-N-(3-isobutyl-1,1-dimethyl-indan-4-yl)pyridine-3-carboxamide (A090), 2-(difluoromethyl)-N-[(3R)-3-isobutyl-1,1-dimethyl-indan-4 yl]pyridine-3-carboxamide (A091);

Other respiration inhibitors: diflumetorim (A092), flumetylsulforim (A093); nitrophenyl derivates: binapacryl (A094), dinobuton (A095), dinocap (A096), fluazinam (A097), meptyldinocap (A098), ferimzone (A099); organometal compounds: fentin salts, e.g. fentin-acetate (A100), fentin chloride (A101) or fentin hydroxide (A102); ametoctradin (A103); silthiofam (A104);

B) Sterol Biosynthesis Inhibitors (SBI Fungicides)

$C_{14}$ demethylase inhibitors: triazoles: azaconazole (B001), bitertanol (B002), bromuconazole (B003), cyproconazole (B004), difenoconazole (B005), diniconazole (B006), diniconazole-M (B007), epoxiconazole (B008), fluoxytioconazole (B009), fenbuconazole (B010), fluquinconazole (B011), flusilazole (B012), flutriafol (B013), hexaconazole (B014), imibenconazole (B015), ipconazole (B016), metconazole (B017), myclobutanil (B018), oxpoconazole (B019), paclobutrazole (B020), penconazole (B021), propiconazole (B022), prothioconazole (B023), simeconazole (B024), tebuconazole (B025), tetraconazole (B026), triadimefon (B027), triadimenol (B028), triticonazole (B029), uniconazole (B030), 1-[rel-(2,3R)-3-(2-chloro-phenyl)-2-(2,4-difluorophenyl)-oxiranylmethyl]-5-thiocyanato-1H-[1,2,4]triazole (B031), 2-[rel-(2S,3R)-3-(2-chlorophenyl)-2-(2,4-difluorophenyl)-oxiranylmethyl]-2H-[1,2,4]triazole-3-thiol (B032), 2-[2-chloro-4-(4-chlorophenoxy)phenyl]-1-(1,2,4-triazol-1-yl)pentan-2-ol (B033), 1-[4-(4-chlorophenoxy)-

2-(trifluoromethyl)phenyl]-1-cyclopropyl-2-(1,2,4-triazol-1-yl)ethanol (B034), 2-[4-(4-chlorophenoxy)-2-(trifluoromethyl)phenyl]-1-(1,2,4-triazol-1-yl)butan-2-ol (B035), 2-[2-chloro-4-(4-chlorophenoxy)phenyl]-1-(1,2,4-triazol-1-yl)butan-2-ol (B036), ipfentrifluconazole (B037), mefentrifluconazole (B038), 2-[2-chloro-4-(4-chlorophenoxy)phenyl]-3-methyl-1-(1,2,4-triazol-1-yl)butan-2-ol (B039), 2-[4-(4-chlorophenoxy)-2-(trifluoromethyl)phenyl]-1-(1,2,4-triazol-1-yl)pentan-2-ol (B040), 2-[4-(4-fluorophenoxy)-2-(trifluoromethyl)phenyl]-1-(1,2,4-triazol-1-yl)propan-2-ol (B041), 2-[2-chloro-4-(4-chlorophenoxy)phenyl]-1-(1,2,4-triazol-1-yl)pent-3-yn-2-ol (B042), 2-(chloromethyl)-2-methyl-5-(p-tolylmethyl)-1-(1,2,4-triazol-1-ylmethyl)cyclopentanol (B043); imidazoles: imazalil (B044), imazalil sulfate (B045), pefurazoate (B046), prochloraz (B047), triflumizol (B048); pyrimidines, pyridines and piperazines: fenarimol (B049), pyrifenox (B050), triforine (B051), [3-(4-chloro-2-fluoro-phenyl)-5-(2,4-difluorophenyl)isoxazol-4-yl]-(3-pyridyl)methanol (B052);

Delta14-reductase inhibitors: aldimorph (B053), dodemorph (B054), dodemorph-acetate (B055), fenpropimorph (B056), tridemorph (B057), fenpropidin (B058), piperalin (B059), spiroxamine (B060);

Inhibitors of 3-keto reductase: fenhexamid (B061);

Other Sterol biosynthesis inhibitors: chlorphenomizole (B062);

C) Nucleic Acid Synthesis Inhibitors

Phenylamides or acyl amino acid fungicides: benalaxyl (C001), benalaxyl-M (C002), kiralaxyl (C003), metalaxyl (C004), metalaxyl-M (C005), ofurace (C006), oxadixyl (C007);

Other nucleic acid synthesis inhibitors: hymexazole (C008), octhilinone (C009), oxolinic acid ($C_{010}$), bupirimate ($C_{011}$), 5-fluorocytosine ($C_{012}$), 5-fluoro-2-(p-tolylmethoxy)pyrimidin-4-amine ($C_{013}$), 5-fluoro-2-(4-fluorophenylmethoxy)pyrimidin-4-amine ($C_{014}$), 5-fluoro-2-(4-chlorophenylmethoxy)pyrimidin-4 amine ($C_{015}$);

D) Inhibitors of Cell Division and Cytoskeleton

Tubulin inhibitors: benomyl (D001), carbendazim (D002), fuberidazole (D003), thiabendazole (D004), thiophanate-methyl (D005), 3-chloro-4-(2,6-difluorophenyl)-6-methyl-5-phenyl-pyridazine (D006), 3-chloro-6-methyl-5-phenyl-4-(2,4,6-trifluorophenyl)pyridazine (D007), N-ethyl-2-[(3-ethynyl-8-methyl-6-quinolyl)oxy]butanamide (D008), N-ethyl-2-[(3-ethynyl-8-methyl-6-quinolyl)oxy]-2-methylsulfanyl-acetamide (D009), 2-[(3-ethynyl-8-methyl-6-quinolyl)oxy]-N-(2-fluoroethyl)butanamide (D010), 2-[(3-ethynyl-8-methyl-6-quinolyl)oxy]-N-(2-fluoroethyl)-2-methoxy-acetamide (D011), 2-[(3-ethynyl-8-methyl-6-quinolyl)oxy]-N-propyl-butanamide (D012), 2-[(3-ethynyl-8-methyl-6-quinolyl)oxy]-2-methoxy-N-propyl-acetamide (D013), 2-[(3-ethynyl-8-methyl-6-quinolyl)oxy]-2-methylsulfanyl-N-propyl-acetamide (D014), 2-[(3-ethynyl-8-methyl-6-quinolyl)oxy]-N-(2-fluoroethyl)-2-methylsulfanyl-acetamide (D015), 4-(2-bromo-4-fluoro-phenyl)-N-(2-chloro-6-fluoro-phenyl)-2,5-dimethyl-pyrazol-3-amine (D016);

Other cell division inhibitors: diethofencarb (D017), ethaboxam (D018), pencycuron (D019), fluopicolide (D020), zoxamide (D021), metrafenone (D022), pyriofenone (D023);

E) Inhibitors of Amino Acid and Protein Synthesis

Methionine synthesis inhibitors: cyprodinil (E001), mepanipyrim (E002), pyrimethanil (E003);

Protein synthesis inhibitors: blasticidin-S (E004), kasugamycin (E005), kasugamycin hydrochloride-hydrate (E006), mildiomycin (E007), streptomycin (E008), oxytetracyclin (E009);

F) Signal Transduction Inhibitors

MAP/histidine kinase inhibitors: fluoroimid (F001), iprodione (F002), procymidone (F003), vinclozolin (F004), fludioxonil (F005);

G protein inhibitors: quinoxyfen (F006), aminopyrifen (F007);

G) Lipid and Membrane Synthesis Inhibitors

Phospholipid biosynthesis inhibitors: edifenphos (G001), iprobenfos (G002), pyrazophos (G003), isoprothiolane (G004);

Lipid peroxidation: dicloran (G005), quintozene (G006), tecnazene (G007), tolclofos-methyl (G008), biphenyl (G009), chloroneb (G010), etridiazole (G011);

Phospholipid biosynthesis and cell wall deposition: dimethomorph (G012), flumorph (G013), mandipropamid (G014), pyrimorph (G015), benthiavalicarb (G016), iprovalicarb (G017), valifenalate (G018);

Compounds affecting cell membrane permeability and fatty acids: propamocarb (G019);

Inhibitors of oxysterol binding protein: oxathiapiprolin (G020), fluoxapiprolin (G021), 2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)phenyl methanesulfonate (G022), 2-{3-[2-(1-{[3,5-bis(difluoromethyl)-1H-pyrazol-1-yl]-acetyl} piperidin-4-yl) 1,3-thiazol-4-yl]-4,5-dihydro-1,2-oxazol-5-yl}-3-chlorophenyl methane-sulfonate (G023), 4-[1-[2-[3-(difluoromethyl)-5-methyl-pyrazol-1-yl]acetyl]-4-piperidyl]-N-tetralin-1-yl-pyridine-2-carboxamide (G024), 4-[1-[2-[3,5-bis(difluoromethyl)pyrazol-1-yl]acetyl]-4-piperidyl]-N-tetralin-1-yl-pyridine-2-carboxamide (G025), 4-[1-[2-[3-(difluoromethyl)-5-(tri-fluoromethyl)pyrazol-1-yl]acetyl]-4-piperidyl]-N-tetralin-1-yl-pyridine-2-carboxamide (G026), 4-[1-[2-[5-cyclopropyl-3-(difluoromethyl)pyrazol-1-yl]acetyl]-4-piperidyl]-N-tetralin-1-yl-pyridine-2-carboxamide (G027), 4-[1-[2-[5-methyl-3-(trifluoromethyl)pyrazol-1-yl]acetyl]-4-piperidyl]-N-tetralin-1-yl-pyridine-2-carboxamide (G028), 4-[1-[2-[5-(difluoromethyl)-3-(trifluoro-methyl)pyrazol-1-yl]acetyl]-4-piperidyl]-N-tetralin-1-yl-pyridine-2-carboxamide (G029), 4-[1-[2-[3,5-bis(trifluoromethyl)pyrazol-1-yl]acetyl]-4-piperidyl]-N-tetralin-1-yl-pyridine-2-carboxamide (G030), (4-[1-[2-[5-cyclopropyl-3-(trifluoromethyl)pyrazol-1-yl]acetyl]-4-piperidyl]-N-tetralin-1-yl-pyridine-2-carboxamide (G031);

H) Inhibitors with Multi Site Action

Inorganic active substances: Bordeaux mixture (H001), copper (H002), copper acetate (H003), copper hydroxide (H004), copper oxychloride (H005), basic copper sulfate (H006), sulfur (H007);

Thio- and dithiocarbamates: ferbam (H008), mancozeb (H009), maneb (H010), metam (H011), metiram (H012), propineb (H013), thiram (H014), zineb (H015), ziram (H016);

Organochlorine compounds: anilazine (H017), chlorothalonil (H018), captafol (H019), captan (H020), folpet (H021), dichlofluanid (H022), dichlorophen (H023), hexachlorobenzene (H024), pentachlorphenole (H025) and its salts, phthalide (H026), tolylfluanid (H027);

Guanidines and others: guanidine (H028), dodine (H029), dodine free base (H030), guazatine (H031), guazatine-acetate (H032), iminoctadine (H033), iminoctadine-triacetate (H034), iminoctadine-tris(albesilate) (H035), dithianon (H036), 2,6-dimethyl-1H,5H-[1,4]dithiino[2,3-c:5,6-c']dipyrrole-1,3,5,7(2H,6H)-tetraone (H037);

I) Cell Wall Synthesis Inhibitors

Inhibitors of glucan synthesis: validamycin (1001), polyoxin B (I002);

Melanin synthesis inhibitors: pyroquilon (1003), tricyclazole (1004), carpropamid (1005), dicyclomet (1006), fenoxanil (1007);

J) Plant Defence Inducers

Acibenzolar-S-methyl (J001), probenazole (J002), isotianil (J003), tiadinil (J004), prohexadione-calcium (J005); phosphonates: fosetyl (J006), fosetyl-aluminum (J007), phosphorous acid and its salts (J008), potassium or sodium bicarbonate (J009), 4-cyclopropyl-N-(2,4-dimethoxyphenyl)thiadiazole-5-carboxamide (J010), calcium phosphonate (J011), potassium phosphonate (J012);

K) Unknown Mode of Action

Bronopol (K001), chinomethionat (K002), cyflufenamid (K003), cymoxanil (K004), chloroinconazide (K005), dazomet (K006), debacarb (K007), diclocymet (K008), diclomezine (K009), difenzoquat (K010), difenzoquat-methylsulfate (K011), diphenylamin (K012), fenitropan (K013), fenpyrazamine (K014), flumetover (K015), flusulfamide (K016), flutianil (K017), harpin (K018), ipflufenoquin (K019), methasulfocarb (K020), nitrapyrin (K021), nitrothal-isopropyl (K022), oxincopper (K023), proquinazid (K024), pyridachlometyl (K025), tebufloquin (K026), tolprocarb (K027), triazoxide (K028), N'-(4-(4-chloro-3-trifluoromethyl-phenoxy)-2,5-dimethyl-phenyl)-N-ethyl-N-methyl formamidine (K029), N'-(4-(4-fluoro-3-trifluoromethyl-phenoxy)-2,5-dimethyl-phenyl)-N-ethyl-N-methyl formamidine (K030), N'-[4-[[3-[(4-chorophenyl) methyl]-1,2,4-thiadiazo-5-yl]oxy]-2,5-dimethyl-phenyl]-N-ethyl-N-methyl-formamidine (K031), N'-(5-bromo-6-indan-2-yloxy-2-methyl-3-pyridyl)-N-ethyl-N-methyl-formamidine (K032), N'-[5-bromo-6-[1-(3,5-difluorophenyl)ethoxy]-2-methyl-3-pyridyl]-N-ethyl-N-methyl-formamidine (K033), N'-[5-bromo-6-(4-isopropylcyclohexoxy)-2-methyl-3-pyridyl]-N-ethyl-N-methyl-formamidine (K034), N'-[5-bromo-2-methyl-6-(1-phenylethoxy)-3-pyridyl]-N-ethyl-N-methyl-formamidine (K035), N'-(2-methyl-5-trifluoromethyl-4-(3-trimethylsilanyl-propoxy)-phenyl)-N-ethyl-N-methyl-formamidine (K036), N'-(5-difluoromethyl-2-methyl-4-(3-trimethylsianyl-propoxy)-phenyl)-N-ethyl-N-methyl-formamidine (K037), 2-(4-chloro-phenyl)-N-[4-(3,4-dimethoxy-phenyl)-isoxazol-5-yl]-2-prop-2-ynyloxy-acetamide (K038), 3-[5-(4-chloro-phenyl)-2,3-dimethyl-isoxazolidin-3-yl]-pyridine (pyrisoxazole) (K039), 3-[5-(4-methylphenyl)-2,3-dimethyl-isoxazolidin-3 yl]-pyridine (K040), 5-chloro-1-(4,6-dimethoxy-pyrimidin-2-yl)-2-methyl-1H-benzoimidazole (K041), ethyl (Z)-3-amino-2-cyano-3-phenyl-prop-2-enoate (K042), picarbutrazox (K043), pentyl N-[6-[[(Z)-[(1-methyltetrazol-5-yl)-phenyl-methylene]amino]oxymethyl]-2-pyridyl]carbamate (K044), but-3-ynyl N-[6-[[(Z)-[(1-methyltetrazol-5-yl)-phenyl-methylene]amino] oxymethyl]-2-pyridyl]carbamate (K045), 2-[2-[(7,8-difluoro-2-methyl-3-quinolyl)oxy]-6-fluoro-phenyl] propan-2-ol (K046), 2-[2-fluoro-6-[(8-fluoro-2-methyl-3-quinolyl)oxy]phenyl]propan-2-ol (K047), 3-(5-fluoro-3,3,4,4-tetramethyl-3,4-dihydroisoquinolin-1-yl)quinoline (K048), quinofumelin (K049), 3-(4,4,5-trifluoro-3,3-dimethyl-3,4-dihydroisoquinolin-1-yl)quinoline (K050), 9-fluoro-2,2-dimethyl-5-(3-quinolyl)-3H-1,4-benzoxazepine (K051), 2-(6-benzyl-2-pyridyl)quinazoline (K052), 2-[6-(3-fluoro-4-methoxy-phenyl)-5-methyl-2-pyridyl]quinazoline (K053), dichlobentiazox (K054), N'-(2,5-dimethyl-4-phenoxy-phenyl)-N-ethyl-N-methyl-formamidine (K055), N'-[5-bromo-2-methyl-6-(1-methyl-2-propoxy-ethoxy)-3-pyridyl]-N-ethyl-N-methyl-formamidine (K056), N'-(4-(3,5-difluorobenzyl)-2-methylphenyl)-N-ethyl-N-methylformimidamide (K057), N'-(4-benzyl-2-chloro-5-methylphenyl)-N-ethyl-N-methylformimidamide (K058), N'-(2,5-dimethyl-4-(2-methylbenzyl)phenyl)-N-ethyl-N-methylformimidamide (K059), N'-(5-chloro-2-methyl-3-(3-(K060), N-ethyl-N'-(3-(2-fluorobenzyl)-2,5-methylbenzyl)phenyl)-N-ethyl-N-methylformimidamide dimethylphenyl)-N-methylformimidamide (K061), N-ethyl-N'-(5-fluoro-2-methyl-3-(3-methylbenzyl)phenyl)-N-methylformimidamide (K062), N'-(4-(2-(2-bromo-4-methylphenoxy)acetyl)-2,5-dimethylphenyl)-N-ethyl-N-methylformimidamide (K063), and N'-(2-chloro-4-(2-(2-fluorophenoxy)acetyl)-5-methylphenyl)-N-ethyl-N-methylformimidamide (K064).

L) Insecticides from classes (a) to (z):

Acetylcholine esterase (AChE) inhibitors: aldicarb (L001), alanycarb (L002), bendiocarb (L003), benfuracarb (L004), butocarboxim (L005), butoxycarboxim (L006), carbaryl (L007), carbofuran (L008), carbosulfan (L009), ethiofencarb (L010), fenobucarb (L011), formetanate (L012), furathiocarb (L013), isoprocarb (L014), methiocarb (L015), methomyl (L016), metolcarb (L017), oxamyl (L018), pirimicarb (L019), propoxur (L020), thiodicarb (L021), thiofanox (L022), trimethacarb (L023), XMC (L024), xylylcarb (L025), triazamate (L026), acephate (L027), azamethiphos (L028), azinphos-ethyl (L029), azinphosmethyl (L030), cadusafos (L031), chlorethoxyfos (L032), chlorfenvinphos (L033), chlormephos (L034), chlorpyrifos (L035), chlorpyrifos-methyl (L036), coumaphos (L037), cyanophos (L038), demeton-S-methyl (L039), diazinon (L040), dichlorvos/DDVP (L041), dicrotophos (L042), dimethoate (L043), dimethylvinphos (L044), disulfoton (L045), EPN (L046), ethion (L047), ethoprophos (L048), famphur (L049), fenamiphos (L050), fenitrothion (L051), fenthion (L052), fosthiazate (L053), heptenophos (L054), imicyafos (L055), isofenphos (L056), isopropyl O-(methoxyaminothio-phosphoryl) salicylate (L057), isoxathion (L058), malathion (L059), mecarbam (L060), methamidophos (L061), methidathion (L062), mevinphos (L063), monocrotophos (L064), naled (L065), omethoate (L066), oxydemeton-methyl (L067), parathion (L068), parathion-methyl (L069), phenthoate (L070), phorate (L071), phosalone (L072), phosmet (L073), phosphamidon (L074), phoxim (L075), pirimiphos-methyl (L076), profenofos (L077), propetamphos (L078), prothiofos (L079), pyraclofos (L080), pyridaphenthion (L081), quinalphos (L082), sulfotep (L083), tebupirimfos (L084), temephos (L085), terbufos (L086), tetrachlorvinphos (L087), thiometon (L088), triazophos (L089), trichlorfon (L090), vamidothion (L091);

GABA-gated chloride channel antagonists: endosulfan (L092), chlordane (L093), ethiprole (L094), fipronil (L095), flufiprole (L096), pyrafluprole (L097) and pyriprole (L098);

Sodium channel modulators: acrinathrin (L099), allethrin (L100), d-cis-trans allethrin (L101), d-trans allethrin (L102), bifenthrin (L103), bioallethrin (L104), bioallethrin S-cylclopentenyl (L105), bioresmethrin (L106), cycloprothrin (L107), cyfluthrin (L108), beta-cyfluthrin (L109), cyhalothrin (L110), lambda-cyhalothrin (L111), gamma-cyhalothrin (L112), cypermethrin (L113), alpha-cypermethrin (L114), beta-cypermethrin (L115), theta-cypermethrin (L116), zeta-cypermethrin (L117), cyphenothrin (L118), deltamethrin (L119), empenthrin (L120), esfenvalerate (L121), etofenprox (L122), fenpropathrin (L123), fenvalerate (L124), flucythrinate (L125), flumethrin (L126), taufluvalinate (L127), halfenprox (L128), heptafluthrin (L129), imiprothrin (L130), meperfluthrin (L131), metofluthrin (L132), momfluorothrin (L133), permethrin (L134), phenothrin (L135), prallethrin (L136), profluthrin (L137), pyrethrin (pyrethrum) (L138), resmethrin (L139), silafluofen (L140), tefluthrin (L141), tetramethylfluthrin (L142), tetramethrin (L143), tralomethrin (L144), transfluthrin (L145), DDT (L146) and methoxychlor (L147);

Nicotinic acetylcholine receptor agonists (nAChR): acetamiprid (L148), clothianidin (L149), cycloxaprid (L150), dinotefuran (L151), imidacloprid (L152), nitenpyram (L153), thiacloprid (L154), thiamethoxam (L155), (2E)-1-[(6-chloropyridin-3-yl)methyl]-N'-nitro-2-pentylidenehydrazinecarboximidamide (L156), 1-[(6-chloropyridin-3-yl)methyl]-7-methyl-8-nitro-5-propoxy-1,2,3,5,6,7-hexahydroimidazo[1,2-a]pyridine (L157) and nicotine (L158);

Nicotinic acetylcholine receptor allosteric activators: spinosad (L159) and spinetoram (L160);

Chloride channel activators: abamectin (L161), emamectin benzoate (L162), ivermectin (L163), lepimectin (L164) and milbemectin (L165);

Juvenile hormone mimics: hydroprene (L166), kinoprene (L167), methoprene (L168), fenoxycarb (L169) and pyriproxyfen (L170);

Miscellaneous non-specific (multi-site) inhibitors: methyl bromide (L171) and other alkyl halides; chloropicrin (L172), sulfuryl fluoride (L173), borax (L174) and tartar emetic (L175);

Selective homopteran feeding blockers: pymetrozine (L176) and flonicamid (L177);

Mite growth inhibitors: clofentezine (L178), hexythiazox (L179), diflovidazin (L180) and etoxazole (L181);

Microbial disruptors of insect midgut membranes: the Bt crop proteins: Cry1 Ab (L182), Cry1Ac (L183), Cry1 Fa (L184), Cry2Ab (L185), mCry3A (L186), Cry3Ab (L187), Cry3Bb (L188) and Cry34/35Ab1 (L189);

Inhibitors of mitochondrial ATP synthase: diafenthiuron (L190), azocyclotin (L191), cyhexatin (L192), fenbutatin oxide (L193), propargite (L194) and tetradifon (L195);

Uncouplers of oxidative phosphorylation via disruption of the proton gradient: chlorfenapyr (L196), DNOC (L197) and sulfluramid (L198);

Nicotinic acetylcholine receptor (nAChR) channel blockers: bensultap (L199), cartap hydrochloride (L200), thiocyclam (L201) and thiosultap sodium (L202);

Inhibitors of the chitin biosynthesis type 0: bistrifluron (L203), chlorfluazuron (L204), diflubenzuron (L205), flucycloxuron (L206), flufenoxuron (L207), hexaflumuron (L208), lufenuron (L209), novaluron (L210), noviflumuron (L211), teflubenzuron (L212) and triflumuron (L213);

Inhibitors of the chitin biosynthesis type 1: buprofezin (L214);

Moulting disruptors: cyromazine (L215);

Ecdyson receptor agonists: methoxyfenozide (L216), tebufenozide (L217), halofenozide (L218), fufenozide (L219) and chromafenozide (L220);

Octopamin receptor agonists: amitraz (L221);

Mitochondrial complex III electron transport inhibitors: hydramethylnon (L222), acequinocyl (L223) and fluacrypyrim (L224);

Mitochondrial complex I electron transport inhibitors: fenazaquin (L225), fenpyroximate (L226), pyrimidifen (L227), pyridaben (L228), tebufenpyrad (L229), tolfenpyrad, (L230) and rotenone (L231);

Voltage-dependent sodium channel blockers: indoxacarb (L232), metaflumizone (L233), 2-[2-(4-cyanophenyl)-1-[3-(trifluoromethyl)phenyl]ethylidene]-N-[4-(difluoromethoxy)phenyl]-hydrazinecarboxamide (L234) and N-(3-chloro-2-methylphenyl)-2-[(4-chlorophenyl)-[4-[methyl(methylsulfonyl)amino]phenyl]methylene]-hydrazinecarboxamide (L235);

Inhibitors of the of acetyl CoA carboxylase: spirodiclofen (L236), spiromesifen (L237) and spirotetramat (L238);

Mitochondrial complex IV electron transport inhibitors: aluminium phosphide (L239), calcium phosphide (L240), phosphine (L241), zinc phosphide (L242), cyanide (L243); Mitochondrial complex II electron transport inhibitors: cyenopyrafen (L244) and cyflumetofen (L245);

Ryanodine receptor-modulators: flubendiamide (L246), chlorantraniliprole (L247), tetrachlorantraniliprole (L247a), cyantraniliprole (L248), cyclaniliprole (L249), tetraniliprole (L250), (R)-3-chloro-N 1-{2-methyl-4-[1,2,2,2-tetrafluoro-1-(trifluoromethyl)ethyl]phenyl}-N2-(1-methyl-2-methylsulfonylethyl)phthalamide (L251), (S)-3-chloro-N1-{2-methyl-4-[1,2,2,2-tetrafluoro-1-(trifluoromethyl)ethyl]phenyl}-N2-(1-methyl-2-methylsulfonylethyl)phthalamide (L252), methyl-2-[3,5-dibromo-2-({[3-bromo-1-(3-chloropyridin-2-yl)-1H-pyrazol-5-yl]carbonyl}-amino)benzoyl]-1,2-dimethylhydrazinecarboxylate (L253), N-[4,6-dichloro-2-[(diethyl-lambda-4-sulfanylidene) carbamoyl]-phenyl]-2-(3-chloro-2-pyridyl)-5-(trifluoromethyl)pyrazole-3-carboxamide (L254), N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (L255), N-[4-chloro-2-[(di-2-propyl-lambda-4-sulfanylidene) carbamoyl]-6-methyl-phenyl]-2-(3-chloro-2-pyridyl)-5-(trifluoromethyl)pyrazole-3-carboxamide (L256), N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (L257), N-[4,6-dibromo-2-[(diethyl-lambda-4-sulfanylidene) carbamoyl]-phenyl]-2-(3-chloro-2-pyridyl)-5-(trifluoromethyl)pyrazole-3-carboxamide (L258), N-[2-(5-amino-1,3,4-thiadiazol-2-yl)-4-chloro-6-methylphenyl]-3-bromo-1-(3-chloro-2-pyridinyl)-1H-pyrazole-5-carboxamide (L259), 3-chloro-1-(3-chloro-2-pyridinyl)-N-[2,4-dichloro-6-[[(1-cyano-1-methylethyl)amino]carbonyl]phenyl]-1H-pyrazole-5-carboxamide (L260), 3-bromo-N-[2,4-dichloro-6-(methylcarbamoyl)phenyl]-1-(3,5-dichloro-2-pyridyl)-

1H-pyrazole-5-carboxamide (L261), N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (L262) and cyhalodiamide (L263);

Insecticidal active compounds of unknown or uncertain mode of action: afidopyropen (L264), afoxolaner (L265), azadirachtin (L266), amidoflumet (L267), benzoximate (L268), bifenazate (L269), broflanilide (L270), bromopropylate (L271), chinomethionat (L272), cryolite (L273), dicloromezotiaz (L274), dicofol (L275), flufenerim (L276), flometoquin (L277), fluensulfone (L278), fluhexafon (L279), flupyradifurone (L280), fluralaner (L281), metoxadiazone (L282), piperonyl butoxide (L283), pyflubumide (L284), pyridalyl (L285), pyrifluquinazon (L286), sulfoxaflor (L287), tioxazafen (L288), triflumezopyrim (L289), 1,1-(4-chloro-2,6-dimethylphenyl)-12-hydroxy-1,4-dioxa-9-azadispiro[4.2.4.2]-tetradec-11-en-10-one (L290), 3-(4'-fluoro-2,4-dimethylbiphenyl-3-yl)-4-hydroxy-8-oxa-1-azaspiro[4.5]dec-3-en-2-one (L291), 1-[2-fluoro-4-methyl-5-[(2,2,2-trifluoroethyl)sulfinyl]phenyl]-3-(trifluoromethyl)-1H-1,2,4-triazole-5-am (L292), (E/Z)—N-[1-[(6-chloro-3-pyridyl)methyl]-2-pyridylidene]-2,2,2-trifluoro-acetamide (L293); (E/Z)—N-[1-[(6-chloro-5-fluoro-3-pyridyl)methyl]-2-pyridylidene]-2,2,2-trifluoro-acetamide (L294); (E/Z)-2,2,2-trifluoro-N-[1-[(6-fluoro-3-pyridyl)methyl]-2-pyridyli-dene]acetamide (L295); (E/Z)—N-[1-[(6-bromo-3-pyridyl)methyl]-2-pyridylidene]-2,2,2-trifluoro-acetamide (L296); (E/Z)—N-[1-[1-(6-chloro-3-pyridyl)ethyl]-2-pyridylidene]-2,2,2-trifluoro-acetamide (L297); (E/Z)—N-[1-[(6-chloro-3-pyridyl)methyl]-2-pyridylidene]-2,2-difluoro-acetamide (L298); (E/Z)-2-chloro-N-[1-[(6-chloro-3-pyridyl)methyl]-2-pyridylidene]-2,2-difluoro-acetamide (L299); (E/Z)—N-[1-[(2-chloropyrimidin-5-yl)methyl]-2-pyridylidene]-2,2,2-trifluoro-acetamide (L300); (E/Z)—N-[1-[(6-chloro-3-pyridyl)methyl]-2-pyridylidene]-2,2,3,3,3-pentafluoro-propanamide (L301); N-[1-[(6-chloro-3-pyridyl)methyl]-2-pyridylidene]-2,2,2-trifluoro-thioacetamide (L302); N-[1-[(6-chloro-3-pyridyl)methyl]-2-pyridylidene]-2,2,2-trifluoro-N'-isopropyl-acetamidine (L303); fluazaindolizine (L304); 4-[5-(3,5-dichlorophenyl)-5-(trifluoromethyl)-4H-isoxazol-3-yl]-2-methyl-N-(1-oxothietan-3-yl)benzami (L305); fluxametamide (L306); 5-[3-[2,6-dichloro-4-(3,3-dichloroallyloxy)phenoxy]propoxy]-1H-pyrazole (L307); 3-bromo-4-[1,2,2,3,3,3-hexafluoro-1-(trifluoromethyl)propyl]-6-(benzoylmethylamino)-N-[2-(trifluoromethyl)phenyl]-2-fluoro-benzamide (L308); 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide (L309); N-[3-[[[2-iodo-4-[1,2,2,2-tetrafluoro-1-(trifluoromethyl)ethyl]-6-(trifluoromethyl)phenyl]amino]carbonyl]phenyl]-N-benzamide (L310); N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide (L311); 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide (L312); 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide (L313); 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide (L314); 4-cyano-N-[2-cyano-5-[[2,6-dibromo-4-[1,2,2,3,3,3-hexafluoro-1-(trifluoromethyl)propyl]phenyl]carba-moyl]phenyl]-2-methyl-benzamide (L315); 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide (L316); N-[5-[[2-chloro-6-cyano-4-[1,2,2,3,3,3-hexafluoro-1-(trifluoromethyl)propyl]-phenyl]carbamoyl]-2-cyano-phenyl]-4-cyano-2-methyl-benzamide (L317); N—[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide (L318); N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide (L319); 4-cyano-N-[2-cyano-5-[[2,6-dichloro-4-[1,2,2,3,3,3-hexafluoro-1-(trifluoromethyl)-propyl]phenyl]carbamoyl]phenyl]-2-methyl-benzamide (L320); 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide (L321); N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide (L322); 2-(10,3-dioxan-2-yl)-6-[2-(3-pyridinyl)-5-thiazolyl]-pyridine; 2-[6-[2-(5-fluoro-3-pyridinyl)-5-thiazolyl]-2-pyridinyl]-pyrimidine (L323); 2-[6-[2-(3-pyridinyl)-5-thiazolyl]-2-pyridinyl]-pyrimidine (L324); N-methylsulfonyl-6-[2-(3-pyridyl)thiazol-5-yl]pyridine-2-car-boxamide (L325); N-methylsulfonyl-6-[2-(3-pyridyl)thiazol-5-yl]pyridine-2-carboxamide (L326); N-ethyl-N-[4-methyl-2-(3-pyridyl)thiazol-5-yl]-3-methylthio-propanamide (L327); N-methyl-N-[4-methyl-2-(3-pyridyl)thiazol-5-yl]-3-methylthio-propanamide (L328); N,2-dimethyl-N-[4-methyl-2-(3-pyridyl)thiazol-5-yl]-3-methylthio-propanamide (L329); N-ethyl-2-methyl-N-[4-methyl-2-(3-pyridyl)thiazol-5-yl]-3-methylthio-propanamide (L330); N-[4-chloro-2-(3-pyridyl)thiazol-5-yl]-N-ethyl-2-methyl-3-methylthio-propanamide (L331); N-[4-chloro-2-(3-pyridyl)thiazol-5-yl]-N,2-dimethyl-3-methylthio-propanamide (L332); N-[4-chloro-2-(3-pyridyl)thiazol-5-yl]-N-methyl-3-methylthio-propanamide (L333); N-[4-chloro-2-(3-pyridyl)thiazol-5-yl]-N-ethyl-3-methylthio-propanamide (L334); 1-[(6-chloro-3-pyri-dinyl)methyl]-1,2,3,5,6,7-hexahydro-5-methoxy-7-methyl-8-nitro-imidazo[1,2-a]pyridine (L335); 1-[(6-chloropyridin-3-yl)methyl]-7-methyl-8-nitro-1,2,3,5,6J-hexahydroimid alpyridin-5-ol (L336); 1-isopropyl-N,5-dimethyl-N-pyridazin-4-yl-pyrazole-4-carboxamide (L337); 1-(1,2-dimethylpropyl)-N-ethyl-5-methyl-N-pyridazin-4-yl-pyrazole-4-carboxamide (L338); N,5-dimethyl-N-pyridazin-4-yl-1-(2,2,2-trifluoro-1-methyl-ethyl)pyrazole-4-carboxamide (L339); 1-[1-(1-cyanocyclopropyl)ethyl]-N-ethyl-5-methyl-N-pyridazin-4-yl-pyrazole-4-carboxamide (L340); N-ethyl-1-(2-fluoro-1-methyl-propyl)-5-methyl-N-pyridazin-4-yl-pyrazole-4-carboxamide (L341); 1-(1,2-dimethylpropyl)-N,5-dimethyl-N-pyridazin-4-yl-pyrazole-4-carboxamide (L342); 1-[1-(1-cyanocyclopropyl)ethyl]-N,5-dimethyl-N-pyridazin-4-yl-pyrazole-4-carboxamide (L343); N-methyl-1-(2-fluoro-1-methyl-propyl]-5-methyl-N-pyridazin-4-yl-pyrazole-4-carboxamide (L344); 1-(4, 4-difluorocyclohexyl)-N-ethyl-5-methyl-N-pyridazin-4-yl-pyrazole-4-carboxamide (L345); 1-(4,4-difluorocyclohexyl)-N,5-dimethyl-N-pyridazin-4-yl-pyrazole-4-carboxamide (L346), N-(1-methylethyl)-2-(3-pyridinyl)-2H-inda-zole-4-carboxamide (L347); N-cyclopropyl-2-(3-pyridinyl)-2H-indazole-4-carboxamide (L348); N-cyclohexyl-2-(3-pyridinyl)-2H-indazole-4-carboxamide (L349); 2-(3-pyridinyl)-N-(2,2,2-trifluoroethyl)-2H-indazole-4-carboxamide (L350); 2-(3-pyridinyl)-N-[(tetrahydro-2-furanyl)methyl]-2H-indazole-5-carboxamide (L351); methyl 2-[[2-(3-pyridinyl)-2H-indazol-5-yl]carbonyl]hydrazinecarboxylate (L352); N-[(2,2-difluorocyclopropyl)methyl]-2-(3-pyridinyl)-2H-indazole-5-carboxamide (L353); N-(2,2-difluoropropyl)-2-(3-pyridinyl)-2H-indazole-5-carboxamide (L354); 2-(3-pyridinyl)-N-(2-pyrimidinylmethyl)-2H-indazole-5-carboxamide (L355); N-[(5-methyl-2-pyrazinyl)methyl]-2-(3-pyridinyl)-2H-indazole-5-carboxamide (L356), N-[3-chloro-1-(3-pyridyl)pyrazol-4-yl]-N-ethyl-3-(3,3,3-trifluoropropylsulfanyl)-propanamide (L357); N-[3-chloro-1-(3-pyridyl)pyrazol-4-yl]-N-ethyl-3-(3,3,3-trifluoropropylsulfinyl)propanamide (L3588); N-[3-chloro-1-(3-pyridyl)pyrazol-4-yl]-3-[(2,2-difluorocyclopropyl)methylsulfanyl]-N-ethyl-propanamide (L359); N-[3-chloro-1-(3-pyridyl)pyrazol-4-yl]-3-[(2,2-difluorocyclopropyl)methylsulfinyl]-N-ethyl-propanamide (L360); sarolaner (L361) and lotilaner (L362).

All named mixing partners of the classes (A) to (L) can, if their functional groups enable this, optionally form salts with suitable bases or acids.

Where a component (1) or a component (2) can be present in a tautomeric form, such a compound is understood herein above and herein below also to include, where applicable, corresponding tautomeric forms, even when these are not specifically mentioned in each case.

The active substances referred to as component 2, their preparation and their activity e.g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP141317; EP152031; EP226917; EP243970; EP256503; EP428941; EP532022; EP1028125; EP1035122; EP1201648; EP1122244, JP2002316902; DE19650197; DE10021412; DE102005009458; U.S. Pat. Nos. 3,296,272; 3,325,503; WO9846608; WO9914187; WO9924413; WO9927783; WO0029404; WO0046148; WO0065913; WO0154501; WO 0156358; WO0222583; WO0240431; WO0310149; WO0311853; WO0314103; WO0316286; WO0353145; WO0361388; WO0366609; WO0374491; WO0449804; WO0483193; WO05120234; WO05123689; WO05123690; WO0563721; WO0587772; WO0587773; WO0615866; WO0687325; WO0687343; WO0782098; WO0790624; WO11028657; WO2012168188; WO2007006670; WO201177514; WO13047749; WO10069882; WO13047441; WO0316303; WO0990181; WO13007767; WO1310862; WO13127704; WO13024009; WO13024010; WO13047441; WO13162072; WO13092224 and WO11135833.

In one embodiment, the fungicidal composition comprising as component 2 is at least one active compound selected from inhibitors of complex III at $Q_o$ site in group A), more preferably selected from azoxystrobin (A001), dimoxystrobin (A004), fluoxastrobin (A008), kresoxim-methyl (A009), mandestrobin (A010), metominostrobin (A011), orysastrobin (A012), picoxystrobin (A013), pyraclostrobin (A014), trifloxystrobin (A017), triclopyricarb/chlorodincarb (A020), famoxadone (A021), fenamidone (A021a), 1-[3-bromo-2-[[1-(4-chlorophenyl)pyrazol-3-yl]oxymethyl]phenyl]-4-methyl-tetrazol-5-one (A024), metyltetraprole (A025), 1-[2-[[1-(4-chlorophenyl)pyrazol-3-yl]oxymethyl]-3-fluoro-phenyl]-4-methyl-tetrazol-5-one (A026), 1-[2-[[1-(2,4-dichlorophenyl)pyrazol-3-yl]oxymethyl]-3-fluoro-phenyl]-4-methyl-tetrazol-5-one (A027), 1-[3-cyclopropyl-2-[[2-methyl-4-(1-methylpyrazol-3-yl)phenoxy]-methyl]phenyl]-4-methyl-tetrazol-5-one (A030), 1-[3-(difluoromethoxy)-2-[2-methyl-4-(1-methylpyrazol-3-yl)phenoxy]methyl]phenyl]-4-methyl-tetrazol-5-one (A031), 1-methyl-4-[3-methyl-2-[2-methyl-4-(1-methylpyrazol-3-yl)phenoxy]methyl]phenyl]tetrazol-5-one (A032), (Z,2E)-5-[1-(2,4-dichlorophenyl)pyrazol-3-yl]-oxy-2-methoxyimino-N,3-dimethyl-pent-3-enamide (A034) and (Z,2E)-5-[1-(4-chlorophenyl)pyrazol-3-yl]oxy-2-methoxyimino-N,3-dimethyl-pent-3-enamide (A035).

In one embodiment, the fungicidal composition comprising as component 2 is at least one active compound selected from inhibitors of complex III at Qi site in group A), more preferably selected from cyazofamid (A039), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A041), fenpicoxamid (A042), [(6S,7R,8R)-8-benzyl-3-[4-methoxy-3-(propanoyloxymethoxy)pyridine-2-carbonyl]amino]-6-methyl-4,9-dioxo-1,5-dioxonan-7-yl]-2-methylpropanoate (A043) and florylpicoxamid (A044).

In one embodiment, the fungicidal composition comprising as component 2 is at least one active compound selected from inhibitors of complex II in group A), more preferably selected from benzovindiflupyr (A047), bixafen (A048), boscalid (A049), fluopyram (A053), flufenoxadiazam (A055), fluxapyroxad (A057), fluindapyr (A059), isopyrazam (A060), isofetamid (A061), isoflucypram (A062), inpyrfluxam (A063) penflufen (A067), penthiopyrad (A068), pydiflumetofen (A069), N-[2-(3,4-difluorophenyl)phenyl]-3-(trifluoromethyl)pyrazine-2-carboxamide (A070), sedaxane (A071), tecloftalam (A072), thifluzamide (A073), 3-(difluoromethyl)-1-methyl-N-(1,1,3-trimethyl-indan-4-yl)pyrazole-4-carboxamide (A074), 3-(trifluoromethyl)-1-methyl-N-(1,1,3-trimethyl-indan-4-yl)pyrazole-4-carboxamide (A075), 1,3-dimethyl-N-(1,1,3-trimethylindan-4-yl)pyrazole-4-carboxamide (A076), 3-(trifluoromethyl)-1,5-dimethyl-N-(1,1,3-trimethylindan-4-yl)pyrazole-4-carboxamide (A077), 1,3,5-trimethyl-N-(1,1,3-trimethyl-indan-4-yl)pyrazole-4-carboxamide (A078), 3-(difluoromethyl)-1,5-dimethyl-N-(1,1,3-trimethyl-indan-4-yl)pyrazole-4-carboxamide (A079), 3-(difluoromethyl)-N-(7-fluoro-1,1,3-trimethyl-indan-4-yl)-1-methyl-pyrazole-4-carboxamide (A080), N-[2-[2-chloro-4-(trifluoromethyl)phenoxy]phenyl]-3-(difluoromethyl)-5-fluoro-1-methyl-pyrazole-4-carboxamide (A081), methyl (E)-2-[2-[(5-cyano-2-methyl-phenoxy)methyl]phenyl]-3-methoxy-prop-2-enoate (A082), N-[(5-chloro-2-isopropyl-phenyl)methyl]-N-cyclopropyl-3-(difluoromethyl)-5-fluoro-1-methyl-pyrazole-4-carboxamide (A083), 2-(difluoromethyl)-N-(1,1,3-trimethyl-indan-4-yl)pyridine-3-carboxamide (A084), 2-(difluoromethyl)-N-[(3R)-1,1,3-trimethyl-indan-4-yl]pyridine-3-carboxamide (A085), 2-(difluoromethyl)-N-[(3S)3-ethyl-1,1-dimethyl-indan-4-yl]pyridine-3-carboxamide (A086), 2-(difluoromethyl)-N-[(3R)-3-ethyl-1,1-dimethyl-indan-4-yl]pyridine-3-carboxamide (A087), 2-(difluoromethyl)-N-(1,1-dimethyl-3-propyl-indan-4-yl)pyridine-3-carboxamide (A088), 2-(difluoromethyl)-N-[(3R)-1,1-dimethyl-3-propyl-indan-4-yl]pyridine-3-carboxamide (A089), 2-(difluoromethyl)-N-(3-isobutyl-1,1-dimethyl-indan-4-yl)pyridine-3-carboxamide (A090) and 2-(difluoromethyl)-N-[(3R)-3-isobutyl-1,1-dimethyl-indan-4 yl]pyridine-3-carboxamide (A091).

In one embodiment, the fungicidal composition comprising as component 2 is at least one active compound selected from other respiration inhibitors in group A), more preferably selected from fluazinam (A097) and ametoctradin (A103).

In one embodiment, the fungicidal composition comprising as component 2 is at least one active compound selected from C14 demethylase inhibitors in group B), more preferably selected from cyproconazole (B004), difenoconazole (B005), epoxiconazole (B008), fluquinconazole (B0011), fluoxytioconazole (B009), flusilazole (B012), flutriafol (B013), hexaconazole (B014), metconazole (B017), myclobutanil (B018), penconazole (B021), propiconazole (B022), prothioconazole (B023), tebuconazole (B025), tetraconazole (B026), triticonazole (B029), 2-[2-chloro-4-(4-chlorophenoxy)phenyl]-1-(1,2,4-triazol-1-yl)pentan-2-ol (B033), 1-[4-(4-chlorophenoxy)-2-(trifluoromethyl)phenyl]-1-cyclopropyl-2-(1,2,4-triazol-1-yl)ethanol (B034), 2-[2-chloro-4-(4-chlorophenoxy)phenyl]-1-(1,2,4-triazol-1-yl)butan-2-ol (B036), ipfentrifluconazole (B037), mefentrifluconazole (B038), 2-(chloromethyl)-2-methyl-5-(p-tolylmethyl)-1-(1,2,4-triazol-1-ylmethyl)cyclopentanol (B043) and prochloraz (B047).

In one embodiment, the fungicidal composition as component 2 is at least one active compound selected from Delta14-reductase inhibitors in group B), more preferably selected from fenpropimorph (B056), tridemorph (B057), fenpropidin (B058) and spiroxamine (B060).

In one embodiment, the fungicidal composition comprising as component 2 is at least one active compound selected from phenylamides and acyl amino acid fungicides in group C), more preferably selected from benalaxyl (C001), benalaxyl-M (C002), metalaxyl (C004), metalaxyl-M (C005) and ofurace (C006).

In one embodiment, the fungicidal composition comprising as component 2 is at least one active compound selected from other nucleic acid synthesis inhibitors in group C), more preferably selected from 5-fluoro-2-(p-tolylmethoxy)pyrimidin-4-amine ($C_{013}$), 5-fluoro-2-(4-fluorophenylmethoxy)pyrimidin-4-amine ($C_{014}$) and 5-fluoro-2-(4-chlorophenylmethoxy)pyrimidin-4 amine ($C_{015}$).

In one embodiment, the fungicidal composition comprising as component 2 is at least one active compound selected from inhibitors of cell division and cytoskeleton in group D), more preferably selected from benomyl (D001), carbendazim (D002), thiophanate-methyl (D005), fluopicolide (D020), metrafenone (D022) and pyriofenone (D023).

In one embodiment, the fungicidal composition comprising as component 2 is at least one active compound selected from inhibitors of amino acid and protein synthesis in group E), more preferably selected from cyprodinil (E001), pyrimethanil (E003); kasugamycin (E005) and kasugamycin hydrochloride-hydrate (E006).

In one embodiment, the fungicidal composition comprising as component 2 is at least one active compound selected from signal transduction inhibitors in group F), more preferably selected from fluoroimid (F001), vinclozolin (F004) and fludioxonil (F005).

In one embodiment, the fungicidal composition comprising as component 2 is at least one active compound selected from lipid and membrane synthesis inhibitors in group G), more preferably selected from dimethomorph (G012), mandipropamid (G014), iprovalicarb (G017), oxathiapiprolin (G020), fluoxapiprolin (G021), 2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)phenyl methanesulfonate (G022), 2-{3-[2-(1-{[3,5-bis(difluoromethyl)-1H-pyrazol-1-yl]-acetyl}piperidin-4-yl) 1,3-thiazol-4-yl]-4,5-dihydro-1,2-oxazol-5-yl}-3-chlorophenyl methanesulfonate (G023), 4-[1-[2-[3-(difluoromethyl)-5-methyl-pyrazol-1-yl]acetyl]-4-piperidyl]-N-tetralin-1-yl-pyridine-2-carboxamide (G024), 4-[1-[2-[3,5-bis(difluoromethyl) pyrazol-1-yl]acetyl]-4-piperidyl]-N-tetralin-1-yl-pyridine-2-carboxamide (G025), 4-[1-[2-[3-(difluoromethyl)-5-(trifluoromethyl)pyrazol-1-yl]acetyl]-4-piperidyl]-N-tetralin-1-yl-pyridine-2-carboxamide (G026), 4-[1-[2-[5-cyclopropyl-3-(difluoromethyl)pyrazol-1-yl]acetyl]-4-piperidyl]-N-tetralin-1-yl-pyridine-2-carboxamide (G027), 4-[1-[2-[5-methyl-3-(trifluoromethyl)pyrazol-1-yl]acetyl]-4-piperidyl]-N-tetralin-1-yl-pyridine-2-carboxamide (G028), 4-[1-[2-[5-(difluoromethyl)-3-(trifluoro-methyl) pyrazol-1-yl]acetyl]-4-piperidyl]-N-tetralin-1-yl-pyridine-2-carboxamide (G029), 4-[1-[2-[3,5-bis(trifluoromethyl) pyrazol-1-yl]acetyl]-4-piperidyl]-N-tetralin-1-yl-pyridine-2-carboxamide (G030) and (4-[1-[2-[5-cyclopropyl-3-(trifluoromethyl)pyrazol-1-yl]acetyl]-4-piperidyl]-N-tetralin-1-yl-pyridine-2-carboxamide (G031).

In one embodiment, the fungicidal composition comprising as component 2 is at least one active compound selected from inhibitors with multi site action in group H), more preferably selected from copper oxychloride (H005), sulfur (H007), mancozeb (H009), maneb (H010), metiram (H012), propineb (H013), thiram (H014), zineb (H015), ziram (H016), chlorothalonil (H018), captafol (H019), folpet (H021), dichlofluanid (H022), dithianon (H036) and 2,6-dimethyl-1H,5H-[1,4]dithiino[2,3-c:5,6-c']dipyrrole-1,3,5,7(2H,6H)-tetraone (H037).

In one embodiment, the fungicidal composition comprising as component 2 is at least one active compound selected from cell wall synthesis inhibitors in group I), more preferably selected from tricyclazole (I004) and fenoxanil (1007).

In one embodiment, the fungicidal composition comprising as component 2 is at least one active compound selected from plant defence inducers in group J), more preferably selected from probenazole (J002), prohexadione-calcium (J005); fosetyl (J006), fosetyl-aluminum (J007), phosphorous acid and its salts (J008), calcium phosphonate (J011) and potassium phosphonate (J012).

In one embodiment, the fungicidal composition comprising as component 2 is at least one active compound selected from unknown mode of action compounds in group K), more preferably selected from cyflufenamid (K003), ipflufenoquin (K019), N'-[4-[3-[(4-chorophenyl)methyl]-1,2,4-thiadiazo-5-yl]oxy]-2,5-dimethyl-phenyl]-N-ethyl-N-methyl-formamidine (K031), N'-(5-bromo-6-indan-2-yloxy-2-methyl-3-pyridyl)-N-ethyl-N-methyl-formamidine (K032), N'-[5-bromo-6-[1-(3,5-difluorophenyl)ethoxy]-2-methyl-3-pyridyl]-N-ethyl-N-methyl-formamidine (K033), N'-[5-bromo-6-(4-isopropylcyclohexoxy)-2-methyl-3-pyridyl]-N-ethyl-N-methyl-formamidine (K034), picarbutrazox (K043), pentyl N-[6-[[(Z)-[(1-methyltetrazol-5-yl)-phenyl-methylene]amino]oxymethyl]-2-pyridyl] carbamate (K044), 2-[2-[(7,8-difluoro-2-methyl-3-quinolyl) oxy]-6-fluoro-phenyl]propan-2-ol (K046), 2-[2-fluoro-6-[(8-fluoro-2-methyl-3-quinolyl)oxy]phenyl]propan-2-ol (K047), 3-(5-fluoro-3,3,4,4-tetramethyl-3,4-dihydroisoquinolin-1-yl)quinoline (K048), quinofumelin (K049), 9-fluoro-2,2-dimethyl-5-(3-quinolyl)-3H-1,4-benzoxazepine (K050) and N'-[5-bromo-2-methyl-6-(1-methyl-2-propoxy-ethoxy)-3-pyridyl]-N-ethyl-N-methyl-formamidine (K056).

In another embodiment, the fungicidal composition comprising as component 2 is at least one active compound selected from Inhibitors of complex III at $Q_o$ site selected from azoxystrobin (A001), fluoxastrobin (A008), metominostrobin (A011), picoxystrobin (A013), pyraclostrobin (A014), trifloxystrobin (A017), metyltetraprole (A025), Inhibitors of complex III at Qi site selected from fenpicoxamid (A042), Inhibitors of complex II selected from benzovindiflupyr (A047), bixafen (A048), boscalid (A049), fluopyram (A053), flufenoxadiazam (A055) fluxapyroxad (A057), fluindapyr (A059), isoflucypram (A062), inpyrfluxam (A063), pydiflumetofen (A069), Other respiration inhibitors selected from fluazinam (A097), C14 demethylase inhibitors selected from cyproconazole (B004), difenoconazole (B005), epoxiconazole (B008), fluoxytioconazole (B009), tetraconazol (B026), fenpropimorph (B056), flutriafol (B013), metconazole (B017), propiconazole (B022), prothioconazole (B023), tebuconazole (B025), mefentrifluconazole (B038), Nucleic Acid Synthesis Inhibitors selected from metalaxyl (C004), Tubulin inhibitors selected from carbendazim (D002), thiophanate-methyl (D005), MAP/histidine kinase inhibitors selected from fludioxonil (F005), Inhibitors of oxysterol binding protein selected from oxathiapiprolin (G020), fluoxapiprolin (G021), Inhibitors with multi site action selected from mancozeb (H009), metiram (H012), propineb (H013), chlorothalonil (H018), folpet (H021), dithianon (H036), thiram (H014) and unknown mode of action selected from ipflufenoquin (K019) and quinofumelin (K049).

In a preferred embodiment, the fungicidal composition comprising as component 2 is at least one active compound selected from Inhibitors of complex III at $Q_o$ site selected from azoxystrobin (A001), fluoxastrobin (A008), metominostrobin (A011), picoxystrobin (A013), pyraclostrobin (A014), trifloxystrobin (A017), metyltetraprole (A025), Inhibitors of complex III at Qi site selected from fenpicoxamid (A042), Inhibitors of complex II selected from benzovindiflupyr (A047), bixafen (A048), boscalid (A049), fluopyram (A053), flufenoxadiazam (A055) fluxapyroxad (A057), fluindapyr (A059), isoflucypram (A062), inpyrfluxam (A063), pydiflumetofen (A069), Other respiration inhibitors selected from fluazinam (A097), C14 demethylase inhibitors selected from cyproconazole (B004), difenoconazole (B005), epoxiconazole (B008), fluoxytioconazole (B009), tetraconazol (B026), fenpropimorph (B056), flutriafol (B013), metconazole (B017), propiconazole (B022), prothioconazole (B023), tebuconazole (B025), mefentrifluconazole (B038) and Inhibitors with multi site action selected from mancozeb (H009), metiram (H012), propineb (H013), chlorothalonil (H018), folpet (H021), dithianon (H036), thiram (H014).

Yet another preferred embodiment, the fungicidal composition comprising as component 2 is at least one active compound selected from Inhibitors of complex III at $Q_o$ site selected from azoxystrobin (A001), metominostrobin (A011), picoxystrobin (A013), pyraclostrobin (A014), trifloxystrobin (A017), Inhibitors of complex II selected from benzovindiflupyr (A047), bixafen (A048), boscalid (A049), fluopyram (A053), fluxapyroxad (A057), fluindapyr (A059), inpyrfluxam (A063), Other respiration inhibitors selected from fluazinam (A097), C14 demethylase inhibitors selected from prothioconazole (B023), tebuconazole (B025), mefentrifluconazole (B038) and Inhibitors with multi site action selected from mancozeb (H009), metiram (H012), propineb (H013), folpet (H021), dithianon (H036).

In one embodiment, the present invention provides a novel fungicidal composition comprising a mixture of component (1) and component (2), wherein component (1) is at least one compound of formula (I) or an agriculturally acceptable salt thereof;

Formula (I)

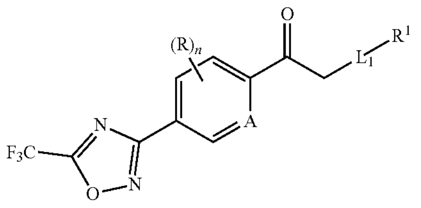

wherein;

A represents $CH_2$;

$L^1$ represents —$NR^2$— or —O—;

$R^1$ is selected from the group consisting of phenyl and pyridinyl; each group of $R^1$ may optionally be substituted with one or more groups of $R^{1a}$;

$R^{1a}$ is selected from the group consisting of halogen, cyano, nitro, hydroxy, $C_1$-$C_6$-alkyl, $C_1$-$C_6$-haloalkyl and $C_1$-$C_6$-alkoxy;

$R^2$ is selected from the group consisting of hydrogen and $C_1$-$C_6$-alkyl;

n represents integer 0;

and component (2) is at least one further active compound selected from Inhibitors of complex III at $Q_o$ site selected from azoxystrobin (A001), metominostrobin (A011), picoxystrobin (A013), pyraclostrobin (A014), trifloxystrobin (A017), Inhibitors of complex II selected from benzovindiflupyr (A047), bixafen (A048), boscalid (A049), fluopyram (A053), fluxapyroxad (A057), fluindapyr (A059), inpyrfluxam (A063), Other respiration inhibitors selected from fluazinam (A097), C14 demethylase inhibitors selected from prothioconazole (B023), tebuconazole (B025), mefentrifluconazole (B038) and Inhibitors with multi site action selected from mancozeb (H009), metiram (H012), propineb (H013), folpet (H021) and dithianon (H036).

In another embodiment, the present invention provides a novel fungicidal composition comprising a mixture of component (1) and component (2), wherein component (1) is at least one compound of formula (I) or an agriculturally acceptable salt thereof selected from 2-(3-fluorophenoxy)-1-(4-(5-(trifluoromethyl)-1,2,4-oxadiazol-3-yl)phenyl)ethan-1-one (I-1), 2-(4-fluorophenoxy)-1-(4-(5-(trifluoromethyl)-1,2,4-oxadiazol-3-yl)phenyl)ethan-1-one (I-2), 2-((6-fluoropyridin-3-yl)oxy)-1-(4-(5-(trifluoromethyl)-1,2,4-oxadiazol-3-yl)phenyl)ethan-1-one (I-3), 2-(thiazol-2-ylsulfonyl)-1-(4-(5-(trifluoromethyl)-1,2,4-oxadiazol-3-yl)phenyl)ethan-1-one (I-4), 2-((3-fluorophenyl)amino)-1-(4-(5-(trifluoromethyl)-1,2,4-oxadiazol-3-yl)phenyl)ethan-1-one (I-5), 2-(benzylthio)-1-(5-(5-(trifluoromethyl)-1,2,4-oxadiazol-3-yl)pyridin-2-yl)ethan-1-one (I-6), 2-((3-fluorophenyl)sulfinyl)-1-(5-(5-(trifluoromethyl)-1,2,4-oxadiazol-3-yl)pyridin-2-yl)ethan-1-one (I-7) or 2-((4-fluorophenyl)amino)-1-(4-(5-(trifluoromethyl)-1,2,4-oxadiazol-3-yl)phenyl)ethan-1-one (I-8) and component (2)

is at least one further active compound selected from Inhibitors of complex III at $Q_o$ site selected from azoxystrobin (A001), metominostrobin (A011), picoxystrobin (A013), pyraclostrobin (A014), trifloxystrobin (A017), Inhibitors of complex II selected from benzovindiflupyr (A047), bixafen (A048), boscalid (A049), fluopyram (A053), fluxapyroxad (A057), fluindapyr (A059), inpyrfluxam (A063), Other respiration inhibitors selected from fluazinam (A097), C14 demethylase inhibitors selected from prothioconazole (B023), tebuconazole (B025), mefentrifluconazole (B038) and Inhibitors with multi site action selected from mancozeb (H009), metiram (H012), propineb (H013), folpet (H021) and dithianon (H036).

The following combinations exemplify specific embodiments of the fungicidal composition to the present invention.

Following combinations are listed in Table-1, wherein component (1) is a compound of formula (I) and another component (2) is selected from the groups A) to L) as defined herein (component 2, for example, (A001 or azoxystrobin, in combination [(I)+(A001)].

TABLE 1

| |
|---|
| (I) + (A001), (I) + (A002), (I) + (A003), (I) + (A004), (I) + (A005), (I) + (A006), (I) + (A007), (I) + (A008), |
| (I) + (A009), (I) + (A010), (I) + (A011), (I) + (A012), (I) + (A013), (I) + (A014), (I) + (A015), (I) + (A016), |
| (I) + (A017), (I) + (A018), (I) + (A019), (I) + (A020), (I) + (A021), (I) + (A022), (I) + (A023), (I) + (A024), |
| (I) + (A025), (I) + (A026), (I) + (A027), (I) + (A028), (I) + (A029), (I) + (A030), (I) + (A031), (I) + (A032), |
| (I) + (A033), (I) + (A034), (I) + (A035), (I) + (A036), (I) + (A037), (I) + (A038), (I) + (A039), (I) + (A040), |
| (I) + (A041), (I) + (A042), (I) + (A043), (I) + (A044), (I) + (A045), (I) + (A046), (I) + (A047), (I) + (A048), |
| (I) + (A049), (I) + (A050), (I) + (A051), (I) + (A052), (I) + (A053), (I) + (A054), (I) + (A055), (I) + (A056), |
| (I) + (A057), (I) + (A058), (I) + (A059), (I) + (A060), (I) + (A061), (I) + (A062), (I) + (A063), (I) + (A064), |
| (I) + (A065), (I) + (A066), (I) + (A067), (I) + (A068), (I) + (A069), (I) + (A070), (I) + (A071), (I) + (A072), |
| (I) + (A073), (I) + (A074), (I) + (A075), (I) + (A076), (I) + (A077), (I) + (A078), (I) + (A079), (I) + (A080), |
| (I) + (A081), (I) + (A082), (I) + (A083), (I) + (A084), (I) + (A085), (I) + (A086), (I) + (A087), (I) + (A088), |
| (I) + (A089), (I) + (A090), (I) + (A091), (I) + (A092), (I) + (A093), (I) + (A094), (I) + (A095), (I) + (A096), |
| (I) + (A097), (I) + (A098), (I) + (A099), (I) + (A100), (I) + (A101), (I) + (A102), (I) + (A103), (I) + (A104), |
| (I) + (B001), (I) + (B002), (I) + (B003), (I) + (B004), (I) + (B005), (I) + (B006), (I) + (B007), (I) + (B008), |
| (I) + (B009), (I) + (B010), (I) + (B011), (I) + (B012), (I) + (B013), (I) + (B014), (I) + (B015), (I) + (B016), |
| (I) + (B017), (I) + (B018), (I) + (B019), (I) + (B020), (I) + (B021), (I) + (B022), (I) + (B023), (I) + (B024), |
| (I) + (B025), (I) + (B026), (I) + (B027), (I) + (B028), (I) + (B029), (I) + (B030), (I) + (B031), (I) + (B032), |
| (I) + (B033), (I) + (B034), (I) + (B035), (I) + (B036), (I) + (B037), (I) + (B038), (I) + (B039), (I) + (B040), |
| (I) + (B041), (I) + (B042), (I) + (B043), (I) + (B044), (I) + (B045), (I) + (B046), (I) + (B047), (I) + (B048), |
| (I) + (B049), (I) + (B050), (I) + (B051), (I) + (B052), (I) + (B053), (I) + (B054), (I) + (B055), (I) + (B056), |
| (I) + (B057), (I) + (B058), (I) + (B059), (I) + (B060), (I) + (B061), (I) + (B062), (I) + (C001), (I) + (C002), |
| (I) + (C003), (I) + (C004), (I) + (C005), (I) + (C006), (I) + (C007), (I) + (C008), (I) + (C009), (I) + (C010), |
| (I) + (C011), (I) + (C012), (I) + (C013), (I) + (C014), (I) + (C015), (I) + (D001), (I) + (D002), (I) + (D003), |
| (I) + (D004), (I) + (D005), (I) + (D006), (I) + (D007), (I) + (D008), (I) + (D009), (I) + (D010), (I) + (D011), |
| (I) + (D012), (I) + (D013), (I) + (D014), (I) + (D015), (I) + (D016), (I) + (D017), (I) + (D018), (I) + (D019), |
| (I) + (D020), (I) + (D021), (I) + (D022), (I) + (D023), (I) + (E001), (I) + (E002), (I) + (E003), (I) + (E004), |
| (I) + (E005), (I) + (E006), (I) + (E007), (I) + (E008), (I) + (E009), (I) + (F001), (I) + (F002), (I) + (F003), |
| (I) + (F004), (I) + (F005), (I) + (F006), (I) + (F007), (I) + (G001), (I) + (G002), (I) + (G003), (I) + (G004), |
| (I) + (G005), (I) + (G006), (I) + (G007), (I) + (G008), (I) + (G009), (I) + (G010), (I) + (G011), (I) + (G012), |
| (I) + (G013), (I) + (G014), (I) + (G015), (I) + (G016), (I) + (G017), (I) + (G018), (I) + (G019), (I) + (G020), |
| (I) + (G021), (I) + (G022), (I) + (G023), (I) + (G024), (I) + (G025), (I) + (G026), (I) + (G027), (I) + (G028), |
| (I) + (G029), (I) + (G030), (I) + (G031), (I) + (H001), (I) + (H002), (I) + (H003), (I) + (H004), (I) + (H005), |
| (I) + (H006), (I) + (H007), (I) + (H008), (I) + (H009), (I) + (H010), (I) + (H011), (I) + (H012), (I) + (H013), |
| (I) + (H014), (I) + (H015), (I) + (H016), (I) + (H017), (I) + (H018), (I) + (H019), (I) + (H020), (I) + (H021), |
| (I) + (H022), (I) + (H023), (I) + (H024), (I) + (H025), (I) + (H026), (I) + (H027), (I) + (H028), (I) + (H029), |
| (I) + (H030), (I) + (H031), (I) + (H032), (I) + (H033), (I) + (H034), (I) + (H035), (I) + (H036), (I) + (H037), |
| (I) + (I001), (I) + (I002), (I) + (I003), (I) + (I004), (I) + (I005), (I) + (I006), (I) + (I007), (I) + (J001), |
| (I) + (J002), (I) + (J003), (I) + (J004), (I) + (J005), (I) + (J006), (I) + (J007), (I) + (J008), (I) + (J009), |
| (I) + (J010), (I) + (J011), (I) + (J012), (I) + (K001), (I) + (K002), (I) + (K003), (I) + (K004), (I) + (K005), |
| (I) + (K006), (I) + (K007), (I) + (K008), (I) + (K009), (I) + (K010), (I) + (K011), (I) + (K012), (I) + (K013), |
| (I) + (K014), (I) + (K015), (I) + (K016), (I) + (K017), (I) + (K018), (I) + (K019), (I) + (K020), (I) + (K021), |
| (I) + (K022), (I) + (K023), (I) + (K024), (I) + (K025), (I) + (K026), (I) + (K027), (I) + (K028), (I) + (K029), |
| (I) + (K030), (I) + (K031), (I) + (K032), (I) + (K033), (I) + (K034), (I) + (K035), (I) + (K036), (I) + (K037), |
| (I) + (K038), (I) + (K039), (I) + (K040), (I) + (K041), (I) + (K042), (I) + (K043), (I) + (K044), (I) + (K045), |
| (I) + (K046), (I) + (K047), (I) + (K048), (I) + (K049), (I) + (K050), (I) + (K051), (I) + (K052), (I) + (K053), |
| (I) + (K054), (I) + (K055), (I) + (K056) (I) + (K055), (I) + (K056), (I) + (K057), (I) + (K058), (I) + (K059), |
| (I) + (K060), (I) + (K061), (I) + (K062), (I) + (K063), (I) + (K064), (I) + (L001), (I) + (L002), (I) + (L003), |
| (I) + (L004), (I) + (L005), (I) + (L006), (I) + (L007), (I) + (L008), (I) + (L009), (I) + (L010), (I) + (L011), |
| (I) + (L012), (I) + (L013), (I) + (L014), (I) + (L015), (I) + (L016), (I) + (L017), (I) + (L018), (I) + (L019), |
| (I) + (L020), (I) + (L021), (I) + (L022), (I) + (L023), (I) + (L024), (I) + (L025), (I) + (L026), (I) + (L027), |
| (I) + (L028), (I) + (L029), (I) + (L030), (I) + (L031), (I) + (L032), (I) + (L033), (I) + (L034), (I) + (L035), |
| (I) + (L036), (I) + (L037), (I) + (L038), (I) + (L039), (I) + (L040), (I) + (L041), (I) + (L042), (I) + (L043), |
| (I) + (L044), (I) + (L045), (I) + (L046), (I) + (L047), (I) + (L048), (I) + (L049), (I) + (L050), (I) + (L051), |
| (I) + (L052), (I) + (L053), (I) + (L054), (I) + (L055), (I) + (L056), (I) + (L057), (I) + (L058), (I) + (L059), |
| (I) + (L060), (I) + (L061), (I) + (L062), (I) + (L063), (I) + (L064), (I) + (L065), (I) + (L066), (I) + (L067), |
| (I) + (L068), (I) + (L069), (I) + (L070), (I) + (L071), (I) + (L072), (I) + (L073), (I) + (L074), (I) + (L075), |
| (I) + (L076), (I) + (L077), (I) + (L078), (I) + (L079), (I) + (L080), (I) + (L081), (I) + (L082), (I) + (L083), |
| (I) + (L084), (I) + (L085), (I) + (L086), (I) + (L087), (I) + (L088), (I) + (L089), (I) + (L090), (I) + (L091), |
| (I) + (L092), (I) + (L093), (I) + (L094), (I) + (L095), (I) + (L096), (I) + (L097), (I) + (L098), (I) + (L099), |
| (I) + (L100), (I) + (L101), (I) + (L102), (I) + (L103), (I) + (L104), (I) + (L105), (I) + (L106), (I) + (L107), |
| (I) + (L108), (I) + (L109), (I) + (L110), (I) + (L111), (I) + (L112), (I) + (L113), (I) + (L114), (I) + (L115), |
| (I) + (L116), (I) + (L117), (I) + (L118), (I) + (L119), (I) + (L120), (I) + (L121), (I) + (L122), (I) + (L123), |
| (I) + (L124), (I) + (L125), (I) + (L126), (I) + (L127), (I) + (L128), (I) + (L129), (I) + (L130), (I) + (L131), |
| (I) + (L132), (I) + (L133), (I) + (L134), (I) + (L135), (I) + (L136), (I) + (L137), (I) + (L138), (I) + (L139), |
| (I) + (L140), (I) + (L141), (I) + (L142), (I) + (L143), (I) + (L144), (I) + (L145), (I) + (L146), (I) + (L147), |
| (I) + (L148), (I) + (L149), (I) + (L150), (I) + (L151), (I) + (L152), (I) + (L153), (I) + (L154), (I) + (L155), |
| (I) + (L156), (I) + (L157), (I) + (L158), (I) + (L159), (I) + (L160), (I) + (L161), (I) + (L162), (I) + (L163), |

TABLE 1-continued

| |
|---|
| (I) + (L164), (I) + (L165), (I) + (L166), (I) + (L167), (I) + (L168), (I) + (L169), (I) + (L170), (I) + (L171), |
| (I) + (L172), (I) + (L173), (I) + (L174), (I) + (L175), (I) + (L176), (I) + (L177), (I) + (L178), (I) + (L179), |
| (I) + (L180), (I) + (L181), (I) + (L182), (I) + (L183), (I) + (L184), (I) + (L185), (I) + (L186), (I) + (L187), |
| (I) + (L188), (I) + (L189), (I) + (L190), (I) + (L191), (I) + (L192), (I) + (L193), (I) + (L194), (I) + (L195), |
| (I) + (L196), (I) + (L197), (I) + (L198), (I) + (L199), (I) + (L200), (I) + (L201), (I) + (L202), (I) + (L203), |
| (I) + (L204), (I) + (L205), (I) + (L206), (I) + (L207), (I) + (L208), (I) + (L209), (I) + (L210), (I) + (L211), |
| (I) + (L212), (I) + (L213), (I) + (L214), (I) + (L215), (I) + (L216), (I) + (L217), (I) + (L218), (I) + (L219), |
| (I) + (L220), (I) + (L221), (I) + (L222), (I) + (L223), (I) + (L224), (I) + (L225), (I) + (L226), (I) + (L227), |
| (I) + (L228), (I) + (L229), (I) + (L230), (I) + (L231), (I) + (L232), (I) + (L233), (I) + (L234), (I) + (L235), |
| (I) + (L236), (I) + (L237), (I) + (L238), (I) + (L239), (I) + (L240), (I) + (L241), (I) + (L242), (I) + (L243), |
| (I) + (L244), (I) + (L245), (I) + (L246), (I) + (L247), (I) + (L248), (I) + (L249), (I) + (L250), (I) + (L251), |
| (I) + (L252), (I) + (L253), (I) + (L254), (I) + (L255), (I) + (L256), (I) + (L257), (I) + (L258), (I) + (L259), |
| (I) + (L260), (I) + (L261), (I) + (L262), (I) + (L263), (I) + (L264), (I) + (L265), (I) + (L266), (I) + (L267), |
| (I) + (L268), (I) + (L269), (I) + (L270), (I) + (L271), (I) + (L272), (I) + (L273), (I) + (L274), (I) + (L275), |
| (I) + (L276), (I) + (L277), (I) + (L278), (I) + (L279), (I) + (L280), (I) + (L281), (I) + (L282), (I) + (L283), |
| (I) + (L284), (I) + (L285), (I) + (L286), (I) + (L287), (I) + (L288), (I) + (L289), (I) + (L290), (I) + (L291), |
| (I) + (L292), (I) + (L293), (I) + (L294), (I) + (L295), (I) + (L296), (I) + (L297), (I) + (L298), (I) + (L299), |
| (I) + (L300), (I) + (L301), (I) + (L302), (I) + (L303), (I) + (L304), (I) + (L305), (I) + (L306), (I) + (L307), |
| (I) + (L308), (I) + (L309), (I) + (L310), (I) + (L311), (I) + (L312), (I) + (L313), (I) + (L314), (I) + (L315), |
| (I) + (L316), (I) + (L317), (I) + (L318), (I) + (L319), (I) + (L320), (I) + (L321), (I) + (L322), (I) + (L323), |
| (I) + (L324), (I) + (L325), (I) + (L326), (I) + (L327), (I) + (L328), (I) + (L329), (I) + (L330), (I) + (L331), |
| (I) + (L332), (I) + (L333), (I) + (L334), (I) + (L335), (I) + (L336), (I) + (L337), (I) + (L338), (I) + (L339), |
| (I) + (L340), (I) + (L341), (I) + (L342), (I) + (L343), (I) + (L344), (I) + (L345), (I) + (L346), (I) + (L347), |
| (I) + (L348), (I) + (L349), (I) + (L350), (I) + (L351), (I) + (L352), (I) + (L353), (I) + (L354), (I) + (L355), |
| (I) + (L356), (I) + (L357), (I) + (L358), (I) + (L359), (I) + (L360), (I) + (L361), (I) + (L362). |

In one embodiment, the weight ratio of component (1) to component (2) is between 100:1 and 1:100 in combinations [(I)+(A001] to [(I)+(L362)] of Table: 1.

In one embodiment, the weight ratio of component (1) to component (2) is between 50:1 and 1:50 in combinations [(I)+(A001] to [(I)+(L362)] of Table: 1.

In one embodiment, the weight ratio of component (1) to component (2) is between 20:1 and 1:20 in combinations [(I)+(A001] to [(I)+(L362)] of Table: 1.

In one embodiment, the weight ratio of component (1) to component (2) is between 5:1 and 1:5 in combinations [(I)+(A001] to [(I)+(L362)] of Table: 1.

In one embodiment, the weight ratio of component (1) to component (2) is between 3:1 and 1:3 in combinations [(I)+(A001] to [(I)+(L362)] of Table: 1.

In one embodiment, the weight ratio of component (1) to component (2) is 1:1 in combinations [(1)+(A001] to [(1)+(L362)] of Table: 1.

Following combinations are listed in Table-2, wherein component (1) is a compound of formula (I-2) and another component (2) is selected from the groups A) to L) as defined herein (component 2, for example, (A001 or azoxystrobin, in combination [(I-2)+(A001)].

TABLE 2

| |
|---|
| (I-2) + (A001), (I-2) + (A002), (I-2) + (A003), (I-2) + (A004), (I-2) + (A005), (I-2) + (A006), (I-2) + (A007), (I- |
| 2) + (A008), (I-2) + (A009), (I-2) + (A010), (I-2) + (A011), (I-2) + (A012), (I-2) + (A013), (I-2) + (A014), (I- |
| 2) + (A015), (I-2) + (A016), (I-2) + (A017), (I-2) + (A018), (I-2) + (A019), (I-2) + (A020), (I-2) + (A021), (I- |
| 2) + (A022), (I-2) + (A023), (I-2) + (A024), (I-2) + (A025), (I-2) + (A026), (I-2) + (A027), (I-2) + (A028), (I- |
| 2) + (A029), (I-2) + (A030), (I-2) + (A031), (I-2) + (A032), (I-2) + (A033), (I-2) + (A034), (I-2) + (A035), (I- |
| 2) + (A036), (I-2) + (A037), (I-2) + (A038), (I-2) + (A039), (I-2) + (A040), (I-2) + (A041), (I-2) + (A042), (I- |
| 2) + (A043), (I-2) + (A044), (I-2) + (A045), (I-2) + (A046), (I-2) + (A047), (I-2) + (A048), (I-2) + (A049), (I- |
| 2) + (A050), (I-2) + (A051), (I-2) + (A052), (I-2) + (A053), (I-2) + (A054), (I-2) + (A055), (I-2) + (A056), (I- |
| 2) + (A057), (I-2) + (A058), (I-2) + (A059), (I-2) + (A060), (I-2) + (A061), (I-2) + (A062), (I-2) + (A063), (I- |
| 2) + (A064), (I-2) + (A065), (I-2) + (A066), (I-2) + (A067), (I-2) + (A068), (I-2) + (A069), (I-2) + (A070), (I- |
| 2) + (A071), (I-2) + (A072), (I-2) + (A073), (I-2) + (A074), (I-2) + (A075), (I-2) + (A076), (I-2) + (A077), (I- |
| 2) + (A078), (I-2) + (A079), (I-2) + (A080), (I-2) + (A081), (I-2) + (A082), (I-2) + (A083), (I-2) + (A084), (I- |
| 2) + (A085), (I-2) + (A086), (I-2) + (A087), (I-2) + (A088), (I-2) + (A089), (I-2) + (A090), (I-2) + (A091), (I- |
| 2) + (A092), (I-2) + (A093), (I-2) + (A094), (I-2) + (A095), (I-2) + (A096), (I-2) + (A097), (I-2) + (A098), (I- |
| 2) + (A099), (I-2) + (A100), (I-2) + (A101), (I-2) + (A102), (I-2) + (A103), (I-2) + (A104), (I-2) + (B001), (I- |
| 2) + (B002), (I-2) + (B003), (I-2) + (B004), (I-2) + (B005), (I-2) + (B006), (I-2) + (B007), (I-2) + (B008), (I- |
| 2) + (B009), (I-2) + (B010), (I-2) + (B011), (I-2) + (B012), (I-2) + (B013), (I-2) + (B014), (I-2) + (B015), (I- |
| 2) + (B016), (I-2) + (B017), (I-2) + (B018), (I-2) + (B019), (I-2) + (B020), (I-2) + (B021), (I-2) + (B022), (I- |
| 2) + (B023), (I-2) + (B024), (I-2) + (B025), (I-2) + (B026), (I-2) + (B027), (I-2) + (B028), (I-2) + (B029), (I- |
| 2) + (B030), (I-2) + (B031), (I-2) + (B032), (I-2) + (B033), (I-2) + (B034), (I-2) + (B035), (I-2) + (B036), (I- |
| 2) + (B037), (I-2) + (B038), (I-2) + (B039), (I-2) + (B040), (I-2) + (B041), (I-2) + (B042), (I-2) + (B043), (I- |
| 2) + (B044), (I-2) + (B045), (I-2) + (B046), (I-2) + (B047), (I-2) + (B048), (I-2) + (B049), (I-2) + (B050), (I- |
| 2) + (B051), (I-2) + (B052), (I-2) + (B053), (I-2) + (B054), (I-2) + (B055), (I-2) + (B056), (I-2) + (B057), (I- |
| 2) + (B058), (I-2) + (B059), (I-2) + (B060), (I-2) + (B061), (I-2) + (B062), (I-2) + (C001), (I-2) + (C002), (I- |
| 2) + (C003), (I-2) + (C004), (I-2) + (C005), (I-2) + (C006), (I-2) + (C007), (I-2) + (C008), (I-2) + (C009), (I- |
| 2) + (C010), (I-2) + (C011), (I-2) + (C012), (I-2) + (C013), (I-2) + (C014), (I-2) + (C015), (I-2) + (D001), (I- |
| 2) + (D002), (I-2) + (D003), (I-2) + (D004), (I-2) + (D005), (I-2) + (D006), (I-2) + (D007), (I-2) + (D008), (I- |
| 2) + (D009), (I-2) + (D010), (I-2) + (D011), (I-2) + (D012), (I-2) + (D013), (I-2) + (D014), (I-2) + (D015), (I- |
| 2) + (D016), (I-2) + (D017), (I-2) + (D018), (I-2) + (D019), (I-2) + (D020), (I-2) + (D021), (I-2) + (D022), (I- |
| 2) + (D023), (I-2) + (E001), (I-2) + (E002), (I-2) + (E003), (I-2) + (E004), (I-2) + (E005), (I-2) + (E006), (I- |
| 2) + (E007), (I-2) + (E008), (I-2) + (E009), (I-2) + (F001), (I-2) + (F002), (I-2) + (F003), (I-2) + (F004), (I- |
| 2) + (F005), (I-2) + (F006), (I-2) + (F007), (I-2) + (G001), (I-2) + (G002), (I-2) + (G003), (I-2) + (G004), (I- |
| 2) + (G005), (I-2) + (G006), (I-2) + (G007), (I-2) + (G008), (I-2) + (G009), (I-2) + (G010), (I-2) + (G011), (I- |
| 2) + (G012), (I-2) + (G013), (I-2) + (G014), (I-2) + (G015), (I-2) + (G016), (I-2) + (G017), (I-2) + (G018), (I- |

TABLE 2-continued

2) + (G019), (I-2) + (G020), (I-2) + (G021), (I-2) + (G022), (I-2) + (G023), (I-2) + (G024), (I-2) + (G025), (I-
2) + (G026), (I-2) + (G027), (I-2) + (G028), (I-2) + (G029), (I-2) + (G030), (I-2) + (G031), (I-2) + (H001), (I-
2) + (H002), (I-2) + (H003), (I-2) + (H004), (I-2) + (H005), (I-2) + (H006), (I-2) + (H007), (I-2) + (H008), (I-
2) + (H009), (I-2) + (H010), (I-2) + (H011), (I-2) + (H012), (I-2) + (H013), (I-2) + (H014), (I-2) + (H015), (I-
2) + (H016), (I-2) + (H017), (I-2) + (H018), (I-2) + (H019), (I-2) + (H020), (I-2) + (H021), (I-2) + (H022), (I-
2) + (H023), (I-2) + (H024), (I-2) + (H025), (I-2) + (H026), (I-2) + (H027), (I-2) + (H028), (I-2) + (H029), (I-
2) + (H030), (I-2) + (H031), (I-2) + (H032), (I-2) + (H033), (I-2) + (H034), (I-2) + (H035), (I-2) + (H036), (I-
2) + (H037), (I-2) + (I001), (I-2) + (I002), (I-2) + (I003), (I-2) + (I004), (I-2) + (I005), (I-2) + (I006), (I-
2) + (1007), (I-2) + (J001), (I-2) + (J002), (I-2) + (J003), (I-2) + (J004), (I-2) + (J005), (I-2) + (J006), (I-
2) + (J007), (I-2) + (J008), (I-2) + (J009), (I-2) + (J010), (I-2) + (J011), (I-2) + (J012), (I-2) + (K001), (I-
2) + (K002), (I-2) + (K003), (I-2) + (K004), (I-2) + (K005), (I-2) + (K006), (I-2) + (K007), (I-2) + (K008), (I-
2) + (K009), (I-2) + (K010), (I-2) + (K011), (I-2) + (K012), (I-2) + (K013), (I-2) + (K014), (I-2) + (K015), (I-
2) + (K016), (I-2) + (K017), (I-2) + (K018), (I-2) + (K019), (I-2) + (K020), (I-2) + (K021), (I-2) + (K022), (I-
2) + (K023), (I-2) + (K024), (I-2) + (K025), (I-2) + (K026), (I-2) + (K027), (I-2) + (K028), (I-2) + (K029), (I-
2) + (K030), (I-2) + (K031), (I-2) + (K032), (I-2) + (K033), (I-2) + (K034), (I-2) + (K035), (I-2) + (K036), (I-
2) + (K037), (I-2) + (K038), (I-2) + (K039), (I-2) + (K040), (I-2) + (K041), (I-2) + (K042), (I-2) + (K043), (I-
2) + (K044), (I-2) + (K045), (I-2) + (K046), (I-2) + (K047), (I-2) + (K048), (I-2) + (K049), (I-2) + (K050), (I-
2) + (K051), (I-2) + (K052), (I-2) + (K053), (I-2) + (K054), (I-2) + (K055), (I-2) + (K056) (I-2) + (K055), (I-
2) + (K056), (I-2) + (K057), (I-2) + (K058), (I-2) + (K059), (I-2) + (K060), (I-2) + (K061), (I-2) + (K062), (I-
2) + (K063), (I-2) + (K064), (I-2) + (L001), (I-2) + (L002), (I-2) + (L003), (I-2) + (L004), (I-2) + (L005), (I-
2) + (L006), (I-2) + (L007), (I-2) + (L008), (I-2) + (L009), (I-2) + (L010), (I-2) + (L011), (I-2) + (L012), (I-
2) + (L013), (I-2) + (L014), (I-2) + (L015), (I-2) + (L016), (I-2) + (L017), (I-2) + (L018), (I-2) + (L019), (I-
2) + (L020), (I-2) + (L021), (I-2) + (L022), (I-2) + (L023), (I-2) + (L024), (I-2) + (L025), (I-2) + (L026), (I-
2) + (L027), (I-2) + (L028), (I-2) + (L029), (I-2) + (L030), (I-2) + (L031), (I-2) + (L032), (I-2) + (L033), (I-
2) + (L034), (I-2) + (L035), (I-2) + (L036), (I-2) + (L037), (I-2) + (L038), (I-2) + (L039), (I-2) + (L040), (I-
2) + (L041), (I-2) + (L042), (I-2) + (L043), (I-2) + (L044), (I-2) + (L045), (I-2) + (L046), (I-2) + (L047), (I-
2) + (L048), (I-2) + (L049), (I-2) + (L050), (I-2) + (L051), (I-2) + (L052), (I-2) + (L053), (I-2) + (L054), (I-
2) + (L055), (I-2) + (L056), (I-2) + (L057), (I-2) + (L058), (I-2) + (L059), (I-2) + (L060), (I-2) + (L061), (I-
2) + (L062), (I-2) + (L063), (I-2) + (L064), (I-2) + (L065), (I-2) + (L066), (I-2) + (L067), (I-2) + (L068), (I-
2) + (L069), (I-2) + (L070), (I-2) + (L071), (I-2) + (L072), (I-2) + (L073), (I-2) + (L074), (I-2) + (L075), (I-
2) + (L076), (I-2) + (L077), (I-2) + (L078), (I-2) + (L079), (I-2) + (L080), (I-2) + (L081), (I-2) + (L082), (I-
2) + (L083), (I-2) + (L084), (I-2) + (L085), (I-2) + (L086), (I-2) + (L087), (I-2) + (L088), (I-2) + (L089), (I-
2) + (L090), (I-2) + (L091), (I-2) + (L092), (I-2) + (L093), (I-2) + (L094), (I-2) + (L095), (I-2) + (L096), (I-
2) + (L097), (I-2) + (L098), (I-2) + (L099), (I-2) + (L100), (I-2) + (L101), (I-2) + (L102), (I-2) + (L103), (I-
2) + (L104), (I-2) + (L105), (I-2) + (L106), (I-2) + (L107), (I-2) + (L108), (I-2) + (L109), (I-2) + (L110), (I-
2) + (L111), (I-2) + (L112), (I-2) + (L113), (I-2) + (L114), (I-2) + (L115), (I-2) + (L116), (I-2) + (L117), (I-
2) + (L118), (I-2) + (L119), (I-2) + (L120), (I-2) + (L121), (I-2) + (L122), (I-2) + (L123), (I-2) + (L124), (I-
2) + (L125), (I-2) + (L126), (I-2) + (L127), (I-2) + (L128), (I-2) + (L129), (I-2) + (L130), (I-2) + (L131), (I-
2) + (L132), (I-2) + (L133), (I-2) + (L134), (I-2) + (L135), (I-2) + (L136), (I-2) + (L137), (I-2) + (L138), (I-
2) + (L139), (I-2) + (L140), (I-2) + (L141), (I-2) + (L142), (I-2) + (L143), (I-2) + (L144), (I-2) + (L145), (I-
2) + (L146), (I-2) + (L147), (I-2) + (L148), (I-2) + (L149), (I-2) + (L150), (I-2) + (L151), (I-2) + (L152), (I-
2) + (L153), (I-2) + (L154), (I-2) + (L155), (I-2) + (L156), (I-2) + (L157), (I-2) + (L158), (I-2) + (L159), (I-
2) + (L160), (I-2) + (L161), (I-2) + (L162), (I-2) + (L163), (I-2) + (L164), (I-2) + (L165), (I-2) + (L166), (I-
2) + (L167), (I-2) + (L168), (I-2) + (L169), (I-2) + (L170), (I-2) + (L171), (I-2) + (L172), (I-2) + (L173), (I-
2) + (L174), (I-2) + (L175), (I-2) + (L176), (I-2) + (L177), (I-2) + (L178), (I-2) + (L179), (I-2) + (L180), (I-
2) + (L181), (I-2) + (L182), (I-2) + (L183), (I-2) + (L184), (I-2) + (L185), (I-2) + (L186), (I-2) + (L187), (I-
2) + (L188), (I-2) + (L189), (I-2) + (L190), (I-2) + (L191), (I-2) + (L192), (I-2) + (L193), (I-2) + (L194), (I-
2) + (L195), (I-2) + (L196), (I-2) + (L197), (I-2) + (L198), (I-2) + (L199), (I-2) + (L200), (I-2) + (L201), (I-
2) + (L202), (I-2) + (L203), (I-2) + (L204), (I-2) + (L205), (I-2) + (L206), (I-2) + (L207), (I-2) + (L208), (I-
2) + (L209), (I-2) + (L210), (I-2) + (L211), (I-2) + (L212), (I-2) + (L213), (I-2) + (L214), (I-2) + (L215), (I-
2) + (L216), (I-2) + (L217), (I-2) + (L218), (I-2) + (L219), (I-2) + (L220), (I-2) + (L221), (I-2) + (L222), (I-
2) + (L223), (I-2) + (L224), (I-2) + (L225), (I-2) + (L226), (I-2) + (L227), (I-2) + (L228), (I-2) + (L229), (I-
2) + (L230), (I-2) + (L231), (I-2) + (L232), (I-2) + (L233), (I-2) + (L234), (I-2) + (L235), (I-2) + (L236), (I-
2) + (L237), (I-2) + (L238), (I-2) + (L239), (I-2) + (L240), (I-2) + (L241), (I-2) + (L242), (I-2) + (L243), (I-
2) + (L244), (I-2) + (L245), (I-2) + (L246), (I-2) + (L247), (I-2) + (L248), (I-2) + (L249), (I-2) + (L250), (I-
2) + (L251), (I-2) + (L252), (I-2) + (L253), (I-2) + (L254), (I-2) + (L255), (I-2) + (L256), (I-2) + (L257), (I-
2) + (L258), (I-2) + (L259), (I-2) + (L260), (I-2) + (L261), (I-2) + (L262), (I-2) + (L263), (I-2) + (L264), (I-
2) + (L265), (I-2) + (L266), (I-2) + (L267), (I-2) + (L268), (I-2) + (L269), (I-2) + (L270), (I-2) + (L271), (I-
2) + (L272), (I-2) + (L273), (I-2) + (L274), (I-2) + (L275), (I-2) + (L276), (I-2) + (L277), (I-2) + (L278), (I-
2) + (L279), (I-2) + (L280), (I-2) + (L281), (I-2) + (L282), (I-2) + (L283), (I-2) + (L284), (I-2) + (L285), (I-
2) + (L286), (I-2) + (L287), (I-2) + (L288), (I-2) + (L289), (I-2) + (L290), (I-2) + (L291), (I-2) + (L292), (I-
2) + (L293), (I-2) + (L294), (I-2) + (L295), (I-2) + (L296), (I-2) + (L297), (I-2) + (L298), (I-2) + (L299), (I-
2) + (L300), (I-2) + (L301), (I-2) + (L302), (I-2) + (L303), (I-2) + (L304), (I-2) + (L305), (I-2) + (L306), (I-
2) + (L307), (I-2) + (L308), (I-2) + (L309), (I-2) + (L310), (I-2) + (L311), (I-2) + (L312), (I-2) + (L313), (I-
2) + (L314), (I-2) + (L315), (I-2) + (L316), (I-2) + (L317), (I-2) + (L318), (I-2) + (L319), (I-2) + (L320), (I-
2) + (L321), (I-2) + (L322), (I-2) + (L323), (I-2) + (L324), (I-2) + (L325), (I-2) + (L326), (I-2) + (L327), (I-
2) + (L328), (I-2) + (L329), (I-2) + (L330), (I-2) + (L331), (I-2) + (L332), (I-2) + (L333), (I-2) + (L334), (I-
2) + (L335), (I-2) + (L336), (I-2) + (L337), (I-2) + (L338), (I-2) + (L339), (I-2) + (L340), (I-2) + (L341), (I-
2) + (L342), (I-2) + (L343), (I-2) + (L344), (I-2) + (L345), (I-2) + (L346), (I-2) + (L347), (I-2) + (L348), (I-
2) + (L349), (I-2) + (L350), (I-2) + (L351), (I-2) + (L352), (I-2) + (L353), (I-2) + (L354), (I-2) + (L355), (I-
2) + (L356), (I-2) + (L357), (I-2) + (L358), (I-2) + (L359), (I-2) + (L360), (I-2) + (L361), (I-2) + (L362).

In one embodiment, the weight ratio of component (1) to component (2) is between 100:1 and 1:100 in combinations [(I-2)+(A001] to [(I-2)+(L362)] of Table: 2.

In one embodiment, the weight ratio of component (1) to component (2) is between 50:1 and 1:50 in combinations [(I-2)+(A001] to [(I-2)+(L362)] of Table: 2.

In one embodiment, the weight ratio of component (1) to component (2) is between 20:1 and 1:20 in combinations [(I-2)+(A001] to [(I-2)+(L362)] of Table: 2.

In one embodiment, the weight ratio of component (1) to component (2) is between 5:1 and 1:5 in combinations [(I-2)+(A001] to [(I-2)+(L362)] of Table: 2.

In one embodiment, the weight ratio of component (1) to component (2) is between 3:1 and 1:3 in combinations [(I-2)+(A001] to [(I-2)+(L362)] of Table: 2.

In one embodiment, the weight ratio of component (1) to component (2) is 1:1 in combinations [(I-2)+(A001] to [(I-2)+(L362)] of Table: 2.

Following combinations are listed in Table-3, wherein component (1) is a compound of formula (I-3) and another component (2) is selected from the groups A) to L) as defined herein (component 2, for example, (A001 or azoxystrobin, in combination [(I-3)+(A001)].

TABLE 3

(I-3) + (A001), (I-3) + (A002), (I-3) + (A003), (I-3) + (A004), (I-3) + (A005), (I-3) + (A006), (I-3) + (A007), (I-3) + (A008), (I-3) + (A009), (I-3) + (A010), (I-3) + (A011), (I-3) + (A012), (I-3) + (A013), (I-3) + (A014), (I-3) + (A015), (I-3) + (A016), (I-3) + (A017), (I-3) + (A018), (I-3) + (A019), (I-3) + (A020), (I-3) + (A021), (I-3) + (A022), (I-3) + (A023), (I-3) + (A024), (I-3) + (A025), (I-3) + (A026), (I-3) + (A027), (I-3) + (A028), (I-3) + (A029), (I-3) + (A030), (I-3) + (A031), (I-3) + (A032), (I-3) + (A033), (I-3) + (A034), (I-3) + (A035), (I-3) + (A036), (I-3) + (A037), (I-3) + (A038), (I-3) + (A039), (I-3) + (A040), (I-3) + (A041), (I-3) + (A042), (I-3) + (A043), (I-3) + (A044), (I-3) + (A045), (I-3) + (A046), (I-3) + (A047), (I-3) + (A048), (I-3) + (A049), (I-3) + (A050), (I-3) + (A051), (I-3) + (A052), (I-3) + (A053), (I-3) + (A054), (I-3) + (A055), (I-3) + (A056), (I-3) + (A057), (I-3) + (A058), (I-3) + (A059), (I-3) + (A060), (I-3) + (A061), (I-3) + (A062), (I-3) + (A063), (I-3) + (A064), (I-3) + (A065), (I-3) + (A066), (I-3) + (A067), (I-3) + (A068), (I-3) + (A069), (I-3) + (A070), (I-3) + (A071), (I-3) + (A072), (I-3) + (A073), (I-3) + (A074), (I-3) + (A075), (I-3) + (A076), (I-3) + (A077), (I-3) + (A078), (I-3) + (A079), (I-3) + (A080), (I-3) + (A081), (I-3) + (A082), (I-3) + (A083), (I-3) + (A084), (I-3) + (A085), (I-3) + (A086), (I-3) + (A087), (I-3) + (A088), (I-3) + (A089), (I-3) + (A090), (I-3) + (A091), (I-3) + (A092), (I-3) + (A093), (I-3) + (A094), (I-3) + (A095), (I-3) + (A096), (I-3) + (A097), (I-3) + (A098), (I-3) + (A099), (I-3) + (A100), (I-3) + (A101), (I-3) + (A102), (I-3) + (A103), (I-3) + (A104), (I-3) + (B001), (I-3) + (B002), (I-3) + (B003), (I-3) + (B004), (I-3) + (B005), (I-3) + (B006), (I-3) + (B007), (I-3) + (B008), (I-3) + (B009), (I-3) + (B010), (I-3) + (B011), (I-3) + (B012), (I-3) + (B013), (I-3) + (B014), (I-3) + (B015), (I-3) + (B016), (I-3) + (B017), (I-3) + (B018), (I-3) + (B019), (I-3) + (B020), (I-3) + (B021), (I-3) + (B022), (I-3) + (B023), (I-3) + (B024), (I-3) + (B025), (I-3) + (B026), (I-3) + (B027), (I-3) + (B028), (I-3) + (B029), (I-3) + (B030), (I-3) + (B031), (I-3) + (B032), (I-3) + (B033), (I-3) + (B034), (I-3) + (B035), (I-3) + (B036), (I-3) + (B037), (I-3) + (B038), (I-3) + (B039), (I-3) + (B040), (I-3) + (B041), (I-3) + (B042), (I-3) + (B043), (I-3) + (B044), (I-3) + (B045), (I-3) + (B046), (I-3) + (B047), (I-3) + (B048), (I-3) + (B049), (I-3) + (B050), (I-3) + (B051), (I-3) + (B052), (I-3) + (B053), (I-3) + (B054), (I-3) + (B055), (I-3) + (B056), (I-3) + (B057), (I-3) + (B058), (I-3) + (B059), (I-3) + (B060), (I-3) + (B061), (I-3) + (B062), (I-3) + (C001), (I-3) + (C002), (I-3) + (C003), (I-3) + (C004), (I-3) + (C005), (I-3) + (C006), (I-3) + (C007), (I-3) + (C008), (I-3) + (C009), (I-3) + (C010), (I-3) + (C011), (I-3) + (C012), (I-3) + (C013), (I-3) + (C014), (I-3) + (C015), (I-3) + (D001), (I-3) + (D002), (I-3) + (D003), (I-3) + (D004), (I-3) + (D005), (I-3) + (D006), (I-3) + (D007), (I-3) + (D008), (I-3) + (D009), (I-3) + (D010), (I-3) + (D011), (I-3) + (D012), (I-3) + (D013), (I-3) + (D014), (I-3) + (D015), (I-3) + (D016), (I-3) + (D017), (I-3) + (D018), (I-3) + (D019), (I-3) + (D020), (I-3) + (D021), (I-3) + (D022), (I-3) + (D023), (I-3) + (E001), (I-3) + (E002), (I-3) + (E003), (I-3) + (E004), (I-3) + (E005), (I-3) + (E006), (I-3) + (E007), (I-3) + (E008), (I-3) + (E009), (I-3) + (F001), (I-3) + (F002), (I-3) + (F003), (I-3) + (F004), (I-3) + (F005), (I-3) + (F006), (I-3) + (F007), (I-3) + (G001), (I-3) + (G002), (I-3) + (G003), (I-3) + (G004), (I-3) + (G005), (I-3) + (G006), (I-3) + (G007), (I-3) + (G008), (I-3) + (G009), (I-3) + (G010), (I-3) + (G011), (I-3) + (G012), (I-3) + (G013), (I-3) + (G014), (I-3) + (G015), (I-3) + (G016), (I-3) + (G017), (I-3) + (G018), (I-3) + (G019), (I-3) + (G020), (I-3) + (G021), (I-3) + (G022), (I-3) + (G023), (I-3) + (G024), (I-3) + (G025), (I-3) + (G026), (I-3) + (G027), (I-3) + (G028), (I-3) + (G029), (I-3) + (G030), (I-3) + (G031), (I-3) + (H001), (I-3) + (H002), (I-3) + (H003), (I-3) + (H004), (I-3) + (H005), (I-3) + (H006), (I-3) + (H007), (I-3) + (H008), (I-3) + (H009), (I-3) + (H010), (I-3) + (H011), (I-3) + (H012), (I-3) + (H013), (I-3) + (H014), (I-3) + (H015), (I-3) + (H016), (I-3) + (H017), (I-3) + (H018), (I-3) + (H019), (I-3) + (H020), (I-3) + (H021), (I-3) + (H022), (I-3) + (H030), (I-3) + (H031), (I-3) + (H032), (I-3) + (H033), (I-3) + (H034), (I-3) + (H035), (I-3) + (H036), (I-3) + (H023), (I-3) + (H024), (I-3) + (H025), (I-3) + (H026), (I-3) + (H027), (I-3) + (H028), (I-3) + (H029), (I-3) + (H030), (I-3) + (H031), (I-3) + (H032), (I-3) + (H033), (I-3) + (H034), (I-3) + (H035), (I-3) + (H036), (I-3) + (H037), (I-3) + (I001), (I-3) + (I002), (I-3) + (I003), (I-3) + (I004), (I-3) + (I005), (I-3) + (I006), (I-3) + (I007), (I-3) + (J001), (I-3) + (J002), (I-3) + (J003), (I-3) + (J004), (I-3) + (J005), (I-3) + (J006), (I-3) + (J007), (I-3) + (J008), (I-3) + (J009), (I-3) + (J010), (I-3) + (J011), (I-3) + (J012), (I-3) + (K001), (I-3) + (K002), (I-3) + (K003), (I-3) + (K004), (I-3) + (K005), (I-3) + (K006), (I-3) + (K007), (I-3) + (K008), (I-3) + (K009), (I-3) + (K010), (I-3) + (K011), (I-3) + (K012), (I-3) + (K013), (I-3) + (K014), (I-3) + (K015), (I-3) + (K016), (I-3) + (K017), (I-3) + (K018), (I-3) + (K019), (I-3) + (K020), (I-3) + (K021), (I-3) + (K022), (I-3) + (K023), (I-3) + (K024), (I-3) + (K025), (I-3) + (K026), (I-3) + (K027), (I-3) + (K028), (I-3) + (K029), (I-3) + (K030), (I-3) + (K031), (I-3) + (K032), (I-3) + (K033), (I-3) + (K034), (I-3) + (K035), (I-3) + (K036), (I-3) + (K037), (I-3) + (K038), (I-3) + (K039), (I-3) + (K040), (I-3) + (K041), (I-3) + (K042), (I-3) + (K043), (I-3) + (K044), (I-3) + (K045), (I-3) + (K046), (I-3) + (K047), (I-3) + (K048), (I-3) + (K049), (I-3) + (K050), (I-3) + (K051), (I-3) + (K052), (I-3) + (K053), (I-3) + (K054), (I-3) + (K055), (I-3) + (K056) (I-3) + (K055), (I-3) + (K056), (I-3) + (K057), (I-3) + (K058), (I-3) + (K059), (I-3) + (K060), (I-3) + (K061), (I-3) + (K062), (I-3) + (K063), (I-3) + (K064), (I-3) + (L001), (I-3) + (L002), (I-3) + (L003), (I-3) + (L004), (I-3) + (L005), (I-3) + (L006), (I-3) + (L007), (I-3) + (L008), (I-3) + (L009), (I-3) + (L010), (I-3) + (L011), (I-3) + (L012), (I-3) + (L013), (I-3) + (L014), (I-3) + (L015), (I-3) + (L016), (I-3) + (L017), (I-3) + (L018), (I-3) + (L019), (I-3) + (L020), (I-3) + (L021), (I-3) + (L022), (I-3) + (L023), (I-3) + (L024), (I-3) + (L025), (I-3) + (L026), (I-3) + (L027), (I-3) + (L028), (I-3) + (L029), (I-3) + (L030), (I-3) + (L031), (I-3) + (L032), (I-3) + (L033), (I-3) + (L034), (I-3) + (L035), (I-3) + (L036), (I-3) + (L037), (I-3) + (L038), (I-3) + (L039), (I-3) + (L040), (I-3) + (L041), (I-3) + (L042), (I-3) + (L043), (I-3) + (L044), (I-3) + (L045), (I-3) + (L046), (I-3) + (L047), (I-3) + (L048), (I-3) + (L049), (I-3) + (L050), (I-3) + (L051), (I-3) + (L052), (I-3) + (L053), (I-3) + (L054), (I-3) + (L055), (I-3) + (L056), (I-3) + (L057), (I-3) + (L058), (I-3) + (L059), (I-3) + (L060), (I-3) + (L061), (I-3) + (L062), (I-3) + (L063), (I-3) + (L064), (I-3) + (L065), (I-3) + (L066), (I-3) + (L067), (I-3) + (L068), (I-3) + (L069), (I-3) + (L070), (I-3) + (L071), (I-3) + (L072), (I-3) + (L073), (I-3) + (L074), (I-3) + (L075), (I-3) + (L076), (I-3) + (L077), (I-3) + (L078), (I-3) + (L079), (I-3) + (L080), (I-3) + (L081), (I-3) + (L082), (I-3) + (L083), (I-3) + (L084), (I-3) + (L085), (I-3) + (L086), (I-3) + (L087), (I-3) + (L088), (I-3) + (L089), (I-3) + (L090), (I-3) + (L091), (I-3) + (L092), (I-3) + (L093), (I-3) + (L094), (I-3) + (L095), (I-3) + (L096), (I-3) + (L097), (I-3) + (L098), (I-3) + (L099), (I-3) + (L100), (I-3) + (L101), (I-3) + (L102), (I-3) + (L103), (I-3) + (L104), (I-3) + (L105), (I-3) + (L106), (I-3) + (L107), (I-3) + (L108), (I-3) + (L109), (I-3) + (L110), (I-3) + (L111), (I-3) + (L112), (I-3) + (L113), (I-3) + (L114), (I-3) + (L115), (I-3) + (L116), (I-3) + (L117), (I-3) + (L118), (I-3) + (L119), (I-3) + (L120), (I-3) + (L121), (I-3) + (L122), (I-3) + (L123), (I-3) + (L124), (I-

TABLE 3-continued

| |
|---|
| 3) + (L125), (I-3) + (L126), (I-3) + (L127), (I-3) + (L128), (I-3) + (L129), (I-3) + (L130), (I-3) + (L131), (I- |
| 3) + (L132), (I-3) + (L133), (I-3) + (L134), (I-3) + (L135), (I-3) + (L136), (I-3) + (L137), (I-3) + (L138), (I- |
| 3) + (L139), (I-3) + (L140), (I-3) + (L141), (I-3) + (L142), (I-3) + (L143), (I-3) + (L144), (I-3) + (L145), (I- |
| 3) + (L146), (I-3) + (L147), (I-3) + (L148), (I-3) + (L149), (I-3) + (L150), (I-3) + (L151), (I-3) + (L152), (I- |
| 3) + (L153), (I-3) + (L154), (I-3) + (L155), (I-3) + (L156), (I-3) + (L157), (I-3) + (L158), (I-3) + (L159), (I- |
| 3) + (L160), (I-3) + (L161), (I-3) + (L162), (I-3) + (L163), (I-3) + (L164), (I-3) + (L165), (I-3) + (L166), (I- |
| 3) + (L167), (I-3) + (L168), (I-3) + (L169), (I-3) + (L170), (I-3) + (L171), (I-3) + (L172), (I-3) + (L173), (I- |
| 3) + (L174), (I-3) + (L175), (I-3) + (L176), (I-3) + (L177), (I-3) + (L178), (I-3) + (L179), (I-3) + (L180), (I- |
| 3) + (L181), (I-3) + (L182), (I-3) + (L183), (I-3) + (L184), (I-3) + (L185), (I-3) + (L186), (I-3) + (L187), (I- |
| 3) + (L188), (I-3) + (L189), (I-3) + (L190), (I-3) + (L191), (I-3) + (L192), (I-3) + (L193), (I-3) + (L194), (I- |
| 3) + (L195), (I-3) + (L196), (I-3) + (L197), (I-3) + (L198), (I-3) + (L199), (I-3) + (L200), (I-3) + (L201), (I- |
| 3) + (L202), (I-3) + (L203), (I-3) + (L204), (I-3) + (L205), (I-3) + (L206), (I-3) + (L207), (I-3) + (L208), (I- |
| 3) + (L209), (I-3) + (L210), (I-3) + (L211), (I-3) + (L212), (I-3) + (L213), (I-3) + (L214), (I-3) + (L215), (I- |
| 3) + (L216), (I-3) + (L217), (I-3) + (L218), (I-3) + (L219), (I-3) + (L220), (I-3) + (L221), (I-3) + (L222), (I- |
| 3) + (L223), (I-3) + (L224), (I-3) + (L225), (I-3) + (L226), (I-3) + (L227), (I-3) + (L228), (I-3) + (L229), (I- |
| 3) + (L230), (I-3) + (L231), (I-3) + (L232), (I-3) + (L233), (I-3) + (L234), (I-3) + (L235), (I-3) + (L236), (I- |
| 3) + (L237), (I-3) + (L238), (I-3) + (L239), (I-3) + (L240), (I-3) + (L241), (I-3) + (L242), (I-3) + (L243), (I- |
| 3) + (L244), (I-3) + (L245), (I-3) + (L246), (I-3) + (L247), (I-3) + (L248), (I-3) + (L249), (I-3) + (L250), (I- |
| 3) + (L251), (I-3) + (L252), (I-3) + (L253), (I-3) + (L254), (I-3) + (L255), (I-3) + (L256), (I-3) + (L257), (I- |
| 3) + (L258), (I-3) + (L259), (I-3) + (L260), (I-3) + (L261), (I-3) + (L262), (I-3) + (L263), (I-3) + (L264), (I- |
| 3) + (L265), (I-3) + (L266), (I-3) + (L267), (I-3) + (L268), (I-3) + (L269), (I-3) + (L270), (I-3) + (L271), (I- |
| 3) + (L272), (I-3) + (L273), (I-3) + (L274), (I-3) + (L275), (I-3) + (L276), (I-3) + (L277), (I-3) + (L278), (I- |
| 3) + (L279), (I-3) + (L280), (I-3) + (L281), (I-3) + (L282), (I-3) + (L283), (I-3) + (L284), (I-3) + (L285), (I- |
| 3) + (L286), (I-3) + (L287), (I-3) + (L288), (I-3) + (L289), (I-3) + (L290), (I-3) + (L291), (I-3) + (L292), (I- |
| 3) + (L293), (I-3) + (L294), (I-3) + (L295), (I-3) + (L296), (I-3) + (L297), (I-3) + (L298), (I-3) + (L299), (I- |
| 3) + (L300), (I-3) + (L301), (I-3) + (L302), (I-3) + (L303), (I-3) + (L304), (I-3) + (L305), (I-3) + (L306), (I- |
| 3) + (L307), (I-3) + (L308), (I-3) + (L309), (I-3) + (L310), (I-3) + (L311), (I-3) + (L312), (I-3) + (L313), (I- |
| 3) + (L314), (I-3) + (L315), (I-3) + (L316), (I-3) + (L317), (I-3) + (L318), (I-3) + (L319), (I-3) + (L320), (I- |
| 3) + (L321), (I-3) + (L322), (I-3) + (L323), (I-3) + (L324), (I-3) + (L325), (I-3) + (L326), (I-3) + (L327), (I- |
| 3) + (L328), (I-3) + (L329), (I-3) + (L330), (I-3) + (L331), (I-3) + (L332), (I-3) + (L333), (I-3) + (L334), (I- |
| 3) + (L335), (I-3) + (L336), (I-3) + (L337), (I-3) + (L338), (I-3) + (L339), (I-3) + (L340), (I-3) + (L341), (I- |
| 3) + (L342), (I-3) + (L343), (I-3) + (L344), (I-3) + (L345), (I-3) + (L346), (I-3) + (L347), (I-3) + (L348), (I- |
| 3) + (L349), (I-3) + (L350), (I-3) + (L351), (I-3) + (L352), (I-3) + (L353), (I-3) + (L354), (I-3) + (L355), (I- |
| 3) + (L356), (I-3) + (L357), (I-3) + (L358), (I-3) + (L359), (I-3) + (L360), (I-3) + (L361), (I-3) + (L362). |

In one embodiment, the weight ratio of component (1) to component (2) is between 100:1 and 1:100 in combinations [(I-3)+(A001] to [(I-3)+(L362)] of Table: 3.

In one embodiment, the weight ratio of component (1) to component (2) is between 50:1 and 1:50 in combinations [(I-3)+(A001] to [(I-3)+(L362)] of Table: 3.

In one embodiment, the weight ratio of component (1) to component (2) is between 20:1 and 1:20 in combinations [(I-3)+(A001] to [(I-3)+(L362)] of Table: 3.

In one embodiment, the weight ratio of component (1) to component (2) is between 5:1 and 1:5 in combinations [(I-3)+(A001] to [(I-3)+(L362)] of Table: 3.

In one embodiment, the weight ratio of component (1) to component (2) is between 3:1 and 1:3 in combinations [(I-3)+(A001] to [(I-3)+(L362)] of Table: 3.

In one embodiment, the weight ratio of component (1) to component (2) is 1:1 in combinations [(I-3)+(A001] to [(I-3)+(L362)] of Table: 3.

Following combinations are listed in Table-4, wherein component (1) is a compound of formula (I-8) and another component (2) is selected from the groups A) to L) as defined herein (component 2, for example, (A001 or azoxystrobin, in combination [(I-8)+(A001)].

TABLE 4

| |
|---|
| -8) + (A001), (I-8) + (A002), (I-8) + (A003), (I-8) + (A004), (I-8) + (A005), (I-8) + (A006), (I-8) + (A007), (I- |
| 8) + (A008), (I-8) + (A009), (I-8) + (A010), (I-8) + (A011), (I-8) + (A012), (I-8) + (A013), (I-8) + (A014), (I- |
| 8) + (A015), (I-8) + (A016), (I-8) + (A017), (I-8) + (A018), (I-8) + (A019), (I-8) + (A020), (I-8) + (A021), (I- |
| 8) + (A022), (I-8) + (A023), (I-8) + (A024), (I-8) + (A025), (I-8) + (A026), (I-8) + (A027), (I-8) + (A028), (I- |
| 8) + (A029), (I-8) + (A030), (I-8) + (A031), (I-8) + (A032), (I-8) + (A033), (I-8) + (A034), (I-8) + (A035), (I- |
| 8) + (A036), (I-8) + (A037), (I-8) + (A038), (I-8) + (A039), (I-8) + (A040), (I-8) + (A041), (I-8) + (A042), (I- |
| 8) + (A043), (I-8) + (A044), (I-8) + (A045), (I-8) + (A046), (I-8) + (A047), (I-8) + (A048), (I-8) + (A049), (I- |
| 8) + (A050), (I-8) + (A051), (I-8) + (A052), (I-8) + (A053), (I-8) + (A054), (I-8) + (A055), (I-8) + (A056), (I- |
| 8) + (A057), (I-8) + (A058), (I-8) + (A059), (I-8) + (A060), (I-8) + (A061), (I-8) + (A062), (I-8) + (A063), (I- |
| 8) + (A064), (I-8) + (A065), (I-8) + (A066), (I-8) + (A067), (I-8) + (A068), (I-8) + (A069), (I-8) + (A070), (I- |
| 8) + (A071), (I-8) + (A072), (I-8) + (A073), (I-8) + (A074), (I-8) + (A075), (I-8) + (A076), (I-8) + (A077), (I- |
| 8) + (A078), (I-8) + (A079), (I-8) + (A080), (I-8) + (A081), (I-8) + (A082), (I-8) + (A083), (I-8) + (A084), (I- |
| 8) + (A085), (I-8) + (A086), (I-8) + (A087), (I-8) + (A088), (I-8) + (A089), (I-8) + (A090), (I-8) + (A091), (I- |
| 8) + (A092), (I-8) + (A093), (I-8) + (A094), (I-8) + (A095), (I-8) + (A096), (I-8) + (A097), (I-8) + (A098), (I- |
| 8) + (A099), (I-8) + (A100), (I-8) + (A101), (I-8) + (A102), (I-8) + (A103), (I-8) + (A104), (I-8) + (B001), (I- |
| 8) + (B002), (I-8) + (B003), (I-8) + (B004), (I-8) + (B005), (I-8) + (B006), (I-8) + (B007), (I-8) + (B008), (I- |
| 8) + (B009), (I-8) + (B010), (I-8) + (B011), (I-8) + (B012), (I-8) + (B013), (I-8) + (B014), (I-8) + (B015), (I- |
| 8) + (B016), (I-8) + (B017), (I-8) + (B018), (I-8) + (B019), (I-8) + (B020), (I-8) + (B021), (I-8) + (B022), (I- |
| 8) + (B023), (I-8) + (B024), (I-8) + (B025), (I-8) + (B026), (I-8) + (B027), (I-8) + (B028), (I-8) + (B029), (I- |
| 8) + (B030), (I-8) + (B031), (I-8) + (B032), (I-8) + (B033), (I-8) + (B034), (I-8) + (B035), (I-8) + (B036), (I- |
| 8) + (B037), (I-8) + (B038), (I-8) + (B039), (I-8) + (B040), (I-8) + (B041), (I-8) + (B042), (I-8) + (B043), (I- |
| 8) + (B044), (I-8) + (B045), (I-8) + (B046), (I-8) + (B047), (I-8) + (B048), (I-8) + (B049), (I-8) + (B050), (I- |
| 8) + (B051), (I-8) + (B052), (I-8) + (B053), (I-8) + (B054), (I-8) + (B055), (I-8) + (B056), (I-8) + (B057), (I- |
| 8) + (B058), (I-8) + (B059), (I-8) + (B060), (I-8) + (B061), (I-8) + (B062), (I-8) + (C001), (I-8) + (C002), (I- |
| 8) + (C003), (I-8) + (C004), (I-8) + (C005), (I-8) + (C006), (I-8) + (C007), (I-8) + (C008), (I-8) + (C009), (I- |

TABLE 4-continued

8) + (C010), (I-8) + (C011), (I-8) + (C012), (I-8) + (C013), (I-8) + (C014), (I-8) + (C015), (I-8) + (D001), (I-
8) + (D002), (I-8) + (D003), (I-8) + (D004), (I-8) + (D005), (I-8) + (D006), (I-8) + (D007), (I-8) + (D008), (I-
8) + (D009), (I-8) + (D010), (I-8) + (D011), (I-8) + (D012), (I-8) + (D013), (I-8) + (D014), (I-8) + (D015), (I-
8) + (D016), (I-8) + (D017), (I-8) + (D018), (I-8) + (D019), (I-8) + (D020), (I-8) + (D021), (I-8) + (D022), (I-
8) + (D023), (I-8) + (E001), (I-8) + (E002), (I-8) + (E003), (I-8) + (E004), (I-8) + (E005), (I-8) + (E006), (I-
8) + (E007), (I-8) + (E008), (I-8) + (E009), (I-8) + (F001), (I-8) + (F002), (I-8) + (F003), (I-8) + (F004), (I-
8) + (F005), (I-8) + (F006), (I-8) + (F007), (I-8) + (G001), (I-8) + (G002), (I-8) + (G003), (I-8) + (G004), (I-
8) + (G005), (I-8) + (G006), (I-8) + (G007), (I-8) + (G008), (I-8) + (G009), (I-8) + (G010), (I-8) + (G011), (I-
8) + (G012), (I-8) + (G013), (I-8) + (G014), (I-8) + (G015), (I-8) + (G016), (I-8) + (G017), (I-8) + (G018), (I-
8) + (G019), (I-8) + (G020), (I-8) + (G021), (I-8) + (G022), (I-8) + (G023), (I-8) + (G024), (I-8) + (G025), (I-
8) + (G026), (I-8) + (G027), (I-8) + (G028), (I-8) + (G029), (I-8) + (G030), (I-8) + (G031), (I-8) + (H001), (I-
8) + (H002), (I-8) + (H003), (I-8) + (H004), (I-8) + (H005), (I-8) + (H006), (I-8) + (H007), (I-8) + (H008), (I-
8) + (H009), (I-8) + (H010), (I-8) + (H011), (I-8) + (H012), (I-8) + (H013), (I-8) + (H014), (I-8) + (H015), (I-
8) + (H016), (I-8) + (H017), (I-8) + (H018), (I-8) + (H019), (I-8) + (H020), (I-8) + (H021), (I-8) + (H022), (I-
8) + (H023), (I-8) + (H024), (I-8) + (H025), (I-8) + (H026), (I-8) + (H027), (I-8) + (H028), (I-8) + (H029), (I-
8) + (H030), (I-8) + (H031), (I-8) + (H032), (I-8) + (H033), (I-8) + (H034), (I-8) + (H035), (I-8) + (H036), (I-
8) + (H037), (I-8) + (I001), (I-8) + (I002), (I-8) + (I003), (I-8) + (I004), (I-8) + (I005), (I-8) + (I006), (I-8) + (I007),
(I-8) + (J001), (I-8) + (J002), (I-8) + (J003), (I-8) + (J004), (I-8) + (J005), (I-8) + (J006), (I-8) + (J007), (I-
8) + (J008), (I-8) + (J009), (I-8) + (J010), (I-8) + (J011), (I-8) + (J012), (I-8) + (K001), (I-8) + (K002), (I-
8) + (K003), (I-8) + (K004), (I-8) + (K005), (I-8) + (K006), (I-8) + (K007), (I-8) + (K008), (I-8) + (K009), (I-
8) + (K010), (I-8) + (K011), (I-8) + (K012), (I-8) + (K013), (I-8) + (K014), (I-8) + (K015), (I-8) + (K016), (I-
8) + (K017), (I-8) + (K018), (I-8) + (K019), (I-8) + (K020), (I-8) + (K021), (I-8) + (K022), (I-8) + (K023), (I-
8) + (K024), (I-8) + (K025), (I-8) + (K026), (I-8) + (K027), (I-8) + (K028), (I-8) + (K029), (I-8) + (K030), (I-
8) + (K031), (I-8) + (K032), (I-8) + (K033), (I-8) + (K034), (I-8) + (K035), (I-8) + (K036), (I-8) + (K037), (I-
8) + (K038), (I-8) + (K039), (I-8) + (K040), (I-8) + (K041), (I-8) + (K042), (I-8) + (K043), (I-8) + (K044), (I-
8) + (K045), (I-8) + (K046), (I-8) + (K047), (I-8) + (K048), (I-8) + (K049), (I-8) + (K050), (I-8) + (K051), (I-
8) + (K052), (I-8) + (K053), (I-8) + (K054), (I-8) + (K055), (I-8) + (K056) (I-8) + (K055), (I-8) + (K056), (I-
8) + (K057), (I-8) + (K058), (I-8) + (K059), (I-8) + (K060), (I-8) + (K061), (I-8) + (K062), (I-8) + (K063), (I-
8) + (K064), (I-8) + (L001), (I-8) + (L002), (I-8) + (L003), (I-8) + (L004), (I-8) + (L005), (I-8) + (L006), (I-
8) + (L007), (I-8) + (L008), (I-8) + (L009), (I-8) + (L010), (I-8) + (L011), (I-8) + (L012), (I-8) + (L013), (I-
8) + (L014), (I-8) + (L015), (I-8) + (L016), (I-8) + (L017), (I-8) + (L018), (I-8) + (L019), (I-8) + (L020), (I-
8) + (L021), (I-8) + (L022), (I-8) + (L023), (I-8) + (L024), (I-8) + (L025), (I-8) + (L026), (I-8) + (L027), (I-
8) + (L028), (I-8) + (L029), (I-8) + (L030), (I-8) + (L031), (I-8) + (L032), (I-8) + (L033), (I-8) + (L034), (I-
8) + (L035), (I-8) + (L036), (I-8) + (L037), (I-8) + (L038), (I-8) + (L039), (I-8) + (L040), (I-8) + (L041), (I-
8) + (L042), (I-8) + (L043), (I-8) + (L044), (I-8) + (L045), (I-8) + (L046), (I-8) + (L047), (I-8) + (L048), (I-
8) + (L049), (I-8) + (L050), (I-8) + (L051), (I-8) + (L052), (I-8) + (L053), (I-8) + (L054), (I-8) + (L055), (I-
8) + (L056), (I-8) + (L057), (I-8) + (L058), (I-8) + (L059), (I-8) + (L060), (I-8) + (L061), (I-8) + (L062), (I-
8) + (L063), (I-8) + (L064), (I-8) + (L065), (I-8) + (L066), (I-8) + (L067), (I-8) + (L068), (I-8) + (L069), (I-
8) + (L070), (I-8) + (L071), (I-8) + (L072), (I-8) + (L073), (I-8) + (L074), (I-8) + (L075), (I-8) + (L076), (I-
8) + (L077), (I-8) + (L078), (I-8) + (L079), (I-8) + (L080), (I-8) + (L081), (I-8) + (L082), (I-8) + (L083), (I-
8) + (L084), (I-8) + (L085), (I-8) + (L086), (I-8) + (L087), (I-8) + (L088), (I-8) + (L089), (I-8) + (L090), (I-
8) + (L091), (I-8) + (L092), (I-8) + (L093), (I-8) + (L094), (I-8) + (L095), (I-8) + (L096), (I-8) + (L097), (I-
8) + (L098), (I-8) + (L099), (I-8) + (L100), (I-8) + (L101), (I-8) + (L102), (I-8) + (L103), (I-8) + (L104), (I-
8) + (L105), (I-8) + (L106), (I-8) + (L107), (I-8) + (L108), (I-8) + (L109), (I-8) + (L110), (I-8) + (L111), (I-
8) + (L112), (I-8) + (L113), (I-8) + (L114), (I-8) + (L115), (I-8) + (L116), (I-8) + (L117), (I-8) + (L118), (I-
8) + (L119), (I-8) + (L120), (I-8) + (L121), (I-8) + (L122), (I-8) + (L123), (I-8) + (L124), (I-8) + (L125), (I-
8) + (L126), (I-8) + (L127), (I-8) + (L128), (I-8) + (L129), (I-8) + (L130), (I-8) + (L131), (I-8) + (L132), (I-
8) + (L133), (I-8) + (L134), (I-8) + (L135), (I-8) + (L136), (I-8) + (L137), (I-8) + (L138), (I-8) + (L139), (I-
8) + (L140), (I-8) + (L141), (I-8) + (L142), (I-8) + (L143), (I-8) + (L144), (I-8) + (L145), (I-8) + (L146), (I-
8) + (L147), (I-8) + (L148), (I-8) + (L149), (I-8) + (L150), (I-8) + (L151), (I-8) + (L152), (I-8) + (L153), (I-
8) + (L154), (I-8) + (L155), (I-8) + (L156), (I-8) + (L157), (I-8) + (L158), (I-8) + (L159), (I-8) + (L160), (I-
8) + (L161), (I-8) + (L162), (I-8) + (L163), (I-8) + (L164), (I-8) + (L165), (I-8) + (L166), (I-8) + (L167), (I-
8) + (L168), (I-8) + (L169), (I-8) + (L170), (I-8) + (L171), (I-8) + (L172), (I-8) + (L173), (I-8) + (L174), (I-
8) + (L175), (I-8) + (L176), (I-8) + (L177), (I-8) + (L178), (I-8) + (L179), (I-8) + (L180), (I-8) + (L181), (I-
8) + (L182), (I-8) + (L183), (I-8) + (L184), (I-8) + (L185), (I-8) + (L186), (I-8) + (L187), (I-8) + (L188), (I-
8) + (L189), (I-8) + (L190), (I-8) + (L191), (I-8) + (L192), (I-8) + (L193), (I-8) + (L194), (I-8) + (L195), (I-
8) + (L196), (I-8) + (L197), (I-8) + (L198), (I-8) + (L199), (I-8) + (L200), (I-8) + (L201), (I-8) + (L202), (I-
8) + (L203), (I-8) + (L204), (I-8) + (L205), (I-8) + (L206), (I-8) + (L207), (I-8) + (L208), (I-8) + (L209), (I-
8) + (L210), (I-8) + (L211), (I-8) + (L212), (I-8) + (L213), (I-8) + (L214), (I-8) + (L215), (I-8) + (L216), (I-
8) + (L217), (I-8) + (L218), (I-8) + (L219), (I-8) + (L220), (I-8) + (L221), (I-8) + (L222), (I-8) + (L223), (I-
8) + (L224), (I-8) + (L225), (I-8) + (L226), (I-8) + (L227), (I-8) + (L228), (I-8) + (L229), (I-8) + (L230), (I-
8) + (L231), (I-8) + (L232), (I-8) + (L233), (I-8) + (L234), (I-8) + (L235), (I-8) + (L236), (I-8) + (L237), (I-
8) + (L238), (I-8) + (L239), (I-8) + (L240), (I-8) + (L241), (I-8) + (L242), (I-8) + (L243), (I-8) + (L244), (I-
8) + (L245), (I-8) + (L246), (I-8) + (L247), (I-8) + (L248), (I-8) + (L249), (I-8) + (L250), (I-8) + (L251), (I-
8) + (L252), (I-8) + (L253), (I-8) + (L254), (I-8) + (L255), (I-8) + (L256), (I-8) + (L257), (I-8) + (L258), (I-
8) + (L259), (I-8) + (L260), (I-8) + (L261), (I-8) + (L262), (I-8) + (L263), (I-8) + (L264), (I-8) + (L265), (I-
8) + (L266), (I-8) + (L267), (I-8) + (L268), (I-8) + (L269), (I-8) + (L270), (I-8) + (L271), (I-8) + (L272), (I-
8) + (L273), (I-8) + (L274), (I-8) + (L275), (I-8) + (L276), (I-8) + (L277), (I-8) + (L278), (I-8) + (L279), (I-
8) + (L280), (I-8) + (L281), (I-8) + (L282), (I-8) + (L283), (I-8) + (L284), (I-8) + (L285), (I-8) + (L286), (I-
8) + (L287), (I-8) + (L288), (I-8) + (L289), (I-8) + (L290), (I-8) + (L291), (I-8) + (L292), (I-8) + (L293), (I-
8) + (L294), (I-8) + (L295), (I-8) + (L296), (I-8) + (L297), (I-8) + (L298), (I-8) + (L299), (I-8) + (L300), (I-
8) + (L301), (I-8) + (L302), (I-8) + (L303), (I-8) + (L304), (I-8) + (L305), (I-8) + (L306), (I-8) + (L307), (I-
8) + (L308), (I-8) + (L309), (I-8) + (L310), (I-8) + (L311), (I-8) + (L312), (I-8) + (L313), (I-8) + (L314), (I-
8) + (L315), (I-8) + (L316), (I-8) + (L317), (I-8) + (L318), (I-8) + (L319), (I-8) + (L320), (I-8) + (L321), (I-

TABLE 4-continued

| |
|---|
| 8) + (L322), (I-8) + (L323), (I-8) + (L324), (I-8) + (L325), (I-8) + (L326), (I-8) + (L327), (I-8) + (L328), (I-8) + (L329), (I-8) + (L330), (I-8) + (L331), (I-8) + (L332), (I-8) + (L333), (I-8) + (L334), (I-8) + (L335), (I-8) + (L336), (I-8) + (L337), (I-8) + (L338), (I-8) + (L339), (I-8) + (L340), (I-8) + (L341), (I-8) + (L342), (I-8) + (L343), (I-8) + (L344), (I-8) + (L345), (I-8) + (L346), (I-8) + (L347), (I-8) + (L348), (I-8) + (L349), (I-8) + (L350), (I-8) + (L351), (I-8) + (L352), (I-8) + (L353), (I-8) + (L354), (I-8) + (L355), (I-8) + (L356), (I-8) + (L357), (I-8) + (L358), (I-8) + (L359), (I-8) + (L360), (I-8) + (L361), (I-8) + (L362). |

In one embodiment, the weight ratio of component (1) to component (2) is between 100:1 and 1:100 in combinations [(I-8)+(A001] to [(I-8)+(L362)] of Table: 4.

In one embodiment, the weight ratio of component (1) to component (2) is between 50:1 and 1:50 in combinations [(I-8)+(A001] to [(I-8)+(L362)] of Table: 4.

In one embodiment, the weight ratio of component (1) to component (2) is between 20:1 and 1:20 in combinations [(I-8)+(A001] to [(I-8)+(L362)] of Table: 4.

In one embodiment, the weight ratio of component (1) to component (2) is between 5:1 and 1:5 in combinations [(I-8)+(A001] to [(I-8)+(L362)] of Table: 4.

In one embodiment, the weight ratio of component (1) to component (2) is between 3:1 and 1:3 in combinations [(I-8)+(A001] to [(I-8)+(L362)] of Table: 4.

In one embodiment, the weight ratio of component (1) to component (2) is 1:1 in combinations [(I-8)+(A001] to [(I-8)+(L362)] of Table: 4.

Table: 5

The combination of [(I-1)+(A001] to [(I-1)+(L362)] are defined as combination [(I-2)+(A001] to [(I-2)+(L362)] of Table 2, wherein compound (I-2) in each mixture is replaced with compound (I-1).

Table: 6

The combination of [(I-4)+(A001] to [(I-4)+(L362)] are defined as combination [(I-2)+(A001] to [(I-2)+(L362)] of Table 2, wherein compound (I-2) in each mixture is replaced with compound (I-4).

Table: 7

The combination [(I-5)+(A001] to [(I-5)+(L362)] are defined as combination [(I-2)+(A001] to [(I-2)+(L362)] of Table 2, wherein compound (I-2) in each mixture is replaced with compound (I-5).

Table: 8

The combination [(I-6)+(A001] to [(I-6)+(L362)] are defined as combination [(I-2)+(A001] to [(I-2)+(L362)] of Table 2, wherein compound (I-2) in each mixture is replaced with compound (I-6).

Table: 9

The combination [(I-7)+(A001] to [(I-7)+(L362)] are defined as combination [(I-2)+(A001] to [(I-2)+(L362)] of Table 2, wherein compound (I-2) in each mixture is replaced with compound (I-7).

In one embodiment, the present invention provides fungicidal compositions comprising as active components 1) at least one active compound of formula (I), or an N-oxide, or an agriculturally acceptable salt thereof; and as component 2) at least one active compound II selected from groups A) to L) as defined above, or an N-oxide, or an agriculturally acceptable salt thereof; and as component 3) at least one active compound III selected from groups A) to L) as defined for component 2), or an N-oxide, or an agriculturally acceptable salt thereof; wherein the at least one active compound III of component 3) is not identical with the at least one active compound II of component 2).

The invention also relates to a method for controlling phytopathogenic harmful fungi using the abovementioned ternary mixtures; to agrochemical compositions comprising these ternary mixtures; and to a seed comprising these mixtures.

In one embodiment, the present invention provides the use of the fungicidal composition for controlling phytopathogenic harmful fungi.

More specifically, the novel fungicidal compositions of the present invention can be used as fungicides. In particular, they can be useful in crop protection, for example for the control of unwanted fungi, such as Plasmodiophoromycetes, Oomycetes, Chytridiomycetes, Zygomycetes, Ascomycetes, Basidiomycetes and Deuteromycetes.

The fungicidal composition of the present invention can also be used as a bactericide. In particular, they can be used in crop protection, for example for the control of unwanted bacteria, such as Pseudomonadaceae, Rhizobiaceae, Enterobacteriaceae, Corynebacteriaceae and Streptomycetaceae.

In a preferred embodiment, the fungicidal compositions disclosed in table-1 and in particular when the weight ratios of component (1) to component (2) are as disclosed for these mixtures as herein mentioned before, are used against crop phytopathogenic fungi like *Alternaria* species, for example *Alternaria solani; Erysiphe* spp. (e.g. *Erysiphe cichoracearum*); *Botrytis* species, for example, *Botrytis cinerea* on fruits and berries; *Corynespora cassiicola, Cercospora* sojina and *C. kukuchii* (leaf spots) on soybeans and ornamentals; *Pseudoperonospora cubensis* (downy mildew of cucurbits) on vrious vegetables; *Pyricularia* species, for example *Pyricularia oryzae; Septoria* species, for example *Septoria nodorum, Puccinia* spp. (rusts) on various plants, in particular *P. triticina* (brown or leaf rust), *P. striiformis* (stripe or yellow rust), *P. hordei* (dwarf rust), *P. graminis* (stem or black rust) or *P. recondita* (brown or leaf rust), on cereals selected from wheat, barley or rye, *P. coronata* (crown rust of grasses including oats) on cereals, such as e.g. wheat, barley or rye, and *Puccinia sorghi* (common rust) on maize, *Puccinia polysora* (southern rust) on maize, and *P. helianthi* (sunflower rust); *Puccinia melanocephala* ('Brown rust' in sugarcane); *Hemileia vastatrix* and *Hemileia coffeicola* (leaf rust and grey rust of coffee) *Hemileia vastatrix* (Coffee rust); *Uromyces* spp. on various crops; and Phakopsoraceae spp. on various plants, in particular *Phakopsora pachyrhizi* and *P. meibomiae* (soybean rust) on soybeans.

In another preferred embodiment, the fungicidal compositions according to the present invention comprising a compound of Formula (I), are used against *Phakopsora pachyrhizi* and *P. meibomide* on soybeans and/or against *Puccinia triticina, P. striiformis, P. horde, P. graminis* or *P. recondita* on wheat, barley or rye as well as *Hemileia vastatrix* and *Hemileia coffeicola* on coffee. *Puccinia melanocephala* on sugarcane and *Uromyces* spp. on various crops.

In one another preferred embodiment, the fungicidal compositions according to the present invention comprising a compound of Formula (I), are used against *Alternaria solani, Botrytis cinerea, Phakopsora pachyrhizi. Septoria*

*nodorum. Erysiphe cichoracearum, Pyricularia oryzae. Corynespora cassiicola, Cercospora* sojina and *Pseudoperonospora cubensis.*

In one embodiment, the present invention provides a method for controlling or preventing infestation of useful plants by phytopathogenic fungi in agricultural crops and/or horticultural crops, wherein the fungicidal composition is applied to the plants, to parts thereof or to a locus thereof.

The fungicidal compositions according to the invention have a potent microbicidal activity. They can be used for controlling unwanted microorganisms, such as unwanted fungi and bacteria. They can be particularly useful in crop protection (they control microorganisms that cause plants diseases). More specifically, the fungicidal composition of the present invention can be used to protect seeds, germinating plants, emerged seedlings, plants, plant parts, fruits and the soil in which the plants grow from unwanted microorganisms.

The term "Control" or "Controlling" as used herein encompasses curative and protective treatment of unwanted microorganisms. The unwanted microorganisms may be pathogenic bacteria or pathogenic fungi, more specifically phytopathogenic bacteria or phytopathogenic fungi. As detailed herein below, these phytopathogenic microorganisms are the causal agents of a broad spectrum of plants diseases.

In one embodiment, the invention relates to a method for controlling phytopathogenic harmful fungi using mixtures comprising as component 1) of at least one compound of the formula (I) and comprising as component 2) at least one active compound in a weight ratio of from 100:1 to 1:100; to the use of fungicidal compositions comprising compounds of formula (I) for controlling phytopathogenic harmful fungi; to fungicidal compositions comprising these mixtures; and to fungicidal compositions further comprising seed.

The present invention also relates to a method for controlling unwanted microorganisms, such as unwanted fungi and bacteria, comprising the step of applying a fungicidal composition according to the present invention to the microorganisms and/or their habitat (to the plants, plant parts, seeds, fruits or to the soil in which the plants grow).

In one embodiment, the present invention provides a method for controlling or preventing phytopathogenic fungi, comprising treating plants, soil, seeds or materials to be protected with the fungicidal composition as described herein.

In another embodiment, the present invention provides a method for controlling phytopathogenic harmful fungi, comprising treating the plants, their habitat or the seed, the soil or the plants for the protection against fungal attack with an effective and non-phytotoxic amount of the fungicidal composition of the present invention.

The fungicidal compositions of the present invention can be used for curative or protective/preventive control of phytopathogenic fungi. The present invention therefore also relates to curative and protective methods for controlling phytopathogenic fungi by the use of the fungicidal compositions, which are applied to the seeds, the plants or plant parts, the fruits or the soil in which the plants grow.

The fact that the novel fungicidal compositions according to the invention are well tolerated by plants at the concentrations required for controlling plant diseases allows the treatment of above-ground parts of plants, of propagation stock and seeds, and of the soil.

The fungicidal compositions according to the invention, which are well tolerated by plants, have favorable homeotherm toxicity and are well tolerated by the environment, are suitable for protecting plants and plant organs, for enhancing harvest yields and improving the quality of the harvested material. They can preferably be used as crop protection compositions. They are active against normally sensitive and resistant species and against all or some stages of development.

Typically, when the fungicidal compositions according to the invention are used in curative or protective methods for controlling phytopathogenic fungi, an effective and non-phytotoxic amount thereof is applied to the plants, plant parts, fruits, seeds or to the soil in which the plants grow.

Effective and non-phytotoxic amount means an amount that is sufficient to control or destroy the fungi present or liable to appear on the cropland and that does not entail any symptoms of phytotoxicity for said crops. Such an amount can vary within a wide range depending on the fungus to be controlled, the type of crop, the climatic conditions and the respective composition of the invention used. This amount can be determined by systematic field trials that are within the capabilities of a person skilled in the art.

The fungicidal composition according to the present invention can be applied to any plants or plant parts.

In one embodiment, the present invention provides a fungicidal composition for treating seed, seed of transgenic plants and transgenic plants.

Plants mean all plants and plant populations, such as desired and undesired wild plants or crop plants (including naturally occurring crop plants). The crop plants are the plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Genetically modified plants (GMO or transgenic plants) are the plants in which a heterologous gene has been stably integrated into the genome. The expression "heterologous gene" essentially means a gene which is provided or assembled outside the plant and then introduced in the nuclear, chloroplastic or mitochondrial genome. This gene gives the transformed plant new or improved agronomic or other properties by expressing a protein or polypeptide of interest or by down regulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plant cultivars are understood to mean plants which have new properties ("traits") and have been obtained by conventional breeding, by mutagenesis or by recombinant DNA techniques. They can be cultivars, varieties, bio- or genotypes.

Plant parts are understood to mean all parts and organs of plants above and below the ground, such as shoots, leaves, needles, stalks, stems, flowers, fruit bodies, fruits, seeds, roots, tubers and rhizomes. The plant parts also include harvested material, vegetative and generative propagation material, for example cuttings, tubers, rhizomes, slips and seeds.

Application of the compounds of the present disclosure or the compound of the present disclosure in a composition optionally comprising other compatible compounds to a plant or a plant material or locus thereof include application by a technique known to a person skilled in the art which includes but is not limited to spraying, coating, dipping, fumigating, impregnating, injection and dusting.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Aforaceae sp., Oleaceae sp. (e.g. olive tree), Actinidaceae sp., Lauraceae sp. (e.g. avocado, cinnamon, camphor), Afusaceae sp. (e.g. banana trees and plantations), Rubiaceae sp. (e.g. coffee), Theaceae sp. (e.g. tea), Sterculiceae sp., Rutaceae sp. (e.g. lemons, oranges, mandarins and grapefruit); Solanaceae sp. (e.g. tomatoes, potatoes, peppers, capsicum, aubergines, tobacco), Liliaceae sp., Compositae sp. (e.g. lettuce, artichokes and chicory—including root chicmy, endive or common chicory), Umbelliferae sp. (e.g. carrots, parsley, celery and celeriac), Cucurbitaceae sp. (e.g. cucumbers—including gherkins, pumpkins, watermelons, calabashes and melons), Alliaceae sp. (e.g. leeks and onions, shallots), Cruciferae sp. (e.g. white cabbage, red cabbage, broccoli, cauliflower, Brussels sprouts, pak choi, kohlrabi, radishes, horseradish, cress and chinese cabbage), Leguminosae sp. (e.g. peanuts, peas, lentils and beans—e.g. common beans and broad beans), Chenopodiaceae sp. (e.g. Swiss chard, fodder beet, spinach, beetroot), Linaceae sp. (e.g. hemp), Cannabeacea sp. (e.g. *cannabis*), Malvaceae sp. (e.g. okra, cocoa), Papaveraceae (e.g. poppy), Asparagaceae (e.g. asparagus); Cannabaceae sp. (hops); useful plants and ornamental plants in the garden and woods including turf, lawn, grass and *Stevia rebaudiana*; and in each case genetically modified types of these plants.

The fungicidal compositions of the present invention may be used to treat several fungal pathogens. Non-limiting examples of pathogens of fungal diseases which can be treated in accordance with the present invention include: diseases caused by powdery mildew pathogens, for example Blumeria species, for example Blumeria *graminis; Podosphaera* species, for example *Podosphaera leucotricha; Sphaerotheca* species, for example *Sphaerotheca fuliginea; Uncinula* species, for example *Uncinula necator; Erysiphe* species, for example *Erysiphe cichoracearu*; diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* or *Puccinia striiformis*, and *Puccinia melanocephala; Uromyces* species, for example *Uromyces appendiculatus*; In particular, *Cronartium ribicola* (White pine blister rust); *Gymnosporangium juniperi-virginianae* (Cedar-apple rust); *Hemileia vastatrix* (Coffee rust); *Phakopsora meibomiae* and *P. pachyrhizi* (Soybean rust); *Puccinia coronata* (Crown Rust of Oats and Ryegrass); *Puccinia graminis* (Stem rust of wheat and Kentucky bluegrass, or black rust of cereals); *Puccinia hemerocallidis* (Daylily rust); *Puccinia persistens* subsp. *triticina* (wheat rust or 'brown or red rust'); *Puccinia sorghi* (rust in corn); *Puccinia striiformis* ('Yellow rust' in cereals); *Puccinia melanocephala; Uromyces appendiculatus* (rust of beans); *Uromyces phaseoli* (Bean rust); *Puccinia melanocephala* ('Brown rust' in sugarcane); *Puccinia kuehnii* ('Orange rust' in sugarcane); diseases caused by pathogens from the group of the Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum*; leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidial form: *Drechslera*, syn: *Helminthosporium*) or *Cochliobolus miyabeanus; Colletotrichum* species, for example *Colletotrichum lindemuthanium; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii* or *Septoria lycopersici; Stagonospora* species, for example *Stagonospora nodorum; Typhula* species, for example *Typhula incarnata; Venturia* species, for example *Venturia inaequalis*; root and stem diseases caused, for example, by *Corticium* species, for example *Corticium graminearum; Fusarium* species, for example *Fusarium oxysporum; Gaeumannomyces* species, for example *Gaeumannomyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium oryzae; Tapesia* species, for example *Tapesia acuformis; Thielaviopsis* species, for example *Thielaviopsis basicola; Ganoderma* species, for example *Ganoderma lucidum*; ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Stagnospora* species, for example *Stagnospora nodorum*; diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda*; fruit rot caused, for example, by *Aspergillus* species, for example *Aspergillus*

*flavus; Botrytis* species, for example *Botrytis cinerea; Penicillium* species, for example *Penicillium expansum* or *Penicillium purpurogenum; Rhizopus* species, for example *Rhizopus stolonifer; Sclerotinia* species, for example *Sclerotinia sclerotiorum; Verticilium* species, for example *Verticilium alboatrum*; seed- and soil-borne rot and wilt diseases, and also diseases of seedlings, caused, for example, by *Alternaria* species, for example *Alternaria brassicicola; Aphanomyces* species, for example *Aphanomyces* euteiches; *Ascochyta* species, for example *Ascochyta* lentis; *Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum* coccodes; *Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma* lingam; *Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum; Typhula* species, for example *Typhula incarnata; Verticillium* species, for example *Verticillium dahliae*; cancers, galls and witches' broom caused, for example, by *Nectria* species, for example *Nectria galligena*; wilt diseases caused, for example, by *Monilinia* species, for example *Monilinia laxa*; deformations of leaves, flowers and fruits caused, for example, by *Exobasidium* species, for example *Exobasidium vexans; Taphrina* species, for example *Taphrina deformans*; degenerative diseases in woody plants, caused, for example, by *Esca* species, for example *Phaeomoniella chlamydospora, Phaeoacremonium aleophilum* or *Fomitiporia mediterranea; Ganoderma* species, for example *Ganoderma* boninense; diseases of flowers and seeds caused, for example, by *Botrytis* species, for example *Botrytis cinerea*; diseases of plant tubers caused, for example, by *Rhizoctonia* species, for example *Rhizoctonia solani; Helminthosporium* species, for example *Helminthosporium solani*; diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Ralstonia* species, for example *Ralstonia solanacearum*; fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum. Pythium ultimum*), *rhizoctonia* root rot, stem decay, and damping-off (*Rhizoctonia solani*), *sclerotinia* stem decay (*Sclerotinia sclerotiorum*), *sclerotinia* southern blight (*Sclerotinia rolfsii*), *thielaviopsis* root rot (*Thielaviopsis basicola*).

More preference is given to controlling the following diseases of soya beans: Fungal diseases on leaves, stems, pods and seeds caused, for example, by *Alternaria* leaf spot (*Altenaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera* glycini), frog-eye leaf spot (*Cercospora* sojina), *leptosphaerulina* leaf spot (*Leptosphaerulina trifolii*), *phyllostica* leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), *rhizoctonia* aerial, foliage, and web blight (*Rhizoctonia solani*), rust (*Phakopsora pachyrhizi, Phakopsora meibomiae*), scab (*Sphaceloma glycines*), *stemphylium* leaf blight (*Stemphylium botryosum*), target spot (*Corynespora cassiicola*).

In particular, the fungicidal compositions of the present invention are suitable for controlling the following plant diseases: *Albugo* spp. (white rust) on ornamentals, vegetables (e.g. *A candida*) and sunflowers (e.g. *A tragopogonis*); *Alternaria* spp. (*Alternaria* leaf spot) on vegetables, rape (*A brassicola* or *brassi cae*), sugar beets (*A tenuis*), fruits, rice, soybeans, potatoes (e.g. *A solani* or *A alternata*), tomatoes (e.g. *A solani* or *A alternata*) and wheat; *Aphanomyces* spp. on sugar beets and vegetables; *Ascochyta* spp. on cereals and vegetables, e.g. *A tritici* (anthracnose) on wheat and *A hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; Blumeria (formerly *Erysiphe*) *graminis* (powdery mildew) on cereals (e.g. on wheat or barley); *Botrytis cinerea* (teleomorph: Botryotinia fuckeliana: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad leaved trees and evergreens, e.g. *C. ulmi* (Dutch elm disease) on elms; *Cercospora* spp. (*Cercospora* leaf spots) on corn (e.g. Gray leaf spot: *C. zeaemaydis*), rice, sugar beets (e.g. *C. beticola*), sugar cane, vegetables, coffee, soybeans (e.g. *C. sojina* or *C. kikuchil*) and rice; *Cladosporium* spp. on tomatoes (e.g. *C, fulvum*: leaf mold) and cereals, e.g. *C. herbarum* (black ear) on wheat; *Claviceps purpurea* (ergot) on cereals; *Cochliobolus* (anamorph: *Helmin thosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypit*), corn (e.g. *C. gramini cola*: Anthracnose stalk rot), fruits, potatoes (e.g. *C. coccodes*: black dot), vegetables like beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot)

on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; *Esca* (dieback, apoplexy) on vines, caused by *Formitiporia* (syn. *Phellinus*) *punctata, F. mediterranea, Phaeomoniella chlamydospora* (earlier *Phaeoacremonium chlamydosporum*). *Phaeoacremonium aleophilum* and/or *Botryosphaeria obtusa; Elsinoe* spp. on pome fruits (*E. pyn*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pist*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignardia* bidwellii (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoft*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici. Septoria* blotch) on wheat or *M, fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); Phy soderma *maydis* (brown spots) on corn; *Phytophthora* spp. (wilt, root, leaf, fruit and stem root) on various plants, such as paprika and cucurbits (e.g. *P. capsicl*), soybeans (e.g. *P. megasperma*, syn. *P. sojae*), potatoes and tomatoes (e.g. *P. infestans*: late blight) and broad leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosa ceous plants, hop, pome and soft fruits, e.g. *P. leucotricha* on apples; *Polymyxa* spp., e.g. on cereals, such as barley, wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); Ramu/aria spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soy beans (e.g. *S. rolfsii* or *S. sclerotiorum*); *Septoria* spp. on various plants, e.g. *S. glycines* (brown spot) on soybeans, *S. tritici* (*Septoria* blotch) on wheat and syn. *Stagonospora nodorum* (*Stagonospora* blotch) on cereals; *Uncinula* (syn. *Erysiphe*) *necator* (powdery mildew, anamorph: Oidium tucken) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: Lepto sphaeria [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incamata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoft*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The present invention is also directed to the use of the fungicidal composition for the treatment of soybean diseases. Most preference is given to the following soybean diseases: *Cercospora kikuchii, Cercospora sojina; Colletotrichum gloeosporoides dematium* var. *truncatum; Corynespora casiicola; Diaporthe phaseolorum; Microsphaera diffusa; Peronospora manshurica; Phakopsora* species, for example *Phakopsora pachyrhizi* and *Phakopsora meibomiae* (soybean rust); *Phytophthora megasperma; Phialophora gregata; Rhizoctonia solani; Sclerotinia sclerotiorum; Septoria* spp. e.g. *Septoria glycines, Thielaviopsis basicola.*

Further, the fungicidal composition of the present invention can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F croobvellense, F culmorum, F graminearum* (*Gibberella zeae*), *F equiseti. F fujikoroi, F musarum, F oxysporum. F proliferatum, F poae, F pseudograminearum, F. sambucinum, F. scirpi, F semitectum, F solani, F sporotrichoides, F langsethiae, F. subglutinans, F. tricinctum, F verticillioides* etc., and also by *Aspergillus* spec., such as *A. jlavus. A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotlys* spec. and others.

The fungicidal composition of the present invention can also be used in the protection of materials, especially for the protection of industrial materials against attack and destruction by phytopathogenic fungi.

The fungicidal composition of the present invention may prevent adverse effects, such as rotting, decay, discoloration, decoloration or formation of mould.

In the case of treatment of wood, the fungicidal composition of the invention may also be used against fungal diseases liable to grow on or inside timber.

The fungicidal composition of the present invention can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber.

Storage goods of animal origin are, for example, hides, leather, furs and hairs. The fungicidal composition of the present invention may prevent adverse effects, such as rotting, decay, discoloration, decoloration or formation of mould.

Microorganisms capable of degrading or altering industrial materials include, for example, bacteria, fungi, yeasts, algae and slime organisms. The fungicidal composition of the present invention preferably acts against fungi, especially moulds, wood-discoloring and wood-destroying fungi (Ascomycetes, Basidiomycetes. Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Nfucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae.*

The fungicidal composition of the present invention can at particular concentrations or application rates, also be used to improve plant properties, or as microbicides, for example as bactericides, viricides (including compositions against viroids) or as compositions against MLO (*Mycoplasma*-like organisms) and RLO (*Rickettsia*-like organisms).

The fungicidal composition of the present invention may intervene in physiological processes of plants and can therefore also be used as plant growth regulators.

Growth regulating effects, comprise earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m2, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising: improved processability relating to size distribution (kernel, fruit, etc.), homogenous riping, grain moisture, better milling, better vinification, better brewing, increased juice yield, harvestability, digestibility, sedimentation value, falling number, pod stability, stability, improved fiber length/strength/uniformity, increase of milk and/or meet quality of silage fed animals, adaption to cooking and frying; improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.; increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.; decreased undesired ingredients such as e.g. less mycotoxines, less aflatoxines, geosmin level, phenolic aromas, lacchase, polyphenol oxidases and peroxidases, nitrate content etc.

The fungicidal composition of the present invention also exhibits a potent strengthening effect in plants. Accordingly, they can be used for mobilizing the defences of the plant against the attack by undesirable microorganisms.

Plant-strengthening (resistance-inducing) substances in the present context are substances capable of stimulating the defence system of plants in such a way that the treated plants, when subsequently inoculated with undesirable microorganisms, develop a high degree of resistance to these microorganisms.

Further, in context of the present invention plant physiology effects comprise the following: Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc; Biotic stress tolerance, comprising increased fungal resistance and increased resistance against nematodes, viruses and bacteria. In context with the present invention, biotic stress tolerance preferably comprises increased fungal resistance and increased resistance against nematodes; Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency. The invention further comprises a method for treating seed. The invention further provides seed which has been treated by one of the methods described in the previous paragraph. The inventive seeds are employed in methods for the protection of seed from unwanted microorganisms. In these methods, seed treated with at least one inventive fungicidal composition is used.

The fungicidal composition of the present invention is also suitable for treating a seed. A large part of the damage to the crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. Therefore, there is a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from the attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

In one embodiment, the present invention provides fungicidal compositions comprising seed in an amount of from 1 g to 1000 g active components per 100 kg of seed.

The present invention also relates to a method for the protection of seed and germinating plants from the attack by phytopathogenic fungi, by treating the seed with an inventive fungicidal composition. The present invention likewise relates to the use of the inventive fungicidal composition for the treatment of seed to protect the seed and the germinating plant from phytopathogenic fungi. The invention further relates to a seed which has been treated with an inventive fungicidal composition for the protection from phytopathogenic fungi.

The control of phytopathogenic fungi which damage plants post-emergence is affected primarily by treating the soil and the above-ground parts of plants with the crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the fungicidal composition not only protect the seed itself, but also the resulting plants after emergence, from phytopathogenic fungi. In this way, the immediate treatment of the crop at the time of sowing or shortly thereafter can be dispensed with.

It is likewise considered to be advantageous that the fungicidal composition can especially also be used with transgenic seed, in which case the plant growing from this seed is capable of expressing a protein which acts against pests. By virtue of the treatment of such seed with the fungicidal compositions, merely the expression of the protein, for example an insecticidal protein, can control certain pests. Surprisingly, a further synergistic effect can be observed in this case, which additionally increases the effectiveness for the protection against attacks by pests.

The fungicidal compositions of the present invention are suitable for protecting seeds of any plant variety which is used in agriculture, in greenhouses, in forests or in horticulture and viticulture. In particular, seeds of cereals (such as wheat, barley, rye, triticale, sorghum/millet and oats), maize, cotton, soyabean, rice, potato, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals. The treatment of seeds of cereals (such as wheat, barley, rye, triticale and oats), maize and rice is of particular significance.

As also described herein, the treatment of transgenic seed with the fungicidal composition of the present invention is of particular significance. This relates to the seed of plants containing at least one heterologous gene which enables the expression of a polypeptide or protein having insecticidal properties.

The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European maize borer and/or the western maize rootworm. The heterologous gene more preferably originates from *Bacillus thuringiensis.*

In one embodiment, the fungicidal composition of the present invention is applied to the seed alone or in a suitable formulation. Preferably, the seed is treated in a state in which it is sufficiently stable for no damage to occur in the course of the treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the novel fungicidal composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 L/ha, especially from 10 to 1000 L/ha.

The fungicidal composition of the present invention may be provided to the end user as ready-for-use formulation, i.e. the compositions can be directly applied to the plants or seeds by a suitable device, such as a spraying or dusting device. Alternatively, the compositions may be provided to the end user in the form of concentrates which have to be diluted, preferably with water, prior to use.

The fungicidal composition of the present invention can be applied directly, i.e. without containing any other components and without having been diluted. In general, it is preferable to apply the composition to the seed in the form of a suitable formulation. Suitable formulations and methods for seed treatment are known to those skilled in the art and are described, for example, in the following documents: U.S. Pat. Nos. 4,272,417, 4,245,432, 4,808,430, 5,876,739, US 2003/0176428 A1, WO 2002/080675, WO 2002/028186.

According to the invention, the expression "composition" stands for the various mixtures or combinations of components (1) and (2), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the components (1) and (2) is not essential for working the present invention.

According to the invention the term "fungicidal composition" means a combination or mixture of at least two active compounds with further agriculturally suitable additives, such as agriculturally suitable auxiliaries, e.g. solvents, carriers, surfactants, extenders or the like which are described above. The term "fungicidal composition" also comprises the terms "crop protection composition", "agrochemical composition" and "formulation".

The fungicidal composition of the present invention comprises a fungicidally effective amount of a compound of formula (I) and component (2) and/or component (3). The term "effective amount" denotes an amount of the composition or of the compound of formula (I), which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound of formula (I) used.

The fungicidal compositions of the present invention include all customary types of fungicidal compositions e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel Formulations for the treatment of plant propagation materials such as seeds (e.g. GF). These and further compositions types are defined in the "Catalogue of pesticide Formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product Formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Examples for Composition Types and their Preparation are i) Water-soluble Concentrates (SL, LS)

10-60 wt % of a compound of formula (I) and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound of formula (I) and 1-10 wt % dispersant (e.g. polyvinyl pyrrolidone) are dissolved in organic solvent (e.g. cyclohexanone) ad 100 wt %. Dilution with water gives a dispersion.

iii) Emulsifiable Concentrates (EC)

15-70 wt % of a compound of formula (I) and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound of formula (I) and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound of formula (I) are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinyl alcohol) is added.

vi) Water-Dispersible Granules and Water-Soluble Granules (WG, SG)

50-80 wt % of a compound of formula (I) are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance. vii) Water-dispersible powders and water-soluble powders (WP, SP, WS) 50-80 wt % of a compound of formula (I) are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound of formula (I) are comminuted with addition of 3-10 wt % dispersants (e.g. sodium lignosulfonate), 1-5 wt % thickener (e.g. carboxymethyl cellulose) and water ad 100 wt % to give a fine suspension of the active substance. Dilution with water gives a stable suspension of the active substance.

ix) Microemulsion (ME)

5-20 wt % of a compound of formula (I) are added to 5-30 wt % organic solvent blend (e.g. fatty acid dimethyl amide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound of formula (I), 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization results in the formation of poly(meth)acrylate microcapsules. Alternatively, an oil phase comprising 5-50 wt % of a compound of formula (I) according to the invention, 0-40 wt % water insoluble organic solvent (e.g. aromatic hydrocarbon), and an isocyanate monomer (e.g. diphenylmethene-4, 4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a compound of formula (I) are ground finely and mixed intimately with solid carrier (e.g. finely divided kaolin) ad 100 wt %.

xii) Granules (GR, FG)

0.5-30 wt % of a compound of formula (I) are ground finely and associated with solid carrier (e.g. silicate) ad 100 wt %. Granulation is achieved by extrusion, spray-drying or fluidized bed.

xiii) Ultra-Low Volume Liquids (UL)

1-50 wt % of a compound of formula (I) are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active ingredient (ai). The active ingredients (ai) are employed in a purity of from 90% to 100%, preferably from 95% to 100% (according to NMR spectrum).

For the purposes of treatment of plant propagation materials, particularly seeds, solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations from 0.01 to 60% by weight, preferably from 0.1 to 40%, in the ready-to-use preparations.

In the novel fungicidal composition according to the invention the component (1) and component (2) are advantageously present in a synergistically effective weight ratio of component (1): component (2) in a range of 100:1 to 1:100, preferably in a weight ratio of 50:1 to 1:50, more preferably in a weight ratio of 20:1 to 1:20, even more preferably in a weight ratio of 10:1 to 1:10.

Further ratios by weight of component (1): component (2) which are preferably used within the weight ratio of 10:1 to 1:10 are 5:1 to 1:5, 4:1 to 1:4, 3:1 to 1:3, 2:1 to 1:2 and 1:1.

When using the fungicidal composition of the present invention as a fungicide, the application rates can be varied within a relatively wide range, depending on the kind of application. The application rate in the case of treatment of plant parts, for example leaves: from 0.1 to 10000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used); in the case of seed treatment: from 2 to 200 g per 100 kg of seed, in the case of soil treatment: from 0.1 to 10000 g/ha, preferably from 1 to 1000 g/ha.

These application rates are merely by way of example and are not limiting for the purposes of the invention.

The user may apply the fungicidal composition of the present invention usually from a predosage device, a knapsack sprayer, a spray tank, a spray plane, or an irrigation system. Usually, the fungicidal composition is made up with water, buffer, and/or further auxiliaries to the desired application concentration and the ready-to-use spray liquor or the fungicidal composition according to the invention is thus obtained. Usually, 20 to 2000 liters, preferably 50 to 400 liters, of the ready-to-use spray liquor are applied per hectare of agricultural useful area.

The compounds of the invention can be used in combination with models e.g. embedded in computer programs for site specific crop management, satellite farming, precision farming or precision agriculture.

Such models support the site specific management of agricultural sites with data from various sources such as soils, weather, crops (e.g. type, growth stage, plant health), weeds (e.g. type, growth stage), diseases, pests, nutrients, water, moisture, biomass, satellite data, yield etc. with the purpose to optimize profitability, sustainability and protection of the environment. In particular, such models can help to optimize agronomical decisions, control the precision of pesticide applications and record the work performed.

As an example, the compounds of the invention can be applied to a crop plant according to an appropriate dose regime if a model models the development of a pest and calculates that a threshold has been reached for which it is recommendable to apply the compound of the invention to the crop plant.

Commercially available systems which include agronomic models are e.g. FieldScripts™ from The Climate Corporation, Xarvio™ from BASF, AGLogic™ from John Deere, etc.

The compounds of the invention can also be used in combination with smart spraying equipment such as e.g. spot spraying or precision spraying equipment attached to or housed within a farm vehicle such as a tractor, robot, helicopter, airplane, unmanned aerial vehicle (UAV) such as a drone, etc. Such an equipment usually includes input sensors (such as e.g. a camera) and a processing unit configured to analyze the input data and configured to provide a decision based on the analysis of the input data to apply the compound of the invention to the crop plants (respectively the weeds) in a specific and precise manner. The use of such smart spraying equipment usually also requires positions systems (e.g. GPS receivers) to localize recorded data and to guide or to control farm vehicles; geographic information systems (GIS) to represent the information on intelligible maps, and appropriate farm vehicles to perform the required farm action such as the spraying.

In an example, pests can be detected from imagery acquired by a camera. In an example the pests can be identified and/or classified based on that imagery. Such identification and/classification can make use of image processing algorithms. Such image processing algorithms can utilize machine learning algorithms, such as trained neutral networks, decision trees and utilize artificial intelligence algorithms. In this manner, the compounds described herein can be applied only where needed.

In one embodiment of the present invention is a kit for preparing a usable fungicidal composition, the kit comprising a) a composition comprising component (1) as defined herein and at least one auxiliary; and b) a composition comprising component (2) as defined herein and at least one auxiliary; and optionally c) a composition comprising at least one auxiliary and optionally a further active component (3) as defined herein.

The individual components of the fungicidal composition of the present invention such as parts of a kit or parts of a binary or ternary mixture may be mixed by the user himself in a spray tank or any other kind of vessel used for applications (e.g. seed treater drums, seed pelleting machinery, knapsack sprayer) and further auxiliaries may be added, if appropriate.

The present invention furthermore relates to fungicidal compositions comprising a mixture of at least one compound of formula (I) (component 1) and at least one further active compound useful for plant protection, e.g. selected from the groups A) to L) (component 2) as described above, and if desired one suitable solvent or solid carrier. These mixtures are of particular interest, since many of them at the same application rate show higher efficiencies against harmful fungi.

Furthermore, combating harmful fungi with a mixture of a compound of formula (I) and at least one active compound from groups A) to L), as described above, is more efficient than combating those fungi with the individual compounds of formula (I) or individual active compound from groups A) to L). By applying a compound of formula (I) together with at least one active compound from groups A) to L), a synergistic effect can be obtained, i.e. more than simple addition of the individual effects is obtained (synergistic mixtures).

However, besides the actual synergistic action with respect to fungicidal activity, the composition of the present invention may also have further surprising advantageous properties. Examples of such advantageous properties that may be mentioned are: more advantageous degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

The synergistic effect can be obtained by applying the compound of formula (I) and at least one further active compound simultaneously, either jointly (e.g. as tank-mix) or separately, or in succession, wherein the time interval between the individual applications is selected to ensure that the active compound applied first still occurs at the site of action in a sufficient amount at the time of application of the further active substance(s). The order of application is not essential for the working of the present invention.

When sequentially applying a compound of formula (I) and at least one further active compound, the time between both applications may vary e.g. between 2 hours to 7 days. Also, a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the compound of formula (I) [component (1)] and the component (2) generally depends from the properties of the active components used, usually it is in the range of 1:10000 to 10000:1, often it is in the range of 1:100 to 100:1, regularly in the range of 1:50 to 50:1, preferably in the range of 1:20 to 20:1, more preferably in the range of 1:5 to 5:1 and in particular in the range of 1:2 to 2:1.

According to a further embodiment of the binary mixtures and compositions, the weight ratio of the compound of formula (I) [component (1)] and the component (2) usually is in the range of 1000:1 to 1:1, often in the range of 100:1 to 1:1, regularly in the range of 50:1 to 1:1, preferably in the range of 20:1 to 1:1, more preferably in the range of 5:1 to 1:1 and in particular in the range of 2:1 to 1:1.

According to a further embodiment of the binary mixtures and compositions, the weight ratio of the compound of formula (I) [component (1)] and the component (2) usually is in the range of 1:1 to 1:1000, often in the range of 1:1 to 1:100, regularly in the range of 1:1 to 1:50, preferably in the range of 1:1 to 1:20, more preferably in the range of 1:1 to 1:5 and in particular in the range of 1:1 to 1:2.

In the ternary mixtures, i.e. compositions according to the invention comprising the compound of formula (I) [component (1)] and component (2) and a compound of formula (III) [component (3)], the weight ratio of compound of formula (I) [component (1)] and component (2) is in the range of 1:100 to 100:1, regularly in the range of 1:50 to 50:1, preferably in the range of 1:20 to 20:1, more preferably in the range of 1:5 to 5:1 and in particular in the range of 1:2 to 2:1, and the weight ratio of component (1) and component (3) is in the range of 1:100 to 100:1, regularly in the range of 1:50 to 50:1, preferably in the range of 1:20 to 20:1, more preferably in the range of 1:5 to 5:1 and in particular in the range of 1:2 to 2:1.

Any further active components are, if desired added in a ratio of 20:1 to 1:20 to the compound of formula (I) [component (1)].

These ratios are also suitable for seed treatment.

The method of treatment according to the invention also provides the use or application of component (1) and component (2) in a simultaneous, separate or sequential manner. If the single active ingredient is applied in a sequential manner, i.e. at different times, they are applied one after the other within a reasonable period, such as a few hours or days. Preferably the order of applying the component (1) and component (2) is not essential for working the present invention.

In the fungicidal composition of the present invention the component (1) and (2) are advantageously present in a synergistically effective weight ratio of (1):(2) in a range of 100:1 to 1:100, preferably in a weight ratio of 50:1 to 1:50, more preferably in a weight ratio of 20:1 to 1:20, even more preferably in a weight ratio of 10:1 to 1:10, 5:1 to 1:5 and 2:1 to 1:2.

The fungicidal composition comprising the compound of formula (I) [component (1)] and the component (2) may show a synergistic effect. This occurs whenever the efficacy of an active ingredient combination is greater than the sum of the efficacies of the individual components. The activity to be expected E for a given active ingredient combination obeys the so-called COLBY formula.

An efficacy of 0 means that the infection level of the treated plants corresponds to that of the untreated control plants; an efficacy of 100 means that the treated plants were not infected.

The expected efficacies of active compound combinations may be determined using Colby's formulas (COLBY, S. R. "Calculating synergistic and antagonistic responses of herbicide combination", Weeds, Vol. 15, pages 20-22; 1967).

Colby's Formulas:

The expected activity for a given combination of two active compounds (binary composition) can be calculated as follows:

$$E = X + Y - \frac{XY}{100}$$

In which E represents the expected percentage of inhibition of the disease for the combination of two fungicides at defined doses (for example equal to x and y respectively), x is the percentage of inhibition observed for the disease by the compound (1) at a given dose (equal to x), y is the percentage of inhibition observed for the disease by the compound (2) at a defined dose (equal to y). When the percentage of inhibition observed for the combination is greater than E, there is a synergistic effect.

The expected activity for a given combination of three active compounds (ternary composition) can be calculated as follows:

$$E = X + Y + Z - \frac{XY + XZ + YZ}{100} + \frac{XYZ}{10000}$$

X: efficacy, expressed in % of the untreated control, when using the active compound (1) at the concentration a, Y: efficacy, expressed in % of the untreated control, when using the active compound (2) at the concentration b Z: efficacy, expressed in % of the untreated control, when using the active compound (3) at the concentration c.

E is the efficacy when the active compounds (1), (2) and (3) are applied at application rates of a, b and c.

CHEMISTRY EXAMPLES

The following representative examples set forth the manner and process of making compounds of the present invention without being a limitation thereof and include the best mode contemplated by the inventors for carrying out the invention.

Chemistry Examples

Example 1: Preparation of 2-(3-fluorophenoxy)-1-(4-(5-(trifluoromethyl)-1,2,4-oxadiazol-3-yl)phenyl) ethan-1-one (Compound no. I-1)

a) Step-1:4-(2-methyl-1,3-dioxolan-2-yl)benzonitrile

To a stirred solution of 4-acetylbenzonitrile (10 g, 69 mmol) and ethylene glycol (80 mL, 1.4 mmol), trimethyl orthoformate (50 mL, 0.9 mmol) and N-bromosuccinimide (1.2 g, 7 mmol) were added at 25° C. The resulting reaction mixture was stirred at 65° C., for 12 h. After completion of the reaction, the reaction mixture was diluted with dichloromethane (120 mL) and washed with water (80 mL). The dichloromethane layer was dried over anhydrous sodium sulphate and concentrated under reduced pressure to obtain 4-(2-methyl-1,3-dioxolan-2-yl)benzonitrile (12 g, 92% yield).

b) Step-2: N'-hydroxy-4-(2-methyl-1,3-dioxolan-2-yl)benzimidamide

To a stirred solution of 4-(2-methyl-1,3-dioxolan-2-yl) benzonitrile (12 g, 63 mmol) and ethanol (80 mL), sodium bicarbonate (9.6 g, 114 mmol) and hydroxylamine hydrochloride (5.3 g. 76 mmol) were added at 0° C. The resulting reaction mixture was stirred at 65° C., for 4 h. After completion of the reaction, the reaction mixture was filtered and concentrated under reduced pressure to obtain N'-hydroxy-4-(2-methyl-1,3-dioxolan-2-yl)benzimidamide (12 g, 85% yield).

c) Step-3:3-(4-(2-methyl-1,3-dioxolan-2-yl)phenyl)-5-(trifluoromethyl)-1,2,4-oxadiazole To a stirred solution of N'-hydroxy-4-(2-methyl-1,3-dioxolan-2-yl)benzimidamide (0.3 g. 1.4 mmol) and tetrahydrofuran (30 mL), trifluoroacetic anhydride (0.25 mL, 1.8 mmol) was added at 0° C. The resulting reaction mixture was stirred at 25° ° C., for 16 h. The reaction mixture was diluted with ethyl acetate (40 mL) and washed with a sodium bicarbonate solution (2×40 mL). The ethyl acetate layer was dried over anhydrous sodium sulphate and concentrated under reduced pressure to obtain a crude product. The obtained crude product was purified by column chromatography to obtain 3-(4-(2-methyl-1,3-dioxolan-2-yl)phenyl)-5-(trifluoromethyl)-1,2,4-oxadiazole (0.2 g, 49% yield).

d) Step-4:1-(4-(5-(trifluoromethyl)-1,2,4-oxadiazol-3-yl)phenyl)ethan-1-one To a stirred solution of 3-(4-(2-methyl-1,3-dioxolan-2-yl) phenyl)-5-(trifluoromethyl)-1,2,4-oxadiazole (10 g, 33 mmol) and acetone (50 mL), iodine (0.5 g, 2 mmol) was added. The resulting reaction mixture was stirred at 25° C., for 3 h. After completion of the reaction, the reaction mixture was concentrated under reduced pressure, diluted with ethyl acetate (80 mL) and washed with water (40 mL). The ethyl acetate layer was dried over anhydrous sodium sulphate and concentrated under reduced pressure to obtain a crude residue. The obtained crude residue was purified by column chromatography to obtain 1-(4-(5-(trifluoromethyl)-1,2,4-oxadiazol-3-yl)phenyl)ethan-1-one (6 g, 70% yield).

e) Step-5:2-bromo-1-(4-(5-(trifluoromethyl)-1,2,4-oxadiazol-3-yl)phenyl)ethan-1-one To a stirred solution of 1-(4-(5-(trifluoromethyl)-1,2,4-oxadiazol-3-yl)phenyl)ethan-1-one (16 g, 63 mmol) and dichloromethane (100 mL), bromine (2.3 mL, 43 mmol) was added at 0° C. The resulting reaction mixture was stirred for 3 h at 25° C. After completion of the reaction, the reaction mixture was diluted with dichloromethane (120 mL) and washed with water (80 mL). The dichloromethane layer was dried over anhydrous sodium sulphate and concentrated under reduced pressure to obtain a crude residue. The obtained crude residue was purified by column chromatography to obtain 2-bromo-1-(4-(5-(trifluoromethyl)-1,2,4-oxadiazol-3-yl)phenyl)ethan-1-one (11 g, 53% yield).

f) Step-6:2-(3-fluorophenoxy)-1-(4-(5-(trifluoromethyl)-1,2,4-oxadiazol-3-yl)phenyl)ethan-1-one (Compound no. I-1)

To a stirred solution of 2-bromo-1-(4-(5-(trifluoromethyl)-1,2,4-oxadiazol-3-yl)phenyl)ethan-1-one (0.2 g, 0.7 mmol) and acetonitrile (8 mL), potassium carbonate (0.2 g, 1.6 mmol)) and 3-fluorophenol (0.17 g, 1.49 mmol) were added at 0° C. under nitrogen atmosphere. The resulting reaction mixture was warmed to 25° C., for 1 h. After completion of the reaction, the reaction mixture was diluted with ethyl acetate (10 mL) and washed with water (10 mL). The ethyl acetate layer was dried over anhydrous sodium sulphate and concentrated under reduced pressure to obtain a crude residue. The obtained crude residue was purified by column chromatography to obtain 2-(3-fluorophenoxy)-1-(4-(5-(trifluoromethyl)-1,2,4-oxadiazol-3-yl)phenyl)ethan-1-one (0.111 g, 41% yield). 1H-NMR (400 MHz, DMSO-d6) δ 8.26-8.21 (m, 4H), 7.31 (td, 1H), 6.94 (dt, 1H), 6.87-6.84 (m, 1H), 6.80-6.75 (m, 1H), 5.68 (s, 2H); LCMS (M−H): 364.9.

The following compounds in Table 1 were prepared by using the analogous procedure as described in example 1.

TABLE 1

| Compd no. | IUPAC name | Analytical data |
|---|---|---|
| I-2 | 2-(4-fluorophenoxy)-1-(4-(5-(trifluoromethyl)-1,2,4-oxadiazol-3-yl)phenyl)ethan-1-one | $^1$H-NMR (400 MHz, DMSO-d6) δ 8.25-8.21 (m, 4H), 7.14-7.08 (m, 2H), 7.04-7.00 (m, 2H), 5.62 (s, 2H); LCMS (M − H): 364.9 |
| I-3 | 2-((6-fluoropyridin-3-yl)oxy)-1-(4-(5-(trifluoromethyl)-1,2,4-oxadiazol-3-yl)phenyl)ethan-1-one | $^1$H-NMR (400 MHz, DMSO-d6) δ 8.26-8.20 (m, 4H), 7.99 (dd, 1H), 7.71-7.66 (m, 1H), 7.14-7.11 (m, 1H), 5.76 (s, 2H); LCMS(M + 1): 367.70 |

Example 2: Preparation of 2-(thiazol-2-ylsulfonyl)-1-(4-(5-(trifluoromethyl)-1,2,4-oxadiazol-3-yl)phenyl)ethan-1-one (Compound no. I-4)

a) Step 1: 2-(thiazol-2-ylthio)-1-(4-(5-(trifluoromethyl)-1,2,4-oxadiazol-3-yl)phenyl)ethan-1-one To a stirred solution of thiazole-2-thiol (0.3 g, 2.5 mmol) in acetonitrile (10 mL), potassium carbonate (0.7 g, 5.1 mmol) was added at 25° C. and stirred for 15 min at the same temperature. To this reaction mixture, 2-bromo-1-(4-(5-(trifluoromethyl)-1,2,4-oxadiazol-3-yl)phenyl)ethan-1-one (0.8 g, 2.5 mmol) was added and the resulting reaction mixture was stirred at 25° C., for 3 h. The reaction mixture was quenched with water (25 mL) and extracted with ethyl acetate (3×50 mL). The combined organic layer was dried over anhydrous sodium sulfate and evaporated to dryness under reduced pressure to obtain a crude residue. The obtained crude residue was purified by preparative HPLC to obtain 2-(thiazol-2-ylthio)-1-(4-(5-(trifluoromethyl)-1,2,4-oxadiazol-3-yl)phenyl)ethan-1-one (0.3 g, 31% yield).

b) Step 2: 2-(thiazol-2-ylsulfonyl)-1-(4-(5-(trifluoromethyl)-1,2,4-oxadiazol-3-yl)phenyl)ethan-1-one (Compound no. I-4)

To a stirred solution of 2-(thiazol-2-ylthio)-1-(4-(5-(trifluoromethyl)-1,2,4-oxadiazol-3-yl)phenyl)ethan-1-one (0.12 g, 0.3 mmol) in methanol (8 mL) and water (2 mL), potassium peroxymonosulfate (oxone) (0.4 g, 0.6 mmol) was added at 25° C. The resulting reaction mixture was heated at 60° C., for 2 h. The reaction was cooled to 0° C. and water (100 mL) was added into it. The product was extracted with ethyl acetate (3×50 mL). The combined ethyl acetate layer was washed with brine solution (2×50 mL), dried over anhydrous sodium sulfate and concentrated under reduced pressure to obtain a crude product. The obtained crude product was triturated with hexane to obtain 2-(thiazol-2-ylsulfonyl)-1-(4-(5-(trifluoromethyl)-1,2,4-oxadiazol-3-yl)phenyl)ethan-1-one (0.078 g, 60% yield). $^1$H-NMR (400 MHZ, DMSO-d6) δ 8.30 (d, 1H), 8.14-8.22 (m, 5H), 5.70 (d, 2H); LCMS (M-1): 401.70.

Example 3: Preparation of 2-((3-fluorophenyl)amino)-1-(4-(5-(trifluoromethyl)-1,2,4-oxadiazol-3-yl)phenyl)ethan-1-one (Compound no. I-5)

To a stirred solution of 2-bromo-1-(4-(5-(trifluoromethyl)-1,2,4-oxadiazol-3-yl)phenyl)ethan-1-one (0.5 g. 1.5 mmol) in ethanol (10 mL), 3-fluoroaniline (0.16 mL, 1.6 mmol) and sodium bicarbonate (0.15 g, 1.8 mmol) were added. The resulting reaction mixture was stirred at 25° C., for 12 h. After completion of the reaction, the reaction mixture was filtered and the obtained solid was washed with n-hexane (10 mL) to obtain 2-((3-fluorophenyl)amino)-1-(4-(5-(trifluoromethyl)-1,2,4-oxadiazol-3-yl)phenyl)ethan-1-one (0.4 g, 73% yield). 1H-NMR (400 MHZ, DMSO-d6) δ 8.28 (dd, 2H), 8.23 (dd, 2H), 7.04-7.10 (m, 1H), 6.50-6.56 (m, 2H), 6.30-6.34 (m, 1H), 6.26 (t, 1H), 4.77 (d, 2H); LCMS (M+H): 366.

The following compounds in Table 2 were prepared by using the analogous procedure as described in example 3.

TABLE 2

| Compd no | IUPAC name | Analytical data |
|---|---|---|
| I-8 | 2-((4-fluorophenyl)amino)-1-(4-(5-(trifluoromethyl)-1,2,4-oxadiazol-3-yl)phenyl)ethan-1-one | $^1$H-NMR (400 MHz, DMSO-d6) δ 8.28-8.21 (m, 4H), 6.89-6.95 (m, 2H), 6.67-6.72 (m, 2H), 5.86 (t, 1H), 4.72 (d, 2H); LCMS (M − H): 363.75 |

Example 4: Preparation of 2-(benzylthio)-1-(5-(5-(trifluoromethyl)-1,2,4-oxadiazol-3-yl)pyridin-2-yl) ethan-1-one (Compound no. I-6)

a) Step-1:6-(1-ethoxyvinyl)nicotinonitrile

To a stirred solution of 6-chloronicotinonitrile (15 g, 108 mmol) in toluene (120 mL), (1-ethoxyvinyl)tributylstannane (40 mL, 119 mmol) and bis(triphenylphosphine)palladium (II)dichloride (3.8 g. 5.4 mmol) were added at 25° C. The resulting reaction mixture was degassed with nitrogen for 15 min, and then the reaction mixture was heated at 80° C., for 16 h. The reaction mixture was filtered through a celite bed and the filtrate was concentrated under reduced pressure to obtain a crude product. The obtained crude product was purified by column chromatography to obtain 6-(1-ethoxyvinyl)nicotinonitrile (16 g, 87% yield).

b) Step-2:6-(1-ethoxyvinyl)-N'-hydroxynicotinimidamide

To a stirred solution of 6-(1-ethoxyvinyl)nicotinonitrile (16 g, 95 mmol) in ethanol (120 mL), hydroxylamine (7 mL, 114 mmol) was added at 25° C. The resulting reaction mixture was stirred at 25° C. for 12 h. The reaction mixture was concentrated under reduced pressure to obtain 6-(1-ethoxyvinyl)-N'-hydroxynicotinimidamide (19 g, 98% yield).

c) Step-3:3-(6-(1-ethoxyvinyl)pyridin-3-yl)-5-(trifluoromethyl)-1,2,4-oxadiazole To a stirred solution of 6-(1-ethoxyvinyl)-N'-hydroxynicotinimidamide (18 g, 87 mmol) in tetrahydrofuran (160 mL), triethylamine (15 mL, 104 mmol) was slowly added at 0° C., followed by dropwise addition of trifluoroacetic anhydride (15 mL, 104 mmol) at 0° C. The resulting reaction mixture was stirred at 25° C., for 12 h. After completion of the reaction, the reaction mixture was diluted with ethyl acetate (200 mL) and washed with saturated sodium bicarbonate solution (2×200 mL). The combined organic layer was separated, dried over anhydrous sodium sulphate, concentrated under reduced pressure to obtain a crude product. The obtained crude product was purified by column chromatography to obtain 3-(6-(1-ethoxyvinyl)pyridin-3-yl)-5-(trifluoromethyl)-1,2,4-oxadiazole (11 g, 40 mmol, 46% yield).

d) Step-4:2-bromo-1-(5-(5-(trifluoromethyl)-1,2,4-oxadiazol-3-yl)pyridin-2-yl)ethan-1-one To a stirred solution of 3-(6-(1-ethoxyvinyl)pyridin-3-yl)-5-(trifluoromethyl)-1,2,4-oxadiazole (11 g, 38.6 mmol) in tetrahydrofuran (100 mL), water (4 mL), N-bromosuccinimide (5.8 g. 33 mmol) were slowly added at 0° C. The resulting reaction mixture was stirred at 25° C., for 2 h. After completion of the reaction, the reaction mixture was diluted with ethyl acetate (200 mL) and washed with water (200 mL). The organic layer was separated, dried over anhydrous sodium sulphate and concentrated under reduced pressure to obtain a crude product. The obtained crude product was purified by column chromatography to obtain 2-bromo-1-(5-(5-(trifluoromethyl)-1,2,4-oxadiazol-3-yl)pyridin-2-yl) ethan-1-one (8 g, 63% yield).

e) Step-6:2-(benzylthio)-1-(5-(5-(trifluoromethyl)-1,2,4-oxadiazol-3-yl)pyridin-2-yl)ethan-1-one (Compound no. I-6)

To a stirred solution of benzyl mercaptan (0.25 mL, 2.1 mmol) in acetonitrile (8 mL), potassium carbonate (0.3 g. 2.1 mmol) was added at 25° ° C., for 15 min followed by the addition of 2-bromo-1-(5-(5-(trifluoromethyl)-1,2,4-oxadiazol-3-yl)pyridin-2-yl)ethan-1-one (0.6 g, 1.8 mmol) at 0° C. The resulting reaction mixture was stirred at 25° C., for 4 h. After completion of the reaction, the reaction mixture was diluted with ethyl acetate (20 mL), washed with water (2×20 mL), dried over anhydrous sodium sulphate and concentrated under reduced pressure to obtain a crude product. The obtained crude product was purified by preparative HPLC to obtain 2-(benzylthio)-1-(5-(5-(trifluoromethyl)-1,2,4-oxadiazol-3-yl)pyridin-2-yl)ethan-1-one (300 mg, 44% yield) 1H-NMR (400 MHZ, DMSO-d6) δ 9.33 (q, 1H), 8.65 (dd, 1H), 8.22 (dd, 1H), 7.35-7.22 (m, 5H), 3.99 (s, 2H), 3.76 (s, 2H); LCMS (M+1): 379.95.

Example 5: Preparation of 2-((3-fluorophenyl)sulfinyl)-1-(5-(5-(trifluoromethyl)-1,2,4-oxadiazol-3-yl) pyridin-2-yl)ethan-1-one (Compound no I-7)

a) Step 1: 2-((3-fluorophenyl)thio)-1-(5-(5-(trifluoromethyl)-1,2,4-oxadiazol-3-yl)pyridin-2-yl)ethan-1-one To a stirred solution of 3-fluorobenzenethiol (0.06 mL, 0.71 mmol) in acetonitrile (8 mL), potassium carbonate (0.1 g, 0.7 mmol) was added at 25° C., followed by the addition of 2-bromo-1-(5-(5-(trifluoromethyl)-1,2,4-oxadiazol-3-yl) pyridin-2-yl)ethan-1-one (0.2 g, 0.6 mmol) at 25° C.. The reaction was stirred at 25° C., for 4 h. After completion of the reaction, the reaction mixture was diluted with dichloromethane (20 mL) and washed with water (2×20 mL), dried over anhydrous sodium sulphate and concentrated under reduced pressure to obtain a crude product. The obtained crude product was purified by preparative HPLC to obtain 2-((3-fluorophenyl)thio)-1-(5-(5-(trifluoromethyl)-1,2,4-oxadiazol-3-yl)pyridin-2-yl)ethan-1-one (65 mg, 28% yield).

b) Step 2: 2-((3-fluorophenyl)sulfinyl)-1-(5-(5-(trifluoromethyl)-1,2,4-oxadiazol-3-yl)pyridin-2-yl) ethan-1-one (compound no. I-7)

To a stirred solution of 2-((3-fluorophenyl)thio)-1-(5-(5-(trifluoromethyl)-1,2,4-oxadiazol-3-yl)pyridin-2-yl)ethan-1-one (0.2 g, 0.5 mmol) in methanol (8 mL) and water (2 mL), potassium peroxymonosulfate (oxone) (0.26 g, 0.4 mmol) was added at 0° C. The resulting reaction mixture was further stirred at 25° C. for 30 min. After completion of the reaction, the reaction mixture was quenched with water (20 mL) and extracted with ethyl acetate (3×15 mL). The combined organic layer was washed with brine solution (2×25 mL), dried over anhydrous sodium sulphate and concentrated under reduced pressure to obtain a crude product. The obtained crude product was purified by preparative HPLC to obtain 2-((3-fluorophenyl)sulfinyl)-1-(5-(5-(trifluoromethyl)-1,2,4-oxadiazol-3-yl)pyridin-2-yl)ethan-1-one (69 mg, 0.173 mmol, 33% yield). 1H-NMR (400 MHZ, DMSO-d6) δ 9.29 (q, 1H), 8.64 (dd, 1H), 8.18 (dd, 1H), 7.65-7.55 (m, 3H), 7.40-7.35 (m, 1H), 4.90 (dd, 2H); LCMS (M+1): 399.70.

BIOLOGY EXAMPLES

As described herein, the compounds of formula (I) show fungicidal activities which are exerted with respect to numerous fungi which attack on important agricultural crops. The compounds of the present invention were assessed for their activity as described in the following tests:

Biological Test Examples

The compounds were further selected for testing under glasshouse conditions. The methods followed to check the efficacy of compounds against different pathogens were as following:

Example A: *Pyricularia Oryzae* Test (Rice Plants)

The single compounds or the respective compound combinations were dissolved in 2% dimethyl sulfoxide/acetone and then mixed with water containing emulsifier to a calibrated spray volume of 30 mL. The test solutions were poured into spray bottles for further applications.

To test the preventive activity of the single compounds and their combinations, healthy young rice plants, raised in the greenhouse, were sprayed with the active compound preparation at the stated application rates inside the spray cabinets using hollow cone nozzles. One day after treatment, the plants were inoculated with a spore suspension containing $1.4\times10^6$ *Pyricularia oryzae* inoculum. The inoculated plants were then kept in a greenhouse chamber at 24° C. temperature and 95% relative humidity for disease expression.

A visual assessment of the performance of the compounds or compound combinations was carried out by rating the disease severity (0-100% scale) on treated plants 3, 7, 10 and 15 days after application. Efficacy (% control) of the single compounds and combinations were calculated by comparing the disease rating in the treatment with the one of the untreated control. The compounds were also assessed for their plant compatibility by recording symptoms like necrosis, chlorosis and stunting.

The results are shown for the representive compound of formula (I), particularly (I-2), (I-3) and (I-8) in Table A1-A3 respectively.

Surprisingly, the following combinations, indicated in the table below, have revealed unexpected synergistic effects:

TABLE A1

Table-A1: The synergistic fungicidal activity of the compositions of the present invention, wherein the representative compound of formula (I) is particularly compound (I-2) as component (1) and other components (2) selected from the groups (A) to (L) against *Pyricularia oryzae* in rice are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-2) | 1 | | 17 | | |
| 2 | Compound (I-2) | 10 | | 37 | | |
| 3 | Mefentrifluconazole | 0.1 | | 24 | | |
| 4 | Pyraclostrobin | 0.1 | | 24 | | |
| 5 | Compound (I-2) + Mefentrifluconazole | (1:0.1) | 10:1 | 47 | 37 | 11 |
| 6 | Compound (I-2) + Mefentrifluconazole | (10:0.1) | 100:1 | 63 | 52 | 11 |
| 7 | Compound (I-2) + Pyraclostrobin | (10:0.1) | 100:1 | 66 | 52 | 14 |

TABLE A2

Table-A2: The synergistic fungicidal activity of the compositions of the present invention, wherein the representative compound of formula (I) is particularly compound (I-3) as component (1) and other components (2) selected from the groups (A) to (L) against *Pyricularia oryzae* in rice are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 10 | | 42 | | |
| 2 | Fluindapyr | 0.05 | | 11 | | |
| 3 | Compound (I-3) + Fluindapyr | (10:0.05) | 200:1 | 64 | 49 | 15 |

TABLE A3

Table-A3: The synergistic fungicidal activity of the compositions of the present invention, wherein the representative compound of formula (I) is particularly compound (I-8) as component (1) and other components (2) selected from the groups (A) to (L) against *Pyricularia oryzae* in rice are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-8) | 1 | | 17 | | |
| 2 | Compound (I-8) | 5 | | 22 | | |
| 3 | Compound (I-8) | 10 | | 31 | | |
| 4 | Prothioconazole | 0.05 | | 17 | | |
| 5 | Pyraclostrobin | 0.05 | | 16 | | |
| 6 | Trifloxystrobin | 0.1 | | 32 | | |
| 7 | Boscalid | 0.1 | | 37 | | |
| 8 | Difenoconazole | 0.1 | | 26 | | |
| 9 | Azoxystrobin | 0.1 | | 26 | | |
| 10 | Metominostrobin | 0.1 | | 33 | | |
| 11 | Metiram | 0.1 | | 18 | | |
| 12 | Compound (I-8) + Prothioconazole | (5:0.05) | 100:1 | 47 | 35 | 12 |
| 13 | Compound (I-8) + Pyraclostrobin | (1:0.05) | 20:1 | 44 | 30 | 14 |
| 14 | Compound (I-8) + Pyraclostrobin | (5:0.05) | 100:1 | 56 | 35 | 21 |
| 15 | Compound (I-8) + Trifloxystrobin | (10:0.1) | 100:1 | 64 | 53 | 11 |
| 16 | Compound (I-8) + Boscalid | (5:0.1) | 50:1 | 64 | 51 | 13 |
| 17 | Compound (I-8) + Boscalid | (10:0.1) | 100:1 | 67 | 56 | 10 |
| 18 | Compound (I-8) + Difenoconazole | (1:0.1) | 10:1 | 50 | 38 | 12 |
| 19 | Compound (I-8) + Difenoconazole | (5:0.1) | 50:1 | 53 | 42 | 10 |
| 20 | Compound (I-8) + Difenoconazole | (10:0.1) | 100:1 | 64 | 49 | 15 |
| 21 | Compound (I-8) + Azoxystrobin | (5:0.1) | 50:1 | 56 | 42 | 13 |
| 22 | Compound (I-8) + Azoxystrobin | (10:0.1) | 100:1 | 61 | 49 | 13 |
| 23 | Compound (I-8) + Metominostrobin | (5:0.1) | 50:1 | 61 | 48 | 13 |
| 24 | Compound (I-8) + Metominostrobin | (10:0.1) | 100:1 | 67 | 53 | 13 |
| 25 | Compound (I-8) + Metiram | (1:0.1) | 10:1 | 50 | 32 | 18 |
| 26 | Compound (I-8) + Metiram | (5:0.1) | 50:1 | 64 | 36 | 28 |
| 27 | Compound (I-8) + Metiram | (10:0.1) | 100:1 | 69 | 43 | 26 |

Example B: *Alternaria solani* Test (Tomato Plants)

The single compounds or respective compound combinations were dissolved in 2% dimethyl sulfoxide/acetone and then mixed with water containing emulsifier to a calibrated spray volume of 30 mL. The test solutions were poured into spray bottles for further applications.

To test the preventive activity of the single compounds and their combinations, healthy young tomato plants, raised in the greenhouse, were sprayed with the active compound preparation at the stated application rates inside the spray cabinets using hollow cone nozzles. One day after treatment, the plants were inoculated with a spore suspension containing $0.24\times10^6$ *Alternaria solani* inoculum and 2% Malt. The inoculated plants were then kept in a greenhouse chamber at 22-24° C. temperature and 90-95% relative humidity for disease expression.

A visual assessment of the performance of the compounds or compound combinations was carried out by rating the disease severity (0-100% scale) on treated plants 3, 7, 10 and 15 days after application. Efficacy (% control) of the single compounds and combinations was calculated by comparing the disease rating in the treatment with the one of the untreated control. The compounds were also assessed for their plant compatibility by recording symptoms like necrosis, chlorosis and stunting.

The results are shown for the representative compounds of compound of formula (I) particularly, (I-2), (I-3) and (I-8) in Table B1-B3 respectively.

Surprisingly, the following combinations, indicated in the table below, have revealed unexpected synergistic effects:

TABLE B1

Table-B1: The synergistic fungicidal activity of the compositions of the present invention, wherein the representative compound of formula (I) is particularly compound (I-2) as component (1) and other components (2) selected from the groups (A) to (L) against *Alternaria solani* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-2) | 1 | | 34 | | |
| 2 | Compound (I-2) | 5 | | 42 | | |
| 3 | Compound (I-2) | 10 | | 47 | | |
| 4 | Mefentrifluconazole | 0.05 | | 12 | | |
| 5 | Mefentrifluconazole | 0.1 | | 26 | | |
| 6 | Prothioconazole | 0.05 | | 20 | | |
| 7 | Prothioconazole | 0.1 | | 31 | | |
| 8 | Trifloxystrobin | 0.1 | | 40 | | |
| 9 | Boscalid | 0.05 | | 13 | | |
| 10 | Boscalid | 0.1 | | 26 | | |
| 11 | Fluxapyroxad | 0.05 | | 40 | | |
| 12 | Azoxystrobin | 0.05 | | 33 | | |
| 13 | Azoxystrobin | 0.1 | | 49 | | |
| 14 | Folpet | 0.05 | | 12 | | |
| 15 | Folpet | 0.1 | | 16 | | |
| 16 | Mancozeb | 0.1 | | 16 | | |
| 17 | Benzovindiflupyr | 0.05 | | 14 | | |
| 18 | Benzovindiflupyr | 0.1 | | 29 | | |
| 19 | Fluindapyr | 0.05 | | 14 | | |
| 20 | Inpyrfluxam | 0.05 | | 14 | | |
| 21 | Inpyrfluxam | 0.1 | | 23 | | |
| 22 | Dithianon | 0.05 | | 21 | | |
| 23 | Dithianon | 0.1 | | 26 | | |
| 24 | Compound (I-2) + Mefentrifluconazole | (1:0.05) | 20:1 | 61 | 42 | 19 |
| 25 | Compound (I-2) + Mefentrifluconazole | (10:0.05) | 200:1 | 78 | 53 | 24 |
| 26 | Compound (I-2) + Mefentrifluconazole | (1:0.1) | 10:1 | 67 | 51 | 16 |
| 27 | Compound (I-2) + Mefentrifluconazole | (5:0.1) | 50:1 | 78 | 57 | 21 |
| 28 | Compound (I-2) + Mefentrifluconazole | (10:0.1) | 100:1 | 81 | 61 | 20 |
| 29 | Compound (I-2) + Prothioconazole | (1:0.05) | 20:1 | 61 | 47 | 14 |
| 30 | Compound (I-2) + Prothioconazole | (10:0.05) | 200:1 | 78 | 58 | 20 |
| 31 | Compound (I-2) + Prothioconazole | (5:0.1) | 50:1 | 78 | 60 | 18 |
| 32 | Compound (I-2) + Prothioconazole | (10:0.1) | 100:1 | 81 | 63 | 17 |
| 33 | Compound (I-2) + Trifloxystrobin | (10:0.1) | 100:1 | 78 | 68 | 10 |
| 34 | Compound (I-2) + Boscalid | (1:0.1) | 10:1 | 64 | 51 | 13 |
| 35 | Compound (I-2) + Boscalid | (5:0.1) | 50:1 | 72 | 57 | 15 |
| 36 | Compound (I-2) + Boscalid | (10:0.1) | 100:1 | 81 | 61 | 20 |
| 37 | Compound (I-2) + Fluxapyroxad | (10:0.05) | 200:1 | 83 | 68 | 15 |
| 38 | Compound (I-2) + Azoxystrobin | (10:0.05) | 200:1 | 83 | 64 | 19 |
| 39 | Compound (I-2) + Azoxystrobin | (5:0.1) | 50:1 | 86 | 70 | 16 |
| 40 | Compound (I-2) + Azoxystrobin | (10:0.1) | 100:1 | 89 | 73 | 16 |
| 41 | Compound (I-2) + Folpet | (10:0.05) | 200:1 | 69 | 53 | 16 |
| 42 | Compound (I-2) + Folpet | (1:0.1) | 10:1 | 56 | 45 | 11 |
| 43 | Compound (I-2) + Folpet | (5:0.1) | 50:1 | 69 | 51 | 18 |
| 44 | Compound (I-2) + Folpet | (10:0.1) | 100:1 | 72 | 55 | 17 |
| 45 | Compound (I-2) + Mancozeb | (5:0.1) | 50:1 | 64 | 51 | 13 |
| 46 | Compound (I-2) + Mancozeb | (10:0.1) | 100:1 | 72 | 55 | 17 |
| 47 | Compound (I-2) + Benzovindiflupyr | (1:0.05) | 20:1 | 56 | 43 | 12 |

TABLE B1-continued

Table-B1: The synergistic fungicidal activity of the compositions of the present invention, wherein the representative compound of formula (I) is particularly compound (I-2) as component (1) and other components (2) selected from the groups (A) to (L) against *Alternaria solani* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 48 | Compound (I-2) + Benzovindiflupyr | (1:0.1) | 10:1 | 64 | 53 | 11 |
| 49 | Compound (I-2) + Benzovindiflupyr | (5:0.1) | 50:1 | 72 | 59 | 13 |
| 50 | Compound (I-2) + Benzovindiflupyr | (10:0.1) | 100:1 | 78 | 62 | 15 |
| 51 | Compound (I-2) + Fluindapyr | (1:0.05) | 20:1 | 56 | 43 | 12 |
| 52 | Compound (I-2) + Inpyrfluxam | (1:0.05) | 20:1 | 61 | 43 | 18 |
| 53 | Compound (I-2) + Inpyrfluxam | (10:0.05) | 200:1 | 78 | 54 | 23 |
| 54 | Compound (I-2) + Inpyrfluxam | (1:0.1) | 10:1 | 67 | 49 | 17 |
| 55 | Compound (I-2) + Inpyrfluxam | (5:0.1) | 50:1 | 75 | 55 | 20 |
| 56 | Compound (I-2) + Inpyrfluxam | (10:0.1) | 100:1 | 81 | 59 | 21 |
| 57 | Compound (I-2) + Dithianon | (1:0.05) | 20:1 | 61 | 48 | 13 |
| 58 | Compound (I-2) + Dithianon | (10:0.05) | 200:1 | 72 | 58 | 14 |
| 59 | Compound (I-2) + Dithianon | (1:0.1) | 10:1 | 67 | 51 | 16 |
| 60 | Compound (I-2) + Dithianon | (5:0.1) | 50:1 | 72 | 57 | 15 |
| 61 | Compound (I-2) + Dithianon | (10:0.1) | 100:1 | 81 | 61 | 20 |

TABLE B2

Table-B2: The synergistic fungicidal activity of the compositions of the present invention, wherein the representative compound of formula (I) is particularly compound (I-3) as component (1) and other components (2) selected from the groups (A) to (L) against *Alternaria solani* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 1 | | 35 | | |
| 2 | Compound (I-3) | 5 | | 40 | | |
| 3 | Compound (I-3) | 10 | | 47 | | |
| 4 | Mefentrifluconazole | 0.05 | | 12 | | |
| 5 | Mefentrifluconazole | 0.1 | | 26 | | |
| 6 | Fluindapyr | 0.1 | | 29 | | |
| 7 | Inpyrfluxam | 0.05 | | 14 | | |
| 8 | Inpyrfluxam | 0.1 | | 23 | | |
| 9 | Dithianon | 0.05 | | 21 | | |
| 10 | Dithianon | 0.1 | | 26 | | |
| 11 | Compound (I-3) + Mefentrifluconazole | (5:0.05) | 100:1 | 58 | 47 | 11 |
| 12 | Compound (I-3) + Mefentrifluconazole | (10:0.05) | 200:1 | 70 | 53 | 16 |
| 13 | Compound (I-3) + Mefentrifluconazole | (10:0.1) | 100:1 | 72 | 61 | 11 |
| 14 | Compound (1-3) + Fluindapyr | (1:0.1) | 10:1 | 74 | 54 | 21 |
| 15 | Compound (I-3) + Fluindapyr | (5:0.1) | 50:1 | 81 | 57 | 24 |
| 16 | Compound (I-3) + Fluindapyr | (10:0.1) | 100:1 | 84 | 62 | 21 |
| 17 | Compound (I-3) + Inpyrfluxam | (10:0.05) | 200:1 | 74 | 54 | 20 |
| 18 | Compound (I-3) + Inpyrfluxam | (1:0.1) | 10:1 | 70 | 50 | 20 |

TABLE B2-continued

Table-B2: The synergistic fungicidal activity of the compositions of the present invention, wherein the representative compound of formula (I) is particularly compound (I-3) as component (1) and other components (2) selected from the groups (A) to (L) against *Alternaria solani* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 19 | Compound (1-3) + Inpyrfluxam | (5:0.1) | 50:1 | 72 | 54 | 18 |
| 20 | Compound (I-3) + Inpyrfluxam | (10:0.1) | 100:1 | 81 | 59 | 22 |
| 21 | Compound (I-3) + Dithianon | (5:0.05) | 100:1 | 67 | 53 | 15 |
| 22 | Compound (1-3) + Dithianon | (10:0.05) | 200:1 | 74 | 58 | 16 |
| 23 | Compound (1-3) + Dithianon | (5:0.1) | 50:1 | 74 | 56 | 19 |
| 24 | Compound (I-3) + Dithianon | (10:0.1) | 100:1 | 77 | 61 | 16 |

TABLE B3

Table-B3: The synergistic fungicidal activity of the compositions of the present invention, wherein the representative compound of formula (I) is particularly compound (I-8) as component (1) and other components (2) selected from the groups (A) to (L) against *Alternaria solani* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-8) | 1 | | 26 | | |
| 2 | Compound (I-8) | 5 | | 37 | | |
| 3 | Compound (I-8) | 10 | | 47 | | |
| 4 | Picoxystrobin | 0.05 | | 23 | | |
| 5 | Picoxystrobin | 0.1 | | 26 | | |
| 6 | Benzovindiflupyr | 0.05 | | 14 | | |
| 7 | Benzovindiflupyr | 0.1 | | 29 | | |
| 8 | Fluindapyr | 0.05 | | 14 | | |
| 9 | Fluindapyr | 0.1 | | 29 | | |
| 10 | Compound (I-8) + Picoxystrobin | (10:0.05) | 200:1 | 78 | 59 | 18 |
| 11 | Compound (I-8) + Picoxystrobin | (1:0.1) | 10:1 | 78 | 45 | 32 |
| 12 | Compound (I-8) + Picoxystrobin | (5:0.1) | 50:1 | 83 | 53 | 30 |
| 13 | Compound (I-8) + Picoxystrobin | (10:0.1) | 100:1 | 89 | 61 | 28 |
| 14 | Compound (I-8) + Benzovindiflupyr | (1:0.05) | 20:1 | 53 | 37 | 16 |
| 15 | Compound (I-8) + Benzovindiflupyr | (5:0.05) | 100:1 | 61 | 46 | 15 |
| 16 | Compound (I-8) + Benzovindiflupyr | (10:0.05) | 200:1 | 78 | 55 | 23 |
| 17 | Compound (I-8) + Benzovindiflupyr | (1:0.1) | 10:1 | 61 | 48 | 13 |
| 18 | Compound (I-8) + Benzovindiflupyr | (5:0.1) | 50:1 | 67 | 55 | 12 |
| 19 | Compound (I-8) + Benzovindiflupyr | (10:0.1) | 100:1 | 81 | 63 | 18 |
| 20 | Compound (I-8) + Fluindapyr | (1:0.05) | 20:1 | 47 | 37 | 11 |
| 21 | Compound (I-8) + Fluindapyr | (5:0.05) | 100:1 | 56 | 46 | 10 |
| 22 | Compound (I-8) + Fluindapyr | (10:0.05) | 200:1 | 69 | 55 | 15 |
| 23 | Compound (I-8) + Fluindapyr | (1:0.1) | 10:1 | 61 | 48 | 13 |
| 24 | Compound (I-8) + Fluindapyr | (5:0.1) | 50:1 | 67 | 55 | 12 |
| 25 | Compound (I-8) + Fluindapyr | (10:0.1) | 100:1 | 75 | 63 | 12 |

Example C: *Erysiphe cichoracearum* Test (Cucumber)

The single compounds or the respective compound combinations were dissolved in 2% dimethyl sulfoxide/acetone and then mixed with water containing emulsifier to a calibrated spray volume of 30 mL. The test solutions were poured into spray bottles for further applications.

To test the preventive activity of the single compounds and their combinations, healthy young cucumber plants, raised in the greenhouse, were sprayed with the active compound preparation at the stated application rates inside the spray cabinets using hollow cone nozzles. One day after treatment, the plants were inoculated with a conidial suspension containing $2\times10^5$ *Erysiphe cichoracearum* inoculum. The inoculated plants were then kept in a greenhouse chamber at 22-24° C. temperature and 50-60% relative humidity for disease expression.

A visual assessment of the performance of the compounds and the respective compound combinations was carried out by rating the disease severity (0-100% scale) on treated plants 3, 7, 10 and 15 days after application. Efficacy (% control) of the compounds was calculated by comparing the disease rating in the treatment with the one of the untreated control. The compounds were also assessed for their plant compatibility by recording symptoms like necrosis, chlorosis and stunting.

The results are shown for the representative compounds of compound of formula (1) particularly, (I-2), (I-3) and (I-8) in Table $C_1$-$C_3$ respectively.

Surprisingly, the following combinations, indicated in the table below, have revealed unexpected synergistic effects:

TABLE C1

Table-C1: The synergistic fungicidal activity of the compositions of the present invention, wherein the representative compound of formula (I) is particularly compound (I-2) as component (1) and other components (2) selected from the groups (A) to (L) against *Erysiphe cichoracearum* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-2) | 1 | | 13 | | |
| 2 | Pyraclostrobin | 0.1 | | 24 | | |
| 3 | Propineb | 0.05 | | 14 | | |
| 4 | Dithianon | 0.05 | | 11 | | |
| 5 | Dithianon | 0.1 | | 18 | | |
| 6 | Compound (I-2) + Pyraclostrobin | (1:0.1) | 10:1 | 45 | 34 | 11 |
| 7 | Compound (I-2) + Propineb | (1:0.05) | 20:1 | 38 | 25 | 12 |
| 8 | Compound (I-2) + Dithianon | (1:0.05) | 20:1 | 38 | 23 | 15 |
| 9 | Compound (I-2) + Dithianon | (1:0.1) | 10:1 | 45 | 29 | 16 |

TABLE C2

Table-C2: The synergistic fungicidal activity of the compositions of the present invention, wherein the representative compounds of formula (I) is particularly compound (I-3) as component (1) and other components (2) selected from the groups (A) to (L) against *Erysiphe cichoracearum* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 1 | | 35 | | |
| 2 | Compound (I-3) | 5 | | 37 | | |
| 3 | Compound (I-3) | 10 | | 39 | | |
| 4 | Mancozeb | 0.1 | | 29 | | |
| 5 | Propineb | 0.05 | | 14 | | |
| 6 | Metiram | 0.05 | | 47 | | |
| 7 | Benzovindiflupyr | 0.05 | | 24 | | |
| 8 | Benzovindiflupyr | 0.1 | | 29 | | |
| 9 | Inpyrfluxam | 0.05 | | 29 | | |
| 10 | Inpyrfluxam | 0.1 | | 38 | | |
| 11 | Dithianon | 0.05 | | 11 | | |
| 12 | Dithianon | 0.1 | | 18 | | |
| 13 | Compound (I-3) + Mancozeb | (10:0.1) | 100:1 | 72 | 57 | 15 |
| 14 | Compound (I-3) + Propineb | (5:0.05) | 100:1 | 63 | 46 | 17 |
| 15 | Compound (1-3) + Propineb | (10:0.05) | 200:1 | 72 | 48 | 24 |
| 16 | Compound (I-3) + Metiram | (10:0.05) | 200:1 | 83 | 68 | 15 |

TABLE C2-continued

Table-C2: The synergistic fungicidal activity of the compositions of the present invention, wherein the representative compounds of formula (I) is particularly compound (I-3) as component (1) and other components (2) selected from the groups (A) to (L) against *Erysiphe cichoracearum* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 17 | Compound (I-3) + Benzovindiflupyr | (1:0.05) | 20:1 | 70 | 50 | 19 |
| 18 | Compound (I-3) + Benzovindiflupyr | (5:0.05) | 100:1 | 76 | 52 | 24 |
| 19 | Compound (I-3) + Benzovindiflupyr | (10:0.05) | 200:1 | 78 | 54 | 25 |
| 20 | Compound (I-3) + Benzovindiflupyr | (1:0.1) | 10:1 | 74 | 54 | 20 |
| 21 | Compound (1-3) + Benzovindiflupyr | (5:0.1) | 50:1 | 76 | 55 | 21 |
| 22 | Compound (I-3) + Benzovindiflupyr | (10:0.1) | 100:1 | 78 | 57 | 21 |
| 23 | Compound (I-3) + Inpyrfluxa | (5:0.05) | 100:1 | 76 | 55 | 21 |
| 24 | Compound (1-3) + Inpyrfluxam | (10:0.05) | 200:1 | 80 | 57 | 24 |
| 25 | Compound (I-3) + Inpyrfluxam | (10:0.1) | 100:1 | 83 | 62 | 20 |
| 26 | Compound (I-3) + Dithianon | (1:0.05) | 20:1 | 61 | 42 | 19 |
| 27 | Compound (I-3) + Dithianon | (5:0.05) | 100:1 | 74 | 44 | 30 |
| 28 | Compound (I-3) + Dithianon | (10:0.05) | 200:1 | 78 | 46 | 32 |
| 29 | Compound (I-3) + Dithianon | (1:0.1) | 10:1 | 65 | 47 | 19 |
| 30 | Compound (I-3) + Dithianon | (5:0.1) | 50:1 | 76 | 48 | 28 |
| 31 | Compound (I-3) + Dithianon | (10:0.1) | 100:1 | 80 | 50 | 30 |

TABLE C3

Table-C3: The synergistic fungicidal activity of the compositions of the present invention, wherein the representative compounds of formula (I) is particularly compound (I-8) as component (1) and other components (2) selected from the groups (A) to (L) against *Erysiphe cichoracearum* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-8) | 1 | | 19 | | |
| 2 | Compound (I-8) | 5 | | 25 | | |
| 3 | Compound (I-8) | 10 | | 31 | | |
| 4 | Mefentrifluconazole | 0.1 | | 24 | | |
| 5 | Pyraclostrobin | 0.1 | | 24 | | |
| 6 | Benzovindiflupyr | 0.05 | | 24 | | |
| 7 | Benzovindiflupyr | 0.1 | | 29 | | |
| 8 | Dithianon | 0.05 | | 11 | | |
| 9 | Dithianon | 0.1 | | 18 | | |
| 10 | Compound (I-8) + Mefentrifluconazole | (10:0.1) | 100:1 | 58 | 48 | 10 |
| 11 | Compound (I-8) + Pyraclostrobin | (10:0.1) | 100:1 | 58 | 48 | 10 |
| 12 | Compound (I-8) + Benzovindiflupyr | (10:0.05) | 200:1 | 58 | 48 | 10 |
| 13 | Compound (I-8) + Benzovindiflupyr | (1:0.1) | 10:1 | 55 | 42 | 13 |
| 14 | Compound (I-8) + Benzovindiflupyr | (5:0.1) | 50:1 | 65 | 47 | 18 |
| 15 | Compound (I-8) + Benzovindiflupyr | (10:0.1) | 100:1 | 65 | 51 | 14 |
| 16 | Compound (I-8) + Dithianon | (1:0.05) | 20:1 | 40 | 28 | 12 |

TABLE C3-continued

Table-C3: The synergistic fungicidal activity of the compositions of the present invention, wherein the representative compounds of formula (I) is particularly compound (I-8) as component (1) and other components (2) selected from the groups (A) to (L) against *Erysiphe cichoracearum* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 17 | Compound (I-8) + Dithianon | (5:0.05) | 100:1 | 48 | 33 | 14 |
| 18 | Compound (I-8) + Dithianon | (10:0.05) | 200:1 | 53 | 39 | 14 |
| 19 | Compound (I-8) + Dithianon | (1:0.1) | 10:1 | 53 | 33 | 19 |
| 20 | Compound (I-8) + Dithianon | (5:0.1) | 50:1 | 58 | 39 | 19 |
| 21 | Compound (I-8) + Dithianon | (10:0.1) | 100:1 | 65 | 44 | 21 |

Example D: *Phakopsora pachyrhizi* Test (Soybean)

The single compounds or the respective compound combinations were dissolved in 2% dimethyl sulfoxide/acetone and then mixed with water containing an emulsifier to a calibrated spray volume of 30 mL. The test solutions were poured into spray bottles for further applications.

To test the preventive activity of the single compounds and their combinations, healthy young soybean plants, raised in the greenhouse, were sprayed with the active compound preparation at the stated application rates inside the spray cabinets using hollow cone nozzles. One day after treatment, the plants were inoculated with a suspension containing $2\times10^5$ *Phakopsora pachyrhizi* conidia. The inoculated plants were then kept in a greenhouse chamber at 22-24° C. temperature and 80-90% relative humidity for disease expression.

A visual assessment of the performance of the compounds and respective compound combinations was carried out by rating the disease severity (0-100% scale) on treated plants 3, 7, 10 and 15 days after application. Efficacy (% control) of the compounds was calculated by comparing the disease rating in the treatment with the one of the untreated control. The compounds were also assessed for their plant compatibility by recording symptoms like necrosis, chlorosis and stunting.

The results are shown for the representative compounds of compound of formula (I) particularly, (I-2), (I-3) and (I-8) in Table D1-D3 respectively.

Surprisingly, the following combinations, indicated in the table below, have revealed unexpected synergistic effects:

TABLE D1

Table-D1: The synergistic fungicidal activity of the compositions of the present invention, wherein the representative compound of formula (I) is particularly compound (I-2) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-2) | 0.0001 | | 40 | | |
| 2 | Compound (I-2) | 0.001 | | 50 | | |
| 3 | Compound (I-2) | 0.01 | | 62 | | |
| 4 | Prothioconazole | 0.1 | | 48 | | |
| 5 | Trifloxystrobin | 0.1 | | 32 | | |
| 6 | Boscalid | 0.05 | | 27 | | |
| 7 | Boscalid | 0.1 | | 32 | | |
| 8 | Bixafen | 0.05 | | 15 | | |
| 9 | Bixafen | 0.1 | | 22 | | |
| 10 | Difenoconazole | 0.1 | | 24 | | |
| 11 | Azoxystrobin | 0.05 | | 15 | | |
| 12 | Azoxystrobin | 0.1 | | 22 | | |
| 13 | Picoxystrobin | 0.05 | | 20 | | |
| 14 | Picoxystrobin | 0.1 | | 28 | | |
| 15 | Fluazinam | 0.05 | | 2 | | |
| 16 | Fluazinam | 0.1 | | 10 | | |
| 17 | Folpet | 0.05 | | 5 | | |
| 18 | Folpet | 0.1 | | 12 | | |
| 19 | Tebuconazole | 0.05 | | 38 | | |
| 20 | Tebuconazole | 0.1 | | 44 | | |
| 21 | Fluopyram | 0.05 | | 7 | | |
| 22 | Fluopyram | 0.1 | | 10 | | |
| 23 | Mancozeb | 0.05 | | 12 | | |
| 24 | Mancozeb | 0.1 | | 15 | | |

TABLE D1-continued

Table-D1: The synergistic fungicidal activity of the compositions of the present invention, wherein the representative compound of formula (I) is particularly compound (I-2) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 25 | Propineb | 0.05 | | 20 | | |
| 26 | Propineb | 0.1 | | 33 | | |
| 27 | Metiram | 0.05 | | 17 | | |
| 28 | Metiram | 0.1 | | 37 | | |
| 29 | Benzovindiflupyr | 0.05 | | 27 | | |
| 30 | Benzovindiflupyr | 0.1 | | 38 | | |
| 31 | Fluindapyr | 0.05 | | 20 | | |
| 32 | Fluindapyr | 0.1 | | 30 | | |
| 33 | Inpyrfluxam | 0.05 | | 18 | | |
| 34 | Inpyrfluxam | 0.1 | | 30 | | |
| 35 | Dithianon | 0.05 | | 15 | | |
| 36 | Dithianon | 0.1 | | 24 | | |
| 37 | Compound (I-2) + Prothioconazole | (0.001:0.1) | 0.01:1 | 87 | 74 | 13 |
| 38 | Compound (I-2) + Prothioconazole | (0.01:0.1) | 0.1:1 | 90 | 80 | 10 |
| 39 | Compound (I-2) + Trifloxystrobin | (0.01:0.1) | 0.1:1 | 87 | 74 | 13 |
| 40 | Compound (I-2) + Boscalid | (0.0001:0.05) | 0.002:1 | 67 | 56 | 10 |
| 41 | Compound (I-2) + Boscalid | (0.001:0.05) | 0.02:1 | 77 | 64 | 13 |
| 42 | Compound (I-2) + Boscalid | (0.0001:0.1) | 0.001:1 | 77 | 59 | 17 |
| 43 | Compound (I-2) + Boscalid | (0.001:0.1) | 0.01:1 | 80 | 66 | 14 |
| 44 | Compound (I-2) + Boscalid | (0.01:0.1) | 0.1:1 | 87 | 74 | 13 |
| 45 | Compound (I-2) + Bixafen | (0.0001:0.05) | 0.002:1 | 73 | 49 | 24 |
| 46 | Compound (I-2) + Bixafen | (0.001:0.05) | 0.02:1 | 80 | 58 | 23 |
| 47 | Compound (I-2) + Bixafen | (0.01:0.05) | 0.2:1 | 87 | 68 | 19 |
| 48 | Compound (I-2) + Bixafen | (0.0001:0.1) | 0.001:1 | 80 | 53 | 27 |
| 49 | Compound (I-2) + Bixafen | (0.001:0.1) | 0.01:1 | 87 | 61 | 26 |
| 50 | Compound (I-2) + Bixafen | (0.01:0.1) | 0.1:1 | 90 | 70 | 20 |
| 51 | Compound (I-2) + Difenoconazole | (0.001:0.1) | 0.01:1 | 73 | 62 | 11 |
| 52 | Compound (I-2) + Difenoconazole | (0.01:0.1) | 0.1:1 | 87 | 71 | 16 |
| 53 | Compound (I-2) + Azoxystrobin | (0.0001:0.05) | 0.002:1 | 70 | 49 | 21 |
| 54 | Compound (I-2) + Azoxystrobin | (0.001:0.05) | 0.02:1 | 73 | 58 | 16 |
| 55 | Compound (I-2) + Azoxystrobin | (0.01:0.05) | 0.2:1 | 87 | 68 | 19 |
| 56 | Compound (I-2) + Azoxystrobin | (0.0001:0.1) | 0.001:1 | 77 | 53 | 23 |
| 57 | Compound (I-2) + Azoxystrobin | (0.001:0.1) | 0.01:1 | 83 | 61 | 22 |
| 58 | Compound (I-2) + Azoxystrobin | (0.01:0.1) | 0.1:1 | 90 | 70 | 20 |
| 59 | Compound (I-2) + Picoxystrobin | (0.001:0.05) | 0.02:1 | 70 | 60 | 10 |
| 60 | Compound (I-2) + Picoxystrobin | (0.0001:0.1) | 0.001:1 | 80 | 57 | 23 |
| 61 | Compound (I-2) + Picoxystrobin | (0.001:0.1) | 0.01:1 | 77 | 64 | 13 |
| 62 | Compound (I-2) + Fluazinam | (0.0001:0.05) | 0.002:1 | 57 | 41 | 15 |
| 63 | Compound (I-2) + Fluazinam | (0.001:0.05) | 0.02:1 | 63 | 51 | 12 |
| 64 | Compound (I-2) + Fluazinam | (0.01:0.05) | 0.2:1 | 80 | 63 | 17 |
| 65 | Compound (I-2) + Fluazinam | (0.0001:0.1) | 0.001:1 | 70 | 46 | 24 |

TABLE D1-continued

Table-D1: The synergistic fungicidal activity of the compositions of the present invention, wherein the representative compound of formula (I) is particularly compound (I-2) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 66 | Compound (I-2) + Fluazinam | (0.001:0.1) | 0.01:1 | 77 | 55 | 22 |
| 67 | Compound (I-2) + Fluazinam | (0.01:0.1) | 0.1:1 | 83 | 66 | 18 |
| 68 | Compound (I-2) + Folpet | (0.0001:0.05) | 0.002:1 | 73 | 43 | 30 |
| 69 | Compound (I-2) + Folpet | (0.001:0.05) | 0.02:1 | 83 | 53 | 31 |
| 70 | Compound (I-2) + Folpet | (0.0001:0.1) | 0.001:1 | 90 | 47 | 43 |
| 71 | Compound (I-2) + Folpet | (0.001:0.1) | 0.01:1 | 93 | 56 | 37 |
| 72 | Compound (I-2) + Folpet | (0.01:0.1) | 0.1:1 | 97 | 67 | 30 |
| 73 | Compound (I-2) + Tebuconazole | (0.0001:0.05) | 0.002:1 | 77 | 63 | 14 |
| 74 | Compound (I-2) + Tebuconazole | (0.001:0.05) | 0.02:1 | 80 | 69 | 11 |
| 75 | Compound (I-2) + Tebuconazole | (0.0001:0.1) | 0.001:1 | 77 | 66 | 10 |
| 76 | Compound (I-2) + Fluopyram | (0.0001:0.05) | 0.002:1 | 87 | 44 | 42 |
| 77 | Compound (I-2) + Fluopyram | (0.001:0.05) | 0.02:1 | 90 | 54 | 37 |
| 78 | Compound (I-2) + Fluopyram | (0.01:0.05) | 0.2:1 | 93 | 65 | 29 |
| 79 | Compound (I-2) + Fluopyram | (0.0001:0.1) | 0.001:1 | 90 | 46 | 44 |
| 80 | Compound (I-2) + Fluopyram | (0.001:0.1) | 0.01:1 | 93 | 55 | 38 |
| 81 | Compound (I-2) + Fluopyram | (0.01:0.1) | 0.1:1 | 97 | 66 | 31 |
| 82 | Compound (I-2) + Mancozeb | (0.0001:0.05) | 0.002:1 | 80 | 47 | 33 |
| 83 | Compound (I-2) + Mancozeb | (0.001:0.05) | 0.02:1 | 83 | 56 | 27 |
| 84 | Compound (I-2) + Mancozeb | (0.0001:0.1) | 0.001:1 | 80 | 49 | 31 |
| 85 | Compound (I-2) + Mancozeb | (0.001:0.1) | 0.01:1 | 87 | 58 | 29 |
| 86 | Compound (I-2) + Mancozeb | (0.01:0.1) | 0.1:1 | 90 | 68 | 22 |
| 87 | Compound (I-2) + Propineb | (0.0001:0.05) | 0.002:1 | 83 | 52 | 31 |
| 88 | Compound (I-2) + Propineb | (0.001:0.05) | 0.02:1 | 87 | 60 | 27 |
| 89 | Compound (I-2) + Propineb | (0.0001:0.1) | 0.001:1 | 90 | 60 | 30 |
| 90 | Compound (I-2) + Propineb | (0.001:0.1) | 0.01:1 | 93 | 67 | 27 |
| 91 | Compound (I-2) + Metiram | (0.0001:0.05) | 0.002:1 | 80 | 50 | 30 |
| 92 | Compound (I-2) + Metiram | (0.001:0.05) | 0.02:1 | 83 | 59 | 25 |
| 93 | Compound (I-2) + Metiram | (0.0001:0.1) | 0.001:1 | 83 | 62 | 21 |
| 94 | Compound (I-2) + Metiram | (0.001:0.1) | 0.01:1 | 87 | 69 | 18 |
| 95 | Compound (I-2) + Benzovindiflupyr | (0.0001:0.05) | 0.002:1 | 80 | 56 | 24 |
| 96 | Compound (I-2) + Benzovindiflupyr | (0.001:0.05) | 0.02:1 | 83 | 64 | 20 |
| 97 | Compound (I-2) + Benzovindiflupyr | (0.0001:0.1) | 0.001:1 | 87 | 63 | 24 |
| 98 | Compound (I-2) + Benzovindiflupyr | (0.001:0.1) | 0.01:1 | 90 | 69 | 21 |
| 99 | Compound (I-2) + Benzovindiflupyr | (0.01:0.1) | 0.1:1 | 93 | 76 | 17 |
| 100 | Compound (I-2) + Fluindapyr | (0.0001:0.05) | 0.002:1 | 67 | 52 | 15 |

TABLE D1-continued

Table-D1: The synergistic fungicidal activity of the compositions of the present invention, wherein the representative compound of formula (I) is particularly compound (I-2) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 101 | Compound (I-2) + Fluindapyr | (0.001:0.05) | 0.02:1 | 70 | 60 | 10 |
| 102 | Compound (I-2) + Fluindapyr | (0.0001:0.1) | 0.001:1 | 70 | 58 | 12 |
| 103 | Compound (I-2) + Fluindapyr | (0.01:0.1) | 0.1:1 | 87 | 73 | 13 |
| 104 | Compound (I-2) + Inpyrfluxam | (0.0001:0.05) | 0.002:1 | 80 | 51 | 29 |
| 105 | Compound (I-2) + Inpyrfluxam | (0.001:0.05) | 0.02:1 | 83 | 59 | 24 |
| 106 | Compound (I-2) + Inpyrfluxam | (0.01:0.05) | 0.2:1 | 87 | 69 | 18 |
| 107 | Compound (I-2) + Inpyrfluxam | (0.0001:0.1) | 0.001:1 | 83 | 58 | 25 |
| 108 | Compound (I-2) + Inpyrfluxam | (0.001:0.1) | 0.01:1 | 87 | 65 | 22 |
| 109 | Compound (I-2) + Dithianon | (0.0001:0.05) | 0.002:1 | 73 | 49 | 24 |
| 110 | Compound (I-2) + Dithianon | (0.001:0.05) | 0.02:1 | 77 | 58 | 19 |
| 111 | Compound (I-2) + Dithianon | (0.0001:0.1) | 0.001:1 | 87 | 54 | 32 |
| 112 | Compound (I-2) + Dithianon | (0.001:0.1) | 0.01:1 | 90 | 62 | 28 |
| 113 | Compound (I-2) + Dithianon | (0.01:0.1) | 0.1:1 | 93 | 71 | 22 |

TABLE D2

Table-D2: The synergistic fungicidal activity of the compositions of the present invention, wherein the representative compounds of formula (I) is particularly compound (I-3) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 0.0001 | | 43 | | |
| 2 | Compound (I-3) | 0.001 | | 50 | | |
| 3 | Tebuconazole | 0.1 | | 44 | | |
| 4 | Compound (I-3) + Tebuconazole | (0.0001:0.1) | 0.001:1 | 83 | 68 | 15 |
| 5 | Compound (I-3) + Tebuconazole | (0.001:0.1) | 0.01:1 | 87 | 72 | 15 |

TABLE D3

Table-D3: The synergistic fungicidal activity of the compositions of the present invention, wherein the representative compounds of formula (I) is particularly compound (I-8) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-8) | 0.0001 | | 37 | | |
| 2 | Compound (I-8) | 0.001 | | 47 | | |
| 3 | Compound (I-8) | 0.01 | | 60 | | |
| 4 | Mefentrifluconazole | 0.05 | | 32 | | |
| 5 | Mefentrifluconazole | 0.1 | | 44 | | |
| 6 | Prothioconazole | 0.1 | | 48 | | |
| 7 | Pyraclostrobin | 0.05 | | 37 | | |
| 8 | Pyraclostrobin | 0.1 | | 46 | | |
| 9 | Trifloxystrobin | 0.1 | | 32 | | |

TABLE D3-continued

Table-D3: The synergistic fungicidal activity of the compositions of the present invention, wherein the representative compounds of formula (I) is particularly compound (I-8) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 10 | Boscalid | 0.1 | | 32 | | |
| 11 | Bixafen | 0.05 | | 15 | | |
| 12 | Bixafen | 0.1 | | 22 | | |
| 13 | Difenoconazole | 0.05 | | 17 | | |
| 14 | Difenoconazole | 0.1 | | 24 | | |
| 15 | Picoxystrobin | 0.1 | | 28 | | |
| 16 | Fluazinam | 0.05 | | 2 | | |
| 17 | Fluazinam | 0.1 | | 10 | | |
| 18 | Folpet | 0.05 | | 5 | | |
| 19 | Folpet | 0.1 | | 12 | | |
| 20 | Tebuconazole | 0.05 | | 38 | | |
| 21 | Tebuconazole | 0.1 | | 44 | | |
| 22 | Fluopyram | 0.1 | | 10 | | |
| 23 | Mancozeb | 0.1 | | 15 | | |
| 24 | Benzovindiflupyr | 0.05 | | 27 | | |
| 25 | Benzovindiflupyr | 0.1 | | 38 | | |
| 26 | Inpyrfluxam | 0.05 | | 18 | | |
| 27 | Inpyrfluxam | 0.1 | | 30 | | |
| 28 | Compound (I-8) + Mefentrifluconazole | (0.0001:0.05) | 0.002:1 | 67 | 57 | 10 |
| 29 | Compound (I-8) + Mefentrifluconazole | (0.0001:0.1) | 0.001:1 | 77 | 65 | 12 |
| 30 | Compound (I-8) + Mefentrifluconazole | (0.001:0.1) | 0.01:1 | 83 | 70 | 13 |
| 31 | Compound (I-8) + Prothioconazole | (0.0001:0.1) | 0.001:1 | 80 | 67 | 13 |
| 32 | Compound (I-8) + Prothioconazole | (0.001:0.1) | 0.01:1 | 83 | 72 | 11 |
| 33 | Compound (I-8) + Prothioconazole | (0.01:0.1) | 0.1:1 | 93 | 79 | 14 |
| 34 | Compound (I-8) + Pyraclostrobin | (0.0001:0.05) | 0.002:1 | 73 | 60 | 13 |
| 35 | Compound (I-8) + Pyraclostrobin | (0.001:0.05) | 0.02:1 | 80 | 67 | 13 |
| 36 | Compound (I-8) + Pyraclostrobin | (0.01:0.05) | 0.2:1 | 90 | 75 | 15 |
| 37 | Compound (I-8) + Pyraclostrobin | (0.0001:0.1) | 0.001:1 | 80 | 66 | 14 |
| 38 | Compound (I-8) + Pyraclostrobin | (0.001:0.1) | 0.01:1 | 87 | 71 | 15 |
| 39 | Compound (I-8) + Pyraclostrobin | (0.01:0.1) | 0.1:1 | 100 | 78 | 22 |
| 40 | Compound (I-8) + Trifloxystrobin | (0.0001:0.1) | 0.001:1 | 80 | 57 | 23 |
| 41 | Compound (I-8) + Trifloxystrobin | (0.001:0.1) | 0.01:1 | 87 | 64 | 23 |
| 42 | Compound (I-8) + Trifloxystrobin | (0.01:0.1) | 0.1:1 | 97 | 73 | 24 |
| 43 | Compound (I-8) + Boscalid | (0.0001:0.1) | 0.001:1 | 70 | 57 | 13 |
| 44 | Compound (I-8) + Boscalid | (0.01:0.1) | 0.1:1 | 83 | 73 | 11 |
| 45 | Compound (I-8) + Bixafen | (0.0001:0.05) | 0.002:1 | 67 | 46 | 20 |
| 46 | Compound (I-8) + Bixafen | (0.001:0.05) | 0.02:1 | 83 | 55 | 28 |
| 47 | Compound (I-8) + Bixafen | (0.01:0.05) | 0.2:1 | 87 | 66 | 21 |
| 48 | Compound (I-8) + Bixafen | (0.0001:0.1) | 0.001:1 | 80 | 51 | 29 |
| 49 | Compound (I-8) + Bixafen | (0.001:0.1) | 0.01:1 | 87 | 59 | 28 |
| 50 | Compound (I-8) + Bixafen | (0.01:0.1) | 0.1:1 | 90 | 69 | 21 |
| 51 | Compound (I-8) + Difenoconazole | (0.0001:0.05) | 0.002:1 | 70 | 48 | 22 |
| 52 | Compound (I-8) + Difenoconazole | (0.001:0.05) | 0.02:1 | 73 | 56 | 17 |
| 53 | Compound (I-8) + Difenoconazole | (0.01:0.05) | 0.2:1 | 77 | 67 | 10 |
| 54 | Compound (I-8) + Difenoconazole | (0.0001:0.1) | 0.001:1 | 80 | 52 | 28 |
| 55 | Compound (I-8) + Difenoconazole | (0.001:0.1) | 0.01:1 | 83 | 60 | 24 |
| 56 | Compound (I-8) + Difenoconazole | (0.01:0.1) | 0.1:1 | 87 | 70 | 17 |
| 57 | Compound (I-8) + Picoxystrobin | (0.0001:0.1) | 0.001:1 | 73 | 55 | 19 |
| 58 | Compound (I-8) + Picoxystrobin | (0.001:0.1) | 0.01:1 | 80 | 62 | 18 |
| 59 | Compound (I-8) + Picoxystrobin | (0.01:0.1) | 0.1:1 | 83 | 71 | 12 |
| 60 | Compound (I-8) + Fluazinam | (0.0001:0.05) | 0.002:1 | 53 | 38 | 15 |
| 61 | Compound (I-8) + Fluazinam | (0.001:0.05) | 0.02:1 | 60 | 48 | 12 |
| 62 | Compound (I-8) + Fluazinam | (0.0001:0.1) | 0.001:1 | 67 | 43 | 23 |
| 63 | Compound (I-8) + Fluazinam | (0.001:0.1) | 0.01:1 | 87 | 52 | 34 |
| 64 | Compound (I-8) + Fluazinam | (0.01:0.1) | 0.1:1 | 90 | 64 | 26 |
| 65 | Compound (I-8) + Folpet | (0.0001:0.05) | 0.002:1 | 80 | 40 | 40 |
| 66 | Compound (I-8) + Folpet | (0.001:0.05) | 0.02:1 | 83 | 50 | 34 |
| 67 | Compound (I-8) + Folpet | (0.01:0.05) | 0.2:1 | 87 | 62 | 25 |
| 68 | Compound (I-8) + Folpet | (0.0001:0.1) | 0.001:1 | 87 | 45 | 42 |
| 69 | Compound (I-8) + Folpet | (0.001:0.1) | 0.01:1 | 90 | 53 | 37 |
| 70 | Compound (I-8) + Folpet | (0.01:0.1) | 0.1:1 | 100 | 65 | 35 |
| 71 | Compound (I-8) + Tebuconazole | (0.0001:0.05) | 0.002:1 | 73 | 61 | 12 |
| 72 | Compound (I-8) + Tebuconazole | (0.001:0.05) | 0.02:1 | 77 | 67 | 10 |
| 73 | Compound (I-8) + Tebuconazole | (0.0001:0.1) | 0.001:1 | 77 | 65 | 12 |
| 74 | Compound (I-8) + Tebuconazole | (0.001:0.1) | 0.01:1 | 80 | 70 | 10 |
| 75 | Compound (I-8) + Fluopyram | (0.0001:0.1) | 0.001:1 | 57 | 43 | 13 |
| 76 | Compound (I-8) + Mancozeb | (0.0001:0.1) | 0.001:1 | 57 | 46 | 10 |
| 77 | Compound (I-8) + Benzovindiflupyr | (0.0001:0.05) | 0.002:1 | 77 | 54 | 23 |

TABLE D3-continued

Table-D3: The synergistic fungicidal activity of the compositions of the present invention, wherein the representative compounds of formula (I) is particularly compound (I-8) as component (1) and other components (2) selected from the groups (A) to (L) against *Phakopsora pachyrhizi* in soybean are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 78 | Compound (I-8) + Benzovindiflupyr | (0.001:0.05) | 0.02:1 | 80 | 61 | 19 |
| 79 | Compound (I-8) + Benzovindiflupyr | (0.01:0.05) | 0.2:1 | 83 | 71 | 13 |
| 80 | Compound (I-8) + Benzovindiflupyr | (0.0001:0.1) | 0.001:1 | 80 | 61 | 19 |
| 81 | Compound (I-8) + Benzovindiflupyr | (0.001:0.1) | 0.01:1 | 83 | 67 | 16 |
| 82 | Compound (I-8) + Benzovindiflupyr | (0.01:0.1) | 0.1:1 | 87 | 75 | 11 |
| 83 | Compound (I-8) + Inpyrfluxam | (0.0001:0.05) | 0.002:1 | 60 | 48 | 12 |
| 84 | Compound (I-8) + Inpyrfluxam | (0.001:0.05) | 0.02:1 | 67 | 57 | 10 |
| 85 | Compound (I-8) + Inpyrfluxam | (0.0001:0.1) | 0.001:1 | 80 | 56 | 24 |
| 86 | Compound (I-8) + Inpyrfluxam | (0.001:0.1) | 0.01:1 | 83 | 63 | 20 |
| 87 | Compound (I-8) + Inpyrfluxam | (0.01:0.1) | 0.1:1 | 90 | 72 | 18 |

Example E: *Parastagonospora Nodorum/Septoria Nodorum/Stagnospora Nodorum* (Wheat)

The single compounds or compound combinations were dissolved in 2% DMSO/Acetone and then mixed with water containing emulsifier to a calibrated spray volume of 30 mL. The spray solutions were poured into spray bottles for further applications.

To test the preventive activity of the single compounds and the their combinations, healthy young wheat plants, raised in the greenhouse, were sprayed with the active compound preparation at the stated application rates inside the spray cabinets using hollow cone nozzles. One day after treatment, the plants were inoculated with a suspension containing $2.8\times10^6$ *Stagnospora nodorum* inoculum. The inoculated plants were then kept in a greenhouse chamber at 22-25° C. temperature and 90-100% relative humidity for disease expression.

A visual assessment of the performance of the compounds and compound combinations was carried out by rating the disease severity (0-100% scale) on treated plants 3, 7 and 10 days after application. Efficacy (% control) of the compounds was calculated by comparing the disease rating in the treatment with the one of the untreated control. The compounds were also assessed for their plant compatibility by recording symptoms like necrosis, chlorosis & stunting.

The results are shown for the representative compounds of compound of formula (I) particularly, (I-2) in Table E1.

Surprisingly, the following combinations, indicated in the table below, have revealed unexpected synergistic effects:

TABLE E1

Table-E1: The synergistic fungicidal activity of the compositions of the present invention, wherein the representative compounds of formula (I) is particularly compound (I-2) as component (1) and other components (2) selected from the groups (A) to (L) against *Septoria nodorum* in wheat are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-2) | 1 | | 17 | | |
| 2 | Compound (I-2) | 5 | | 20 | | |
| 3 | Compound (I-2) | 10 | | 43 | | |
| 4 | Fluxapyroxad | 0.05 | | 3 | | |
| 5 | Fluxapyroxad | 0.1 | | 5 | | |
| 6 | Fluazinam | 0.1 | | 21 | | |
| 7 | Metominostrobin | 0.05 | | 6 | | |
| 8 | Metominostrobin | 0.1 | | 12 | | |
| 9 | Fluopyram | 0.05 | | 8 | | |
| 10 | Fluopyram | 0.1 | | 21 | | |
| 11 | Inpyrfluxam | 0.05 | | 12 | | |
| 12 | Dithianon | 0.05 | | 11 | | |
| 13 | Dithianon | 0.1 | | 16 | | |
| 14 | Compound (I-2) + Fluxapyroxad | (5:0.05) | 100:1 | 37 | 22 | 14 |
| 15 | Compound (I-2) + Fluxapyroxad | (1:0.1) | 10:1 | 39 | 21 | 19 |
| 16 | Compound (I-2) + Fluxapyroxad | (5:0.1) | 50:1 | 50 | 24 | 26 |
| 17 | Compound (I-2) + Fluazinam | (5:0.1) | 50:1 | 50 | 37 | 13 |
| 18 | Compound (I-2) + Metominostrobin | (1:0.1) | 10:1 | 50 | 27 | 23 |
| 19 | Compound (I-2) + Metominostrobin | (5:0.1) | 50:1 | 58 | 30 | 28 |
| 20 | Compound (I-2) + Metominostrobin | (10:0.1) | 100:1 | 68 | 50 | 18 |
| 21 | Compound (I-2) + Fluopyram | (5:0.05) | 100:1 | 42 | 26 | 16 |
| 22 | Compound (I-2) + Fluopyram | (5:0.1) | 50:1 | 47 | 37 | 11 |
| 23 | Compound (I-2) + Inpyrfluxam | (1:0.05) | 20:1 | 42 | 27 | 15 |
| 24 | Compound (I-2) + Inpyrfluxam | (5:0.05) | 100:1 | 50 | 30 | 20 |
| 25 | Compound (I-2) + Dithianon | (1:0.05) | 20:1 | 47 | 26 | 22 |

TABLE E1-continued

Table-E1: The synergistic fungicidal activity of the compositions of the present invention, wherein the representative compounds of formula (I) is particularly compound (I-2) as component (1) and other components (2) selected from the groups (A) to (L) against *Septoria nodorum* in wheat are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 26 | Compound (I-2) + Dithianon | (5:0.05) | 100:1 | 55 | 29 | 26 |
| 27 | Compound (I-2) + Dithianon | (1:0.1) | 10:1 | 53 | 30 | 23 |
| 28 | Compound (I-2) + Dithianon | (5:0.1) | 50:1 | 58 | 33 | 25 |

Example F: *Botrytis cinerea* Test (Tomato)

The single compounds or compound combinations were dissolved in 2% dimethyl sulfoxide/acetone and then mixed with water containing emulsifier to a calibrated spray volume of 30 mL. The test solutions were poured into spray bottles for further applications.

To test the preventive activity of the single compounds and their combinations, healthy young tomato plants, raised in the greenhouse, were sprayed with the active compound preparation at the stated application rates inside the spray cabinets using hollow cone nozzles. One day after treatment, the plants were inoculated with a spore suspension containing $1.2\times10^6$ *Botrytis cinerea* inoculum and 2% malt. The inoculated plants were then kept in a greenhouse chamber at 18-20° C. temperature and 90-100% relative humidity for disease expression.

A visual assessment of the performance of the compounds and compound combinations was carried out by rating the disease severity (0-100% scale) on treated plants 3, 7, 10 and 15 days after application. Efficacy (% control) of the compounds was calculated by comparing the disease rating in the treatment with the one of the untreated control. The compounds were also assessed for their plant compatibility by recording symptoms like necrosis, chlorosis and stunting.

The results are shown for the representative compounds of compound of formula (I) particularly. (I-2) and (I-3) in Table F1-F2 respectively.

Surprisingly, the following combinations, indicated in the table below, have revealed unexpected synergistic effects:

TABLE F1

Table-F1: The synergistic fungicidal activity of the compositions of the present invention, wherein the representative compound of formula (I) is particularly compound (I-2) as component (1) and other components (2) selected from the groups (A) to (L) against *Botrytis cinerea* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-2) | 1 | | 20 | | |
| 2 | Compound (I-2) | 5 | | 27 | | |
| 3 | Compound (I-2) | 10 | | 47 | | |
| 4 | Mefentrifluconazole | 0.05 | | 31 | | |
| 5 | Mefentrifluconazole | 0.1 | | 38 | | |
| 6 | Trifloxystrobin | 0.1 | | 33 | | |
| 7 | Metominostrobin | 0.05 | | 28 | | |
| 8 | Metominostrobin | 0.1 | | 40 | | |
| 9 | Folpet | 0.05 | | 24 | | |
| 10 | Folpet | 0.1 | | 38 | | |
| 11 | Mancozeb | 0.05 | | 19 | | |
| 12 | Mancozeb | 0.1 | | 24 | | |
| 13 | Propineb | 0.05 | | 15 | | |
| 14 | Propineb | 0.1 | | 22 | | |
| 15 | Compound (I-2) + Mefentrifluconazole | (5:0.05) | 100:1 | 68 | 49 | 19 |
| 16 | Compound (I-2) + Mefentrifluconazole | (1:0.1) | 10:1 | 68 | 50 | 18 |
| 17 | Compound (I-2) + Mefentrifluconazole | (5:0.1) | 50:1 | 71 | 55 | 17 |
| 18 | Compound (I-2) + Trifloxystrobin | (1:0.1) | 10:1 | 58 | 46 | 11 |
| 19 | Compound (I-2) + Trifloxystrobin | (5:0.1) | 50:1 | 66 | 51 | 15 |
| 20 | Compound (I-2) + Metominostrobin | (1:0.05) | 20:1 | 57 | 42 | 14 |
| 21 | Compound (I-2) + Metominostrobin | (5:0.05) | 100:1 | 70 | 47 | 23 |
| 22 | Compound (I-2) + Metominostrobin | (10:0.05) | 200:1 | 76 | 62 | 14 |
| 23 | Compound (I-2) + Metominostrobin | (1:0.1) | 10:1 | 70 | 52 | 18 |
| 24 | Compound (I-2) + Metominostrobin | (5:0.1) | 50:1 | 78 | 56 | 22 |
| 25 | Compound (I-2) + Folpet | (1:0.05) | 20:1 | 68 | 39 | 28 |
| 26 | Compound (I-2) + Folpet | (5:0.05) | 100:1 | 70 | 44 | 26 |
| 27 | Compound (I-2) + Folpet | (10:0.05) | 200:1 | 81 | 59 | 22 |
| 28 | Compound (I-2) + Folpet | (1:0.1) | 10:1 | 68 | 50 | 17 |
| 29 | Compound (I-2) + Folpet | (5:0.1) | 50:1 | 73 | 55 | 18 |
| 30 | Compound (I-2) + Mancozeb | (1:0.05) | 20:1 | 47 | 35 | 11 |
| 31 | Compound (I-2) + Mancozeb | (5:0.05) | 100:1 | 53 | 41 | 13 |
| 32 | Compound (I-2) + Mancozeb | (1:0.1) | 10:1 | 53 | 39 | 14 |
| 33 | Compound (I-2) + Mancozeb | (5:0.1) | 50:1 | 60 | 44 | 16 |
| 34 | Compound (I-2) + Propineb | (5:0.05) | 100:1 | 57 | 38 | 19 |

TABLE F1-continued

Table-F1: The synergistic fungicidal activity of the compositions of the present invention, wherein the representative compound of formula (I) is particularly compound (I-2) as component (1) and other components (2) selected from the groups (A) to (L) against *Botrytis cinerea* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 35 | Compound (I-2) + Propineb | (1:0.1) | 10:1 | 53 | 38 | 16 |
| 36 | Compound (I-2) + Propineb | (5:0.1) | 50:1 | 63 | 43 | 21 |

TABLE F2

Table-F2: The synergistic fungicidal activity of the compositions of the present invention, wherein the representative compound of formula (I) is particularly compound (I-3) as component (1) and other components (2) selected from the groups (A) to (L) against *Botrytis cinerea* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 10 | | 20 | | |
| 2 | Tebuconazole | 0.1 | | 38 | | |
| 3 | Propineb | 0.1 | | 22 | | |
| 4 | Benzovindiflupyr | 0.05 | | 33 | | |
| 5 | Fluindapyr | 0.05 | | 27 | | |
| 6 | Fluindapyr | 0.1 | | 41 | | |
| 7 | Compound (I-3) + Tebuconazole | (10:0.1) | 100:1 | 83 | 69 | 14 |
| 8 | Compound (I-3) + Propineb | (10:0.1) | 100:1 | 76 | 61 | 15 |
| 9 | Compound (I-3) + Benzovindiflupyr | (10:0.05) | 200:1 | 83 | 67 | 16 |
| 10 | Compound (I-3) + Fluindapyr | (10:0.05) | 200:1 | 76 | 64 | 13 |
| 11 | Compound (I-3) + Fluindapyr | (10:0.1) | 100:1 | 83 | 71 | 12 |

Example G: *Pseudoperonospora cubensis* Test (Cucumber)

Single compounds or compound combinations were dissolved in 24% dimethyl sulfoxide/acetone and then mixed with water containing emulsifier to a to calibrated spray volume of 30 mL. The test solutions were poured into the spray bottles for further applications.

To test the preventive activity of the single compounds and their combinations, healthy young cucumber plants, raised in the greenhouse, were sprayed with the active compound preparation at the stated application rates inside the spray cabinets using hallow cone nozzles. One day after treatment, the plants were inoculated with conidial spore suspension containing $2\times10^4$ *Pseudoperonospora cubensis* inoculum. The inoculated plants were then kept in a greenhouse chamber at 23° C. temperature & 80-90% relative humidity for disease expression.

A visual assessment of the performance of the compounds and the respective compound combinations was carried out by rating the disease severity (0-100% scale) on treated plants 3, 7, 10 and 15 days after application. Efficacy (% control) of the compounds was calculated by comparing the disease rating in the treatment with the one of the untreated control. The compounds were also assessed for their plant compatibility by recording symptoms like necrosis, chlorosis and stunting.

The results are shown for the representative compounds of compound of formula (I) particularly, (I-3) and (I-8) in Table G1-G2 respectively.

Surprisingly, the following combinations, indicated in the table below, have revealed unexpected synergistic effects:

TABLE G1

Table-G1: The synergistic fungicidal activity of the compositions of the present invention, wherein the representative compounds of formula (I) is particularly compound (I-3) as component (1) and other components (2) selected from the groups (A) to (L) against *Pseudoperonospora cubensis* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 1 | | 32 | | |
| 2 | Compound (I-3) | 10 | | 34 | | |
| 3 | Compound (I-3) | 0.1 | | 36 | | |
| 4 | Fluopyram | 0.05 | | 2 | | |
| 5 | Fluopyram | 0.1 | | 12 | | |
| 6 | Mancozeb | 0.05 | | 2 | | |
| 7 | Mancozeb | 0.1 | | 5 | | |

TABLE G1-continued

Table-G1: The synergistic fungicidal activity of the compositions of the present invention, wherein the representative compounds of formula (I) is particularly compound (I-3) as component (1) and other components (2) selected from the groups (A) to (L) against *Pseudoperonospora cubensis* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 8 | Fluindapyr | 0.05 | | 35 | | |
| 9 | Compound (I-3) + Fluopyram | (10:0.05) | 200:1 | 57 | 38 | 19 |
| 10 | Compound (I-3) + Fluopyram | (5:0.1) | 50:1 | 57 | 42 | 15 |
| 11 | Compound (I-3) + Fluopyram | (10:0.1) | 100:1 | 66 | 44 | 22 |
| 12 | Compound (I-3) + Mancozeb | (5:0.05) | 100:1 | 52 | 35 | 17 |
| 13 | Compound (I-3) + Mancozeb | (10:0.05) | 200:1 | 61 | 38 | 24 |
| 14 | Compound (I-3) + Mancozeb | (1:0.1) | 10:1 | 48 | 35 | 13 |
| 15 | Compound (I-3) + Mancozeb | (5:0.1) | 50:1 | 61 | 37 | 24 |
| 16 | Compound (I-3) + Fluindapyr | (10:0.05) | 200:1 | 70 | 59 | 12 |

TABLE G2

Table-G2: The synergistic fungicidal activity of the compositions of the present invention, wherein the representative compounds of formula (I) is particularly compound (I-8) as component (1) and other components (2) selected from the groups (A) to (L) against *Pseudoperonospora cubensis* in cucumber are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-8) | 1 | | 17 | | |
| 2 | Compound (I-8) | 5 | | 19 | | |
| 3 | Compound (I-8) | 10 | | 28 | | |
| 4 | Prothioconazole | 0.1 | | 45 | | |
| 5 | Fluopyram | 0.05 | | 2 | | |
| 6 | Fluopyram | 0.1 | | 12 | | |
| 7 | Mancozeb | 0.05 | | 2 | | |
| 8 | Mancozeb | 0.1 | | 5 | | |
| 9 | Compound (I-8) + Prothioconazole | (1:0.1) | 10:1 | 64 | 54 | 10 |
| 10 | Compound (I-8) + Prothioconazole | (5:0.1) | 50:1 | 67 | 56 | 11 |
| 11 | Compound (I-8) + Prothioconazole | (10:0.1) | 100:1 | 72 | 60 | 12 |
| 12 | Compound (I-8) + Fluopyram | (1:0.05) | 20:1 | 42 | 18 | 23 |
| 13 | Compound (I-8) + Fluopyram | (5:0.05) | 100:1 | 50 | 21 | 29 |
| 14 | Compound (I-8) + Fluopyram | (10:0.05) | 200:1 | 61 | 29 | 32 |
| 15 | Compound (I-8) + Fluopyram | (1:0.1) | 10:1 | 39 | 27 | 12 |
| 16 | Compound (I-8) + Fluopyram | (5:0.1) | 50:1 | 44 | 29 | 15 |
| 17 | Compound (I-8) + Fluopyram | (10:0.1) | 100:1 | 56 | 36 | 19 |
| 18 | Compound (I-8) + Mancozeb | (1:0.05) | 20:1 | 33 | 18 | 15 |
| 19 | Compound (I-8) + Mancozeb | (5:0.05) | 100:1 | 44 | 21 | 23 |
| 20 | Compound (I-8) + Mancozeb | (10:0.05) | 200:1 | 50 | 29 | 21 |
| 21 | Compound (I-8) + Mancozeb | (1:0.1) | 10:1 | 44 | 21 | 24 |
| 22 | Compound (I-8) + Mancozeb | (5:0.1) | 50:1 | 50 | 23 | 27 |
| 23 | Compound (I-8) + Mancozeb | (10:0.1) | 100:1 | 56 | 31 | 24 |

Example H: *Corynespora cassiicola* Test (Tomato)

Single compounds or compound combinations were dissolved in 2% dimethyl sulfoxide/acetone and then mixed with water containing emulsifier to a calibrated spray volume of 30 mL. The test solutions were poured into spray bottles for further applications.

To test the preventive activity of the single compounds and their combinations, healthy young tomato plants, raised in the greenhouse, were sprayed with the active compound preparation, at the stated application rates, inside the spray cabinets using hallow cone nozzles. One day after treatment, the plants were inoculated with a spore suspension containing $2.6\times10^6$ *Corynespora cassiicola* inoculum and 2% Malt. The inoculated plants were then kept in a greenhouse chamber at 24° C. temperature & 80-90% relative humidity for disease expression.

A visual assessment of the performance of the compounds and the respective compound combinations was carried out by rating the disease severity (0-100% scale) on treated plants 3, 7 & 10 days after the application. Efficacy (% control) of the compounds was calculated by comparing the disease rating in the treatment with the one of the untreated control. The compounds were also assessed for their plant compatibility by recording symptoms like necrosis, chlorosis and stunting.

The results are shown for the representative compounds of compound of formula (I) particularly, (I-3) in Table H1.

Surprisingly, the following combinations, indicated in the table below, have revealed unexpected synergistic effects:

TABLE H1

Table-H1: The synergistic fungicidal activity of the compositions of the present invention, wherein the representative compounds of formula (I) is particularly compound (I-3) as component (1) and other components (2) selected from the groups (A) to (L) against *Corynespora cassiicola* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-3) | 5 | | 36 | | |
| 2 | Compound (I-3) | 10 | | 45 | | |
| 3 | Fluazinam | 0.1 | | 12 | | |
| 4 | Folpet | 0.1 | | 12 | | |
| 5 | Mancozeb | 0.05 | | 10 | | |
| 6 | Benzovindiflupyr | 0.05 | | 18 | | |
| 7 | Inpyrfluxam | 0.05 | | 16 | | |
| 8 | Compound (I-3) + Fluazinam | (5:0.1) | 50:1 | 55 | 44 | 11 |
| 9 | Compound (I-3) + Folpet | (5:0.1) | 50:1 | 55 | 44 | 11 |
| 10 | Compound (I-3) + Folpet | (10:0.1) | 100:1 | 70 | 52 | 19 |
| 11 | Compound (I-3) + Mancozeb | (5:0.05) | 100:1 | 57 | 42 | 14 |
| 12 | Compound (I-3) + Benzovindiflupyr | (5:0.05) | 100:1 | 61 | 48 | 14 |
| 13 | Compound (I-3) + Inpyrfluxam | (10:0.05) | 200:1 | 70 | 54 | 17 |

Example I: *Phytopthora infestans* Test (Tomato)

Single compounds or compound combinations were dissolved in 2% dimethyl sulfoxide/acetone and then mixed with water containing emulsifier to a calibrated spray volume of 30 mL. The test solutions were poured into spray bottles for further applications.

The compounds were also assessed for their plant compatibility by recording symptoms like necrosis, chlorosis and stunting.

The results are shown for the representative compounds of compound of formula (I) particularly, (I-8) in Table I1.

Surprisingly, the following combinations, indicated in the table below, have revealed unexpected synergistic effects:

TABLE I1

Table-I1: The synergistic fungicidal activity of the compositions of the present invention, wherein the representative compounds of formula (I) is particularly compound (I-8) as component (1) and other components (2) selected from the groups (A) to (L) against *Phytopthora infestans* in tomato are shown in the table below:

| Sr. No. | Compound | Conc. (ppm) | Ratio | Observed Efficacy (%) | Expected/ Calculated Efficacy | Synergy (Colby's) |
|---|---|---|---|---|---|---|
| 1 | Compound (I-8) | 1 | | 32 | | |
| 2 | Compound (I-8) | 5 | | 42 | | |
| 3 | Boscalid | 0.1 | | 11 | | |
| 4 | Folpet | 0.1 | | 11 | | |
| 5 | Compound (I-8) + Boscalid | (1:0.1) | 10:1 | 56 | 39 | 17 |
| 6 | Compound (I-8) + Boscalid | (5:0.1) | 50:1 | 63 | 48 | 14 |
| 7 | Compound (I-8) + Folpet | (1:0.1) | 10:1 | 56 | 39 | 17 |
| 8 | Compound (I-8) + Folpet | (5:0.1) | 50:1 | 63 | 48 | 14 |

To test the preventive activity of the single compounds and their combinations, healthy young tomato plants, raised in the greenhouse, were sprayed with the active compound preparation, at the stated application rates, inside the spray cabinets using hallow cone nozzles. One day after treatment, the plants were inoculated with a sporangial suspension (in sterile water) containing $0.24\times10^6$ *Phytopthora infestans* inoculum. The inoculation plants were then kept in darkness at 18° C. and 100% humidity. After 24 hours, the plants were transferred to a greenhouse chamber with a temperature of 18° C. and 95-100% relative humidity for the disease expression.

A visual assessment of the performance of the compounds and the respective compound combinations was carried out by rating the disease severity (0-100% scale) on treated plants 3, 7 & 10 days after application. Efficacy (% control) of the compounds was calculated by comparing the disease rating in the treatment with the one of the untreated control.

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

The invention claimed is:

1. A synergistic fungicidal composition comprising a mixture of component (1) and component (2), wherein component (1) is selected from the group consisting of:

2-(4-fluorophenoxy)-1-(4-(5-(trifluoromethyl)-1,2,4-oxadiazol-3-yl)phenyl)ethan-1-one (I-2);

2-((6-fluoropyridin-3-yl)oxy)-1-(4-(5-(trifluoromethyl)-1,2,4-oxadiazol-3-yl)phenyl)ethan-1-one (I-3); or 2-((4-fluorophenyl)amino)-1-(4-(5-(trifluoromethyl)-1,2,4-oxadiazol-3-yl)phenyl)ethan-1-one (I-8); and and component (2) is at least one further active compound selected from the group consisting of):

inhibitors of complex III at Qo site, selected from the group consisting of: azoxystrobin (A001), flufenoxystrobin (A007), fluoxastrobin (A008), kresoxim-methyl (A009), mandestrobin (A010), metominostrobin (A011), orysastrobin (A012), picoxystrobin (A013), pyraclostrobin (A014), pyraoxystrobin (A016), trifloxystrobin (A017), pyribencarb (A019), famoxadone (A021), fenamidone (A021a) and metyltetraprole (A025);

inhibitors of complex III at Qi site, selected from the group consisting of: florylpicoxamid (A044) and metarylpicoxamid (A045);

inhibitors of complex II, selected from the group consisting of benzovindiflupyr (A047), bixafen (A048), boscalid (A049), cyclobutrifluram (A051), fluopyram (A053), flubeneteram (A054), flufenoxadiazam (A055), flutolanil (A056), fluxapyroxad (A057), furametpyr (A058), fluindapyr (A059), isopyrazam (A060), isoflucypram (A062), inpyrfluxam (A063), pyrapropoyne (A066), penflufen (A067), penthiopyrad (A068), pydiflumetofen (A069), N-[2-(3,4-difluorophenyl)phenyl]-3-(trifluoromethyl)pyrazine-2-carboxamide (A070), sedaxane (A071), tecloftalam (A072), and thifluzamide (A073);

other respiration inhibitors, selected from the group consisting of: flumetylsulforim (A093) and fluazinam (A097);

C14 demethylase inhibitors, selected from the group consisting of: cyproconazole (B004), difenoconazole (B005), epoxiconazole (B008), fluoxytioconazole (B009), flutriafol (B013), hexaconazole (B014), propiconazole (B022), prothioconazole (B023), tebuconazole (B025), tetraconazole (B026), triticonazole (B029), mefentrifluconazole (B038), and triforine (B051);

a delta14-reductase inhibitors selected from fenpropimorph (B056);

inhibitors with multi site action, selected from the group consisting of:

copper (H002), copper acetate (H003), copper hydroxide (H004), copper oxychloride (H005), basic copper sulfate (H006), mancozeb (H009), metiram (H012), propineb (H013), chlorothalonil (H018), folpet (H021), and dithianon (H036); and a melanin synthesis inhibitors selected from tricyclazole (I004).

2. The fungicidal composition according to claim 1, wherein the weight of component (1) and a component (2) in the composition is in the weight ratio of from 1000:1 to 1:1000.

3. The fungicidal composition according to claim 1, wherein the weight of component (1) and a component (2) in the composition is in the weight ratio of from 100:1 to 1:100.

4. The fungicidal composition according to claim 1, wherein said composition further comprises an agriculturally acceptable additive(s).

5. The fungicidal composition according to claim 4, wherein said agriculturally acceptable additive(s) is selected from the group consisting of solvent(s) or diluent(s), dye(s), wetting agent(s), dispersant(s), emulsifier(s), antifoam(s), preservative(s), thickener(s), adhesive(s), gibberellins, solid carrier(s), liquid carrier(s), gaseous carrier(s), surfactant(s), binder(s), disintegrating agent(s), pH adjuster(s), anti-caking agent(s), anti-freezing agent(s), defoaming agent(s), extender(s), filler(s), stabilizer(s) and/or coloring agent(s) or combinations thereof.

6. A seed comprising the fungicidal composition according to claim 1.

7. A method for controlling or preventing infestation of useful plants by phytopathogenic fungi in agricultural or horticultural crops, wherein said method comprises applying the fungicidal composition according to claim 1, to the plants, to the area adjacent to the plant, soil adapted to support growth of the plant, to parts thereof or to a locus thereof.

8. A method for controlling or preventing infestation of useful plants by phytopathogenic fungi in agricultural or horticultural crops, comprising treating plants, soil, seeds, seeds of transgenic plants or transgenic plants with the fungicidal composition according to claim 1.

9. The fungicidal composition according to claim 1 further comprising seeds, wherein an amount of active components is 1 g to 1000 g per 100 kg of seeds.

10. The method for controlling or preventing infestation of useful plants by photopathogenic fungi in agricultural crops or horticultural crops according to claim 7, wherein said phytopathogenic fungi is selected from *Alternaria solani, Botrytis cinerea, Phakopsora pachyrhizi, Septoria nodorum, Erysiphe cichoracearum, Pyricularia oryzae, Corynespora cassiicola*, and *Pseudoperonospora cubensis*.

* * * * *